(12) United States Patent
Hirowatari

(10) Patent No.: US 8,076,145 B2
(45) Date of Patent: Dec. 13, 2011

(54) METHOD AND APPARATUS FOR ANALYZING VITAMIN E IN LIPOPROTEINS

(75) Inventor: Yuji Hirowatari, Hadano (JP)

(73) Assignee: Tosoh Corporation, Shunan-shi, Yamaguchi (JP)

( * ) Notice: Subject to any disclaimer, the term of this patent is extended or adjusted under 35 U.S.C. 154(b) by 0 days.

(21) Appl. No.: 13/064,793

(22) Filed: Apr. 15, 2011

(65) Prior Publication Data

US 2011/0195511 A1     Aug. 11, 2011

Related U.S. Application Data

(62) Division of application No. 12/301,508, filed as application No. PCT/JP2007/061143 on May 25, 2007, now Pat. No. 7,981,683.

(30) Foreign Application Priority Data

May 25, 2006    (JP) .................................. 2006-144843

(51) Int. Cl.
    *G01N 33/92*    (2006.01)
    *G01N 30/02*    (2006.01)
    *G01N 30/14*    (2006.01)

(52) U.S. Cl. ............ 436/71; 436/93; 436/161; 436/174; 436/177; 210/656; 210/660; 210/662

(58) Field of Classification Search .................... 436/63, 436/71, 161, 174, 177, 93; 210/656, 660, 210/662; 422/70

See application file for complete search history.

(56) References Cited

FOREIGN PATENT DOCUMENTS

| JP | 2000-214150 | 8/2000 |
| JP | 2004-101477 | 4/2004 |

OTHER PUBLICATIONS

International Search Report for PCT/JP2007/061143, mailed Sep. 4, 2007.
Yasuda, Kazuto et al., "Tonyobyo to Vitamin E Taisha", The Japanese Journal of Clinical Pathology, vol. 29, No. 6, (1981 Nen 6 Gatsu), pp. 586-589.
Caye-Vaugien, Colette et al., "Determination of α-Tocopherol in Plasma, Platelets and Erythrocytes of Type I and Type II Diabetic Patients by High-Performance Liquid Chromatophraphy", Vitamin and Nutrition Research, vol. 60, No. 4, (1990), pp. 324-330.
Hirowatari, Yuji et al., "Analysis Method for Lipoproteins by High-Performance Liquid Chromatography with Sulfopropyl-Ligand Column and Magnesium Ion-Containing Eluents", Analytical Biochemistry, vol. 308, No. 2, (2002), pp. 336-342.
Hirowatari, Yuji et al., "Measurement of Cholesterol of Major Serum Lipoprotein Classes by Anion-Exchange HPLC with Perchlorate Ion-Containing Eluent", Journal of Lipid Research, vol. 44, No. 7, (Jul. 2003), pp. 1404-1412.

(Continued)

*Primary Examiner* — Maureen Wallenhorst
(74) *Attorney, Agent, or Firm* — Nixon & Vanderhye P.C.

(57) ABSTRACT

A method of analyzing vitamin E components in a lipoprotein by subjecting a lipoprotein-containing sample to ion exchange chromatography to separate the lipoprotein, reacting the separated lipoprotein to a pretreating solution containing an organic solvent and a surfactant to liberate vitamin E components, and then subjecting the liberated vitamin E components to reverse phase chromatography. Also described is a method of judging various pathological conditions such as the pathological conditions of diabetes, the risks of coronary artery diseases, and the pathological conditions of myocardial infarction using levels of vitamin E components in the lipoprotein as an index.

3 Claims, 34 Drawing Sheets

OTHER PUBLICATIONS

Cooper, J.D.H. et al., "Determination of Vitamin E in Human Plasma by High-Performance Liquid Chromatography", Journal of Chromatography B., vol. 690, No. 1/2, (Mar. 7, 1997), pp. 355-358.

Extended European Search Report in EP 07 74 4531 dated Apr. 9, 2010.

Granado et al, "Carotenoids, Retinol and Tocopherols in Patients with Insulin-Dependent Diabetes Mellitus and Their Immediate Relatives", Clinical Since, Biochemical Society and the Medical Research Society, London, GB, vol. 94, No. 2, Feb. 1, 1988, pp. 189-195, XP009085796.

Olmedilla et al, "Reference values for retinol, tocopherol, and main carotenoids in serum of control and insulin-dependent diabetic Spanish subjects", Clinical Chemistry Jun. 1997, vol. 43, No. 6 Pt 1, Jun. 1997, pp. 1066-1071, XP002574562.

Knekt et al, "Low vitamin E status is a potential risk factor for insulin-dependent diabetes mellitus", Journal of Internal Medicine, Jan. 1999, vol. 245, No. 1, pp. 99-102, XP002574563.

Vatassery et al, "Vitamin E in Plasma and Platelets of Human Diabetic Patients and Control Subjects", American Journal of Clinical Nutrition, vol. 37, No. 4, Apr. 1983, pp. 641-644, XP002574564.

Sobszak et al, Journal of Chromatogaphy B, vol. 730, 1999, pp. 265-271.

Haidari et al, Clinical Chemistry, vol. 47, No. 7, 2001, pp. 1234-1240.

Williamson et al, Abstract No. 120.2 Experimental Biology 2006: Meeting Abstracts, Mar. 6, 2006, pp. A144-A145.

Schneider et al, Diabetes, vol. 53, Oct. 2004, pp. 2633-2639.

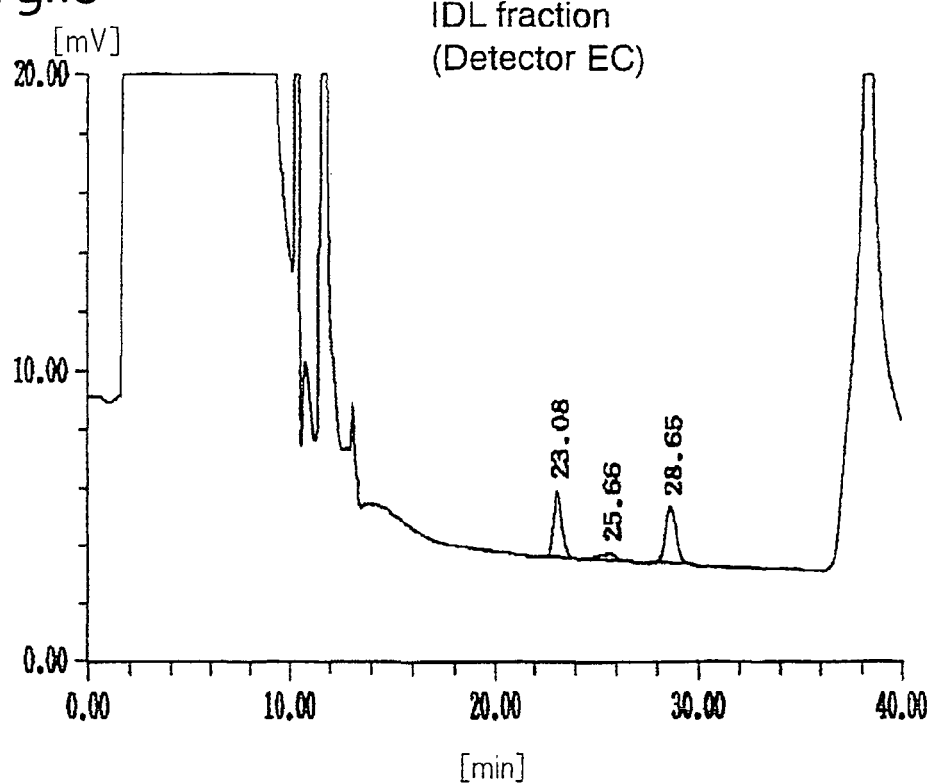
Fig.18 IDL fraction (Detector EC)
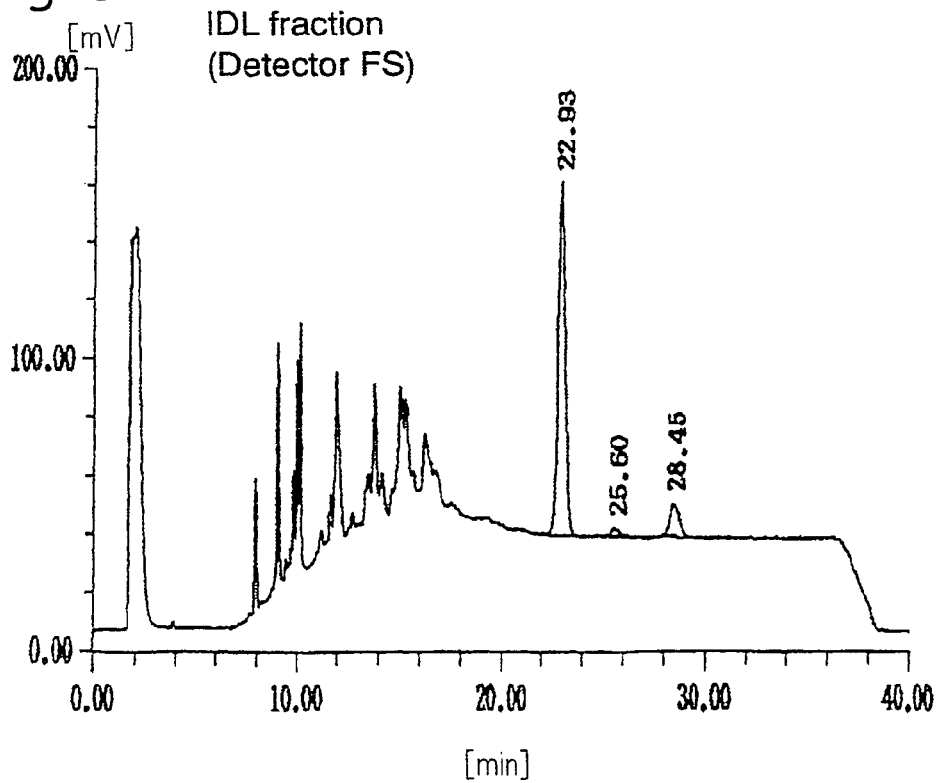
Fig.19 IDL fraction (Detector FS)

γ-tocopherol/cholesterol in CM (mmol/mol)

γ-tocopherol/cholesterol in serum (mmol/mol)

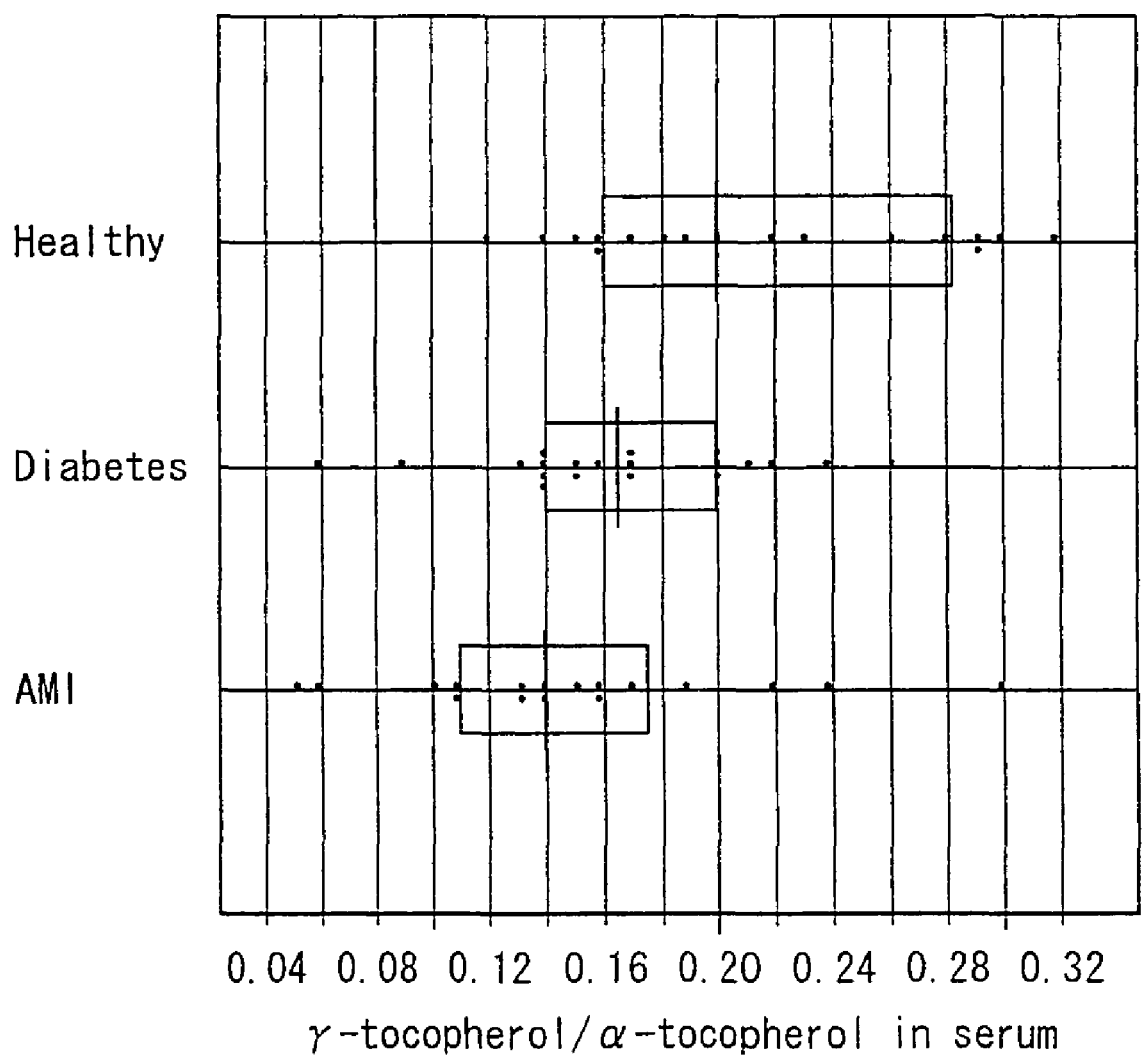

METHOD AND APPARATUS FOR ANALYZING VITAMIN E IN LIPOPROTEINS

This application is a divisional of application Ser. No. 12/301,508 filed Nov. 19, 2008, now U.S. Pat. No. 7,981,683, which in turn is the U.S. national phase of International Application No. PCT/JP2007/061143, filed 25 May 2007, which designated the U.S. and claims priority to Japan Application No. 2006-144843, filed May 25, 2006, the entire contents of each of which are hereby incorporated by reference.

TECHNICAL FIELD

The present invention relates to a method of analyzing vitamin E such as α-tocopherol or γ-tocopherol contained in lipoproteins (high density lipoprotein/HDL, low density lipoprotein/LDL, intermediate density lipoprotein/IDL, very low density lipoprotein/VLDL, chylomicron/CM etc.) in a sample, and an analytical apparatus that can be used in such an analysis. Furthermore, the present invention provides a method of judging various pathological conditions such as diabetes and myocardial infarction, and the risks of coronary artery diseases, using vitamin Es in the lipoprotein as an index.

BACKGROUND ART

As a risk factor for arteriosclerosis, oxidized lipoproteins are attracting a lot of attention and extensive studies are underway, and a major antioxidant contained in the lipoprotein is vitamin E (mainly α-tocopherol and γ-tocopherol). Thus, the analysis of vitamin E in each lipoprotein in the blood is thought to be important in understanding the mechanism of arteriosclerosis. Especially, on one of vitamin E, α-tocopherol, abundantly contained in the serum lipoproteins, various academic studies have been reported as follows.

(1) Haidari M. et al., Clin. Chem. 47: 1234 (2001); α-tocopherol/cholesterol levels in LDL are reduced in patients with coronary artery diseases compared to healthy individuals.

(2) Feki M. et al., Clin. Chem. 46: 1401 (2000); α-tocopherol/cholesterol levels in LDL are reduced in patients with coronary artery diseases compared to healthy individuals.

In the blood of patients with diabetes, it is also believed that active oxygen (radical) is abundantly generated and thus oxidant stress becomes enhanced, which attacks the cell causing various complications (Beisswenger P J et al., Diabetes 54: 3274 (2005)). This oxidant stress is one of the causes of vascular inflammation, and is also one of the mechanisms of progress of arteriosclerosis. (Renard C. et al., Diabetes Metab. 32: 15 (2005)). Vitamin E (γ-tocopherol and α-tocopherol) is one of the antioxiding agents of a cell membrane, and is transported via lipoprotein into the body. Vitamin E (γ-tocopherol and α-tocopherol) is also one of the antioxiding agents of the lipoprotein.

Though little is known of the relationship between vitamin E contained in the lipoprotein in the blood and diseases, there are the following reports in addition to the above:

(3) Yolanda B. et al., Arterioscler. Thromb. Vasc. Biol. 17: 127 (1997); α-tocopherol/cholesterol levels in LDL are enhanced in patients with hyperlipidemia compared to healthy individuals.

Little is also known of the relationship between vitamin E in the blood and diabetes or coronary artery diseases; however there are the following reports:

(4) Salonen J T et al., BMJ 31: 1124 (1995); α-tocopherol/cholesterol levels are reduced in patients with diabetes compared to healthy individuals.

(5) Reunanen A. et al., Eur. J. Clin. Nutr. 52(2): 89 (1998); Reduced levels of α-tocopherol lead to a higher risk of developing diabetes.

(6) Sobczak A. et al., J. Chromatogr. 730, 265 (1999); α-tocopherol and γ-tocopherol levels are enhanced in patients with diabetes compared to healthy individuals.

(7) Mayer-Davis E J et al., Diabetes Care 25: 2172 (2002); α-tocopherol levels are reduced in patients with diabetes compared to healthy individuals.

(8) Ohrvall M. et al., J. Intern. Med. 239: 111 (1996); γ-tocopherol levels are reduced in patients with coronary artery diseases compared to healthy individuals but no significant changes in α-tocopherol. The α-tocopherol/γ-tocopherol ratio becomes high.

There are no reports on vitamin E in the lipoproteins other than the above, but since vitamin E are contained in other lipoproteins, research on the etiology and treatment of arteriosclerosis and diabetes are likely to make a great progress by comprehensive investigation on the amount of vitamin E in each lipoprotein.

As a conventional method of analyzing vitamin E in the lipoprotein, a method is known in which after each lipoprotein is separated, vitamin E are extracted by hexane, the extracted solution is dried, and then redissolved in methanol etc., and subjected to a reverse phase chromatography (Haidari M. et al., Clin. Chem. 47: 1234 (2001); Feki M. et al., Clin. Chem. 46: 1401 (2000); Yolanda B. et al., Arteriosclerosis Throbosis and Vascular Biology 17: 127 (1997); Teissier E. et al., Clinical Chemistry 42: 430 (1996)). For the separation of each lipoprotein, there are known a method comprising ultracentrifugation (Haidari M. et al. (2001), supra; Feki M. et al. (2000), supra; Yolanda B. et al. (1997), supra; Teissier E. et al. (1996), supra), a method comprising acrylamide electrophoresis, a method comprising gel filtration chromatography, and a method comprising ion exchange chromatography (Hirowatari Y. et al., J. Lipid Research 44: 1404 (2003); Hirowatari Y. et al., Anal. Biochem. 308: 336 (2002)).

For the separation of each lipoprotein, an ion exchange chromatography has been proposed (Hirowatari Y. et al. (2003), supra) that permits successful separation of each lipoprotein utilizing subtle changes in electric charge by varying the composition of the eluant or the separation conditions. However, the analysis of vitamin E in each lipoprotein requires, as described above, complicated steps of, after separation of each lipoprotein, extracting vitamin E, concentrating to dryness, redissolving, and subjecting to a reverse phase chromatography, and thus it was prone to errors and required a great deal of efforts and time. Though the measurement of changes in vitamin E in each lipoprotein and in the blood and their use as one of the methods for judging the pathological conditions is important in such diseases as diabetes and coronary artery diseases in which oxidative stress and the pathological conditions are closely related, ultracentrifugation is the only available method for measuring vitamin E in each lipoprotein, which is an expensive apparatus and the operation is complicated, and thus research has not made much progress. Furthermore, for vitamin E in the blood extraction by an organic solvent is necessary, the procedure is complicated, and the evaluation result on diabetes is different with researchers.

DISCLOSURE OF THE INVENTION

Thus the primary object of present invention is to provide a method of analyzing vitamin E in lipoproteins that permits the qualitative and quantitative measurement of vitamin Es in a process which is simplified to the extent amenable to automatic analysis, and an analytical apparatus that enables to automatically carry out said analytical method. Furthermore, by using such an analytical method and an analytical apparatus, the present inventor has found that by using vitamin E in the lipoprotein as an index, various pathological conditions such as the pathological conditions of diabetes, the risk of a coronary artery disease, and the pathological conditions of myocardial infarction can be judged.

The present invention made for the above primary objective is as follows:

(1) A method of analyzing vitamin E components in the lipoprotein, which method comprises subjecting a lipoprotein-containing sample to an ion exchange chromatography to separate the lipoprotein, reacting the separated lipoprotein to a pretreating solution containing an organic solvent and a surfactant to liberate vitamin E components, and then subjecting the liberated vitamin E components to a reverse phase chromatography.

(2) The analytical method according to (1) wherein the pretreating solution comprises a 10-50% organic solvent and a 0.2-6.0% surfactant at the step of reacting with the lipoprotein separated by the ion exchange chromatography.

(3) The analytical method according to (1) or (2) wherein the pretreating solution further comprises 50-150 mmol/L of a caotropic ion at the step of reacting with the lipoprotein separated by the ion exchange chromatography.

(4) An analytical apparatus comprising a sample feeding part for collecting a given amount of a sample, an ion exchange chromatography part equipped with an ion exchange column, a reagent mixing part for mixing part or all of the eluted solution from the ion exchange chromatography part with the reagent, a reverse phase chromatography part equipped with a reverse phase column, a detection part for carrying out detection on the eluted solution from the reverse phase chromatography part, and a liquid delivery part for delivering the sample collected at the sample feeding part and the eluant for the ion exchange chromatography, a liquid delivery part for delivering the reagent, and a liquid delivery part for delivering the mixture of the eluted solution from the ion exchange chromatography part and the reagent, and a liquid delivery part for delivering the eluant for the reverse phase chromatography.

After measuring the sera from 20 cases of diabetes and 17 cases of myocardial infarction that are highly related to oxidative stress and 20 healthy individuals as the control using the above analytical method and analytical apparatus, we have discovered a method of judging various pathological conditions such as the pathological conditions of diabetic conditions, the risks of coronary artery diseases, and myocardial infarction using α-tocopherol/cholesterol as an index.

(5) A method of judging the pathological conditions of diabetes using the γ-tocopherol/cholesterol value in the very low density lipoprotein (VLDL).

(6) The method according to (5) wherein when the γ-tocopherol/cholesterol value in the very low density lipoprotein (VLDL) of a subject is lower than the mean value of the healthy individuals, the subject is judged to have the pathological conditions of diabetes, and when it is not lower than the mean value of the healthy individuals, the subject is judged not to have the pathological conditions of diabetes.

(7) A method of judging the risk of a coronary artery disease using the γ-tocopherol/cholesterol value in the very low density lipoprotein (VLDL).

(8) The method according to (7) wherein, in cases where the very low density lipoprotein (VLDL) cholesterol value of a subject is lower than the mean value of the healthy individuals, when the γ-tocopherol/cholesterol value in the very low density lipoprotein (VLDL) of a subject is lower than the mean value of the healthy individuals, the subject is judged to have the risk of a coronary artery disease, and when it is not lower than the mean value of the healthy individuals, the subject is judged to not be at risk for coronary artery disease.

(9) A method of judging the pathological conditions of diabetes using the α-tocopherol/cholesterol value in the low density lipoprotein (LDL).

(10) The method according to (9) wherein when the α-tocopherol/cholesterol value in the low density lipoprotein (LDL) of a subject is higher than the mean value of the healthy individuals, the subject is judged to have the pathological conditions of diabetes, and when it is not higher than the mean value of the healthy individuals, the subject is judged not to have the pathological conditions of diabetes.

(11) A method of judging the pathological conditions of myocardial infarction using the α-tocopherol/cholesterol value in the low density lipoprotein (LDL).

(12) The method according to (11) wherein when the α-tocopherol/cholesterol value in the low density lipoprotein (LDL) of a subject is higher than the mean value of the healthy individuals, the subject is judged to have the pathological conditions of myocardial infarction, and when it is not higher than the mean value of the healthy individuals, the subject is judged not to have the pathological conditions of myocardial infarction.

(13) A method of judging the pathological conditions of diabetes using the α-tocopherol/cholesterol value in the very low density lipoprotein (VLDL).

(14) The method according to (13) wherein when the α-tocopherol/cholesterol value in the very low density lipoprotein (VLDL) of a subject is lower than the mean value of the healthy individuals, the subject is judged to have the pathological conditions of diabetes, and when it is not lower than the mean value of the healthy individuals, the subject is judged not to have the pathological conditions of diabetes.

(15) A method of judging the risk of a coronary artery disease using the α-tocopherol/cholesterol value in the very low density lipoprotein (VLDL).

(16) The method according to (15) wherein, in cases where the very low density lipoprotein (VLDL) cholesterol value of a subject is lower than the mean value of the healthy individuals, when the α-tocopherol/cholesterol value in the very low density lipoprotein (VLDL) of a subject is lower than the mean value of the healthy individuals, the subject is judged to have the risk of a coronary artery disease, and when it is not lower than the mean value of the healthy individuals, the subject is judged not to be at risk for coronary artery disease.

(17) A method of judging the pathological conditions of diabetes using the γ-tocopherol/α-tocopherol ratio in the blood

(18) The method according to (17) wherein when the γ-tocopherol/α-tocopherol ratio in the blood of a subject is lower than the mean value of the healthy individuals, the subject is judged to have the pathological conditions of diabetes, and when it is not lower than the mean value of the healthy individuals, the subject is judged not to have the pathological conditions of diabetes.

Preferably the above methods (5) to (18) may be carried out using any method according to the above (1) to (3) or the apparatus according to the above (4).

As used herein, "lower than the mean value of the healthy individuals" means that the measured α-tocopherol/cholesterol value is lower than the mean value of the healthy individuals by 10%, preferably by 20%, more preferably by 30%, and still more preferably by 50%.

Herein "higher than the mean value of the healthy individuals" means that the measured α-tocopherol/cholesterol value is higher than the mean value of the healthy individuals by 10%, preferably by 20%, more preferably by 30%, and still more preferably by 50%.

Since the measurement of vitamin E concentration (γ-tocopherol and α-tocopherol) in each lipoprotein and of total vitamin E concentration in all the lipoproteins are intended to examine the antioxidant ability of the lipoprotein, it is necessary to investigate the amount of vitamin E per lipoprotein particle. We have decided to determine the amount of vitamin E per lipoprotein by dividing by the value of cholesterol which is an ingredient relatively rich in the lipoprotein. Methods of correction by dividing by cholesterol has generally been used (Haidari M. et al. (2001), supra; Feki M. et al. (2000), supra; Yolanda B. et al. (1997), supra).

BRIEF EXPLANATION OF THE DRAWINGS

FIG. 18 shows the result of analysis of a IDL sample by a reverse phase chromatography and an electrochemical detection.

FIG. 19 shows the result of analysis of a IDL sample by a reverse phase chromatography and a fluorescent detection.

FIG. 62 shows the γ-tocopherol/α-tocopherol value in the blood.

BEST MODE FOR CARRYING OUT THE INVENTION

Figure 1:
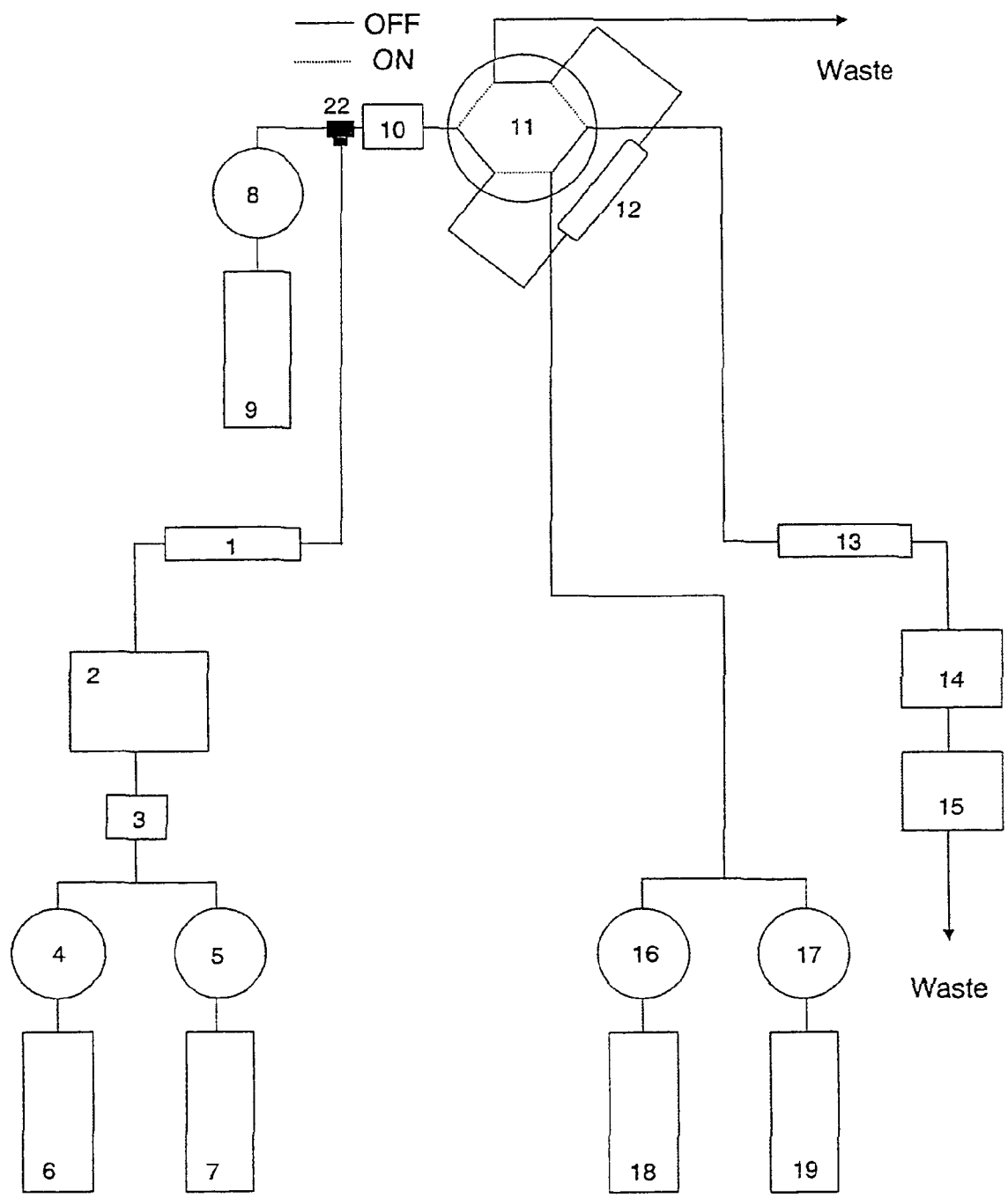
FIG. 1 shows a first example of the analytical apparatus of the present invention.

Lipoproteins are contained in blood (serum). The present invention is an analytical method to be applied to blood samples, but it is not limited to blood in the narrow sense as the sample, but may be applied to samples containing lipoproteins, for example the serum, the plasma, a lipoprotein fraction harvested from the blood or serum, or a suspension obtained by, for example, concentrating said fraction then suspending in a suitable solution, and the like. Vitamin E components to be analyzed in the present invention are mainly α-tocopherol and γ-tocopherol.

The two chromatographic steps of the present invention may preferably be carried out with a column containing a separating agent for use in each chromatography. According to the present invention, the sample is first subjected to an ion exchange chromatography to separate each lipoprotein. The ion exchange chromatography has a high resolution and can precisely separate various lipoproteins, and the separating agent (ion exchanger) used may most preferably be an anion exchanger (an anionic ion exchanger) for anions whose resolution is higher than that of the cation ion exchanger. Various conditions in the ion exchange chromatography such as the amount of the separating agent used (the volume of an ion exchanger), the composition of the eluant and the flow rate of the eluant may be decided as appropriate depending on the type and amount of the sample to be analyzed by performing various preliminary investigations on the conditions adopted in Examples described below so that each lipoprotein may be separated and collected as a different fraction.

To the eluant to be used in an ion exchange chromatography, a caotropic ion may preferably be added as shown in Examples, since the protein-denaturing effect loosens the higher structure of the apoprotein on the surface of lipoprotein particles and thereby can enhance the destruction of lipoprotein particles and the efficiency of liberating vitamin E components by use of a surfactant. As the caotropic ion, there can be illustrated a perchlorate ion, urea, guanidine, a thiocyanate ion, an iodine ion and the like. The concentration to be added may differ with the strength of caotropic effect of each ion, and for a perchlorate ion or a thiocyanate ion, when mixed with a sample, it is a concentration that gives 50-150 mmol/L, more preferably 50 mmol/L.

When a high concentration of caotropic ion (300 mmol/L or higher in the case of a perchlorate ion or a thiocyanate ion) is added to the eluant, the higher structure of the apoprotein may completely be destroyed resulting in the destruction of the structure of the lipoprotein as well, and thus may cause troubles in the separation of each lipoprotein by an ion exchange chromatography. Thus, when a high concentration of caotropic ion is to be used, it is preferred that after separation of each lipoprotein by an ion exchange chromatography, a high concentration of caotropic ion is added and reacted, or a low concentration of caotropic ion is added to the eluant in an ion exchange chromatography, and the caotropic ion is additionally added to the above fraction.

In the ion exchange chromatography, after lipoprotein in the sample has been adsorbed to a separating agent, it is subjected to a stepped or gradient elution so as to eluate each lipoprotein based on the difference in the electric charge in a stepped or gradient elution; in the case of the stepped elution, the eluted solution may be collected in fractions for each step, or in the case of gradient elution, the eluted solution may be collected in fractions for a given volume. Then, to the entire fractions collected, the pretreating solution may be added at a given volume ratio, or after selecting the lipoprotein-containing fractions from the collected fractions, the pretreating solution may be added to the selected fractions at a given volume ratio, and allowed to react to the lipoprotein. The reaction of the lipoprotein and the pretreating solution may be carried out by merely mixing the two and allowing to stand.

The pretreating solution may comprise an organic solvent for dissolving vitamin E components and a surfactant for destroying the lipoprotein particles and liberating vitamin E components therefrom, and, may comprise, in addition to the above, a reducing agent such as ascorbic acid for preventing the oxidation of vitamin E components, specifically when a caotropic ion has not been added to the eluant in an ion exchange chromatography, the pretreating solution may preferably contain a caotropic ion. The caotropic ion may be added in order to denature the higher structure of apoprotein on the surface of the lipoprotein particles so as to enhance the efficiency of destroying lipoprotein particles as well as to prevent the insolubilization of various proteins contained in the lipoprotein fractions caused by contact with an organic solvent so as to obviate the need of removing insoluble matters resulting from protein by centrifugation or filtering with a fine filter prior to subjecting to a reverse phase chromatography described below. Even if a caotropic ion has been added to the eluant in ion exchange chromatography, it may not preclude the addition of a caotropic ion to the pretreating solution. With regard to the amount mixed of the pretreating solution relative to the lipoprotein-containing fraction, when the lipoprotein fraction eluted from the ion exchange column is excessively diluted the detection sensitivity in the subsequent reverse phase chromatography may be lowered, and depending on the concentration of a surfactant contained in the pretreating solution, mixing in an excessive amount may induce foaming, and thus the amount mixed of the pretreating solution relative to the lipoprotein-containing fraction may preferably be ⅕ to 5 times the amount of the fraction, more preferably ½ to twice the amount of the fraction.

As the caotropic ion, there can be illustrated a perchlorate ion, urea, guanidine, a thiocyanate ion, an iodine ion and the like. The concentration may vary with the strength of caotropic effect of each ion, and for a perchlorate ion or a thiocyanate ion when mixed with a lipoprotein, it is a concentration that gives 50-150 mmol/L, more preferably 50 mmol/L. The organic solvent may not be specifically limited as long as it can dissolve vitamin E components, and one or more than one selected from ethanol, acetonitrile, methanol, isopropanol or acetone may be illustrated. The concentration may vary with the type of the organic solvent, and in the case of ethanol, it is a concentration that becomes 10 to 50%, more preferably 25% when mixed with the lipoprotein-containing fraction. The surfactant may not be specifically limited as long as it can destroy the lipoprotein alone or in combination with a caotropic ion, and can liberate vitamin E components, and one or more than one selected from sodium dodecyl sulfate (SDS), poly(oxyethylene)sorbitan monolaulate (Tween 20), Triton X-100, Brij 35 or deoxycholic acid. The concentration may vary with the type of the surfactant, and for SDS, according to the investigation of the present inventor, it is a concentration that becomes 6.9 to 208 mmol/L (0.2-6.0% in terms of weight), more preferably 100 mmol/L (2.9% in terms of weight) when mixed with the lipoprotein-containing fraction. The above disclosure for the organic solvent, the surfactant in the pretreating solution and the concentration of the preferably contained caotropic ion is for the purpose of reference, and depending on the type of the actually selected organic solvent, surfactant and the caotropic ion, modifications may be required. Thus, in the analysis of vitamin E components based on the present invention, it is preferred that the optimum range be investigated in advance for the concentration of each component contained in the pretreating solution.

Vitamin E components liberated from the lipoprotein by the reaction with the pretreating solution may be subjected to a reverse phase chromatography as a mixed solution of the lipoprotein-containing fraction and the pretreating solution. Vitamin E analysis may be carried out by a gas chromatography, a thin layer chromatography, NMR etc., but since a salt-containing eluant is used in separating and eluting each lipoprotein-containing fraction by an ion exchange chromatography, the present invention adopts a reverse phase chromatography that permits precise analysis of salt-containing analytes. By subjecting the above sample mixed with the pretreating solution to a reverse phase chromatography using a eluant containing an organic solvent, vitamin E components are separated and eluted, and detected by a detector to analyze each vitamin E. Various conditions such as the amount of the separating agent, the composition of the eluant, and the flow rate of the eluant used are determined as appropriate by performing various preliminary investigations including conditions adopted in the Examples described below depending on the type and amount of samples to be subjected to analysis. After performing an ion exchange chromatography and before performing a reverse phase chromatography, δ-tocopherol, one of vitamin E components, may be added as an internal control to enhance analytical precision. Though δ-tocopherol is one of vitamin E components, its amount in the lipoprotein is as small as about one hundredth that of α-tocopherol, and therefore it can be used as an internal control.

Though, for the detection of vitamin E, a UV-absorption detector, a mass detector, a fluorescence detector, an amperometric electrochemical detector, or a coulombic electrochemical detector etc. may be used, but a fluorescence detector, an amperometric detector, or a coulombic electrochemical detector are preferred because of sufficient detection sensitivity and ease of maintenance works.

Figure 2:
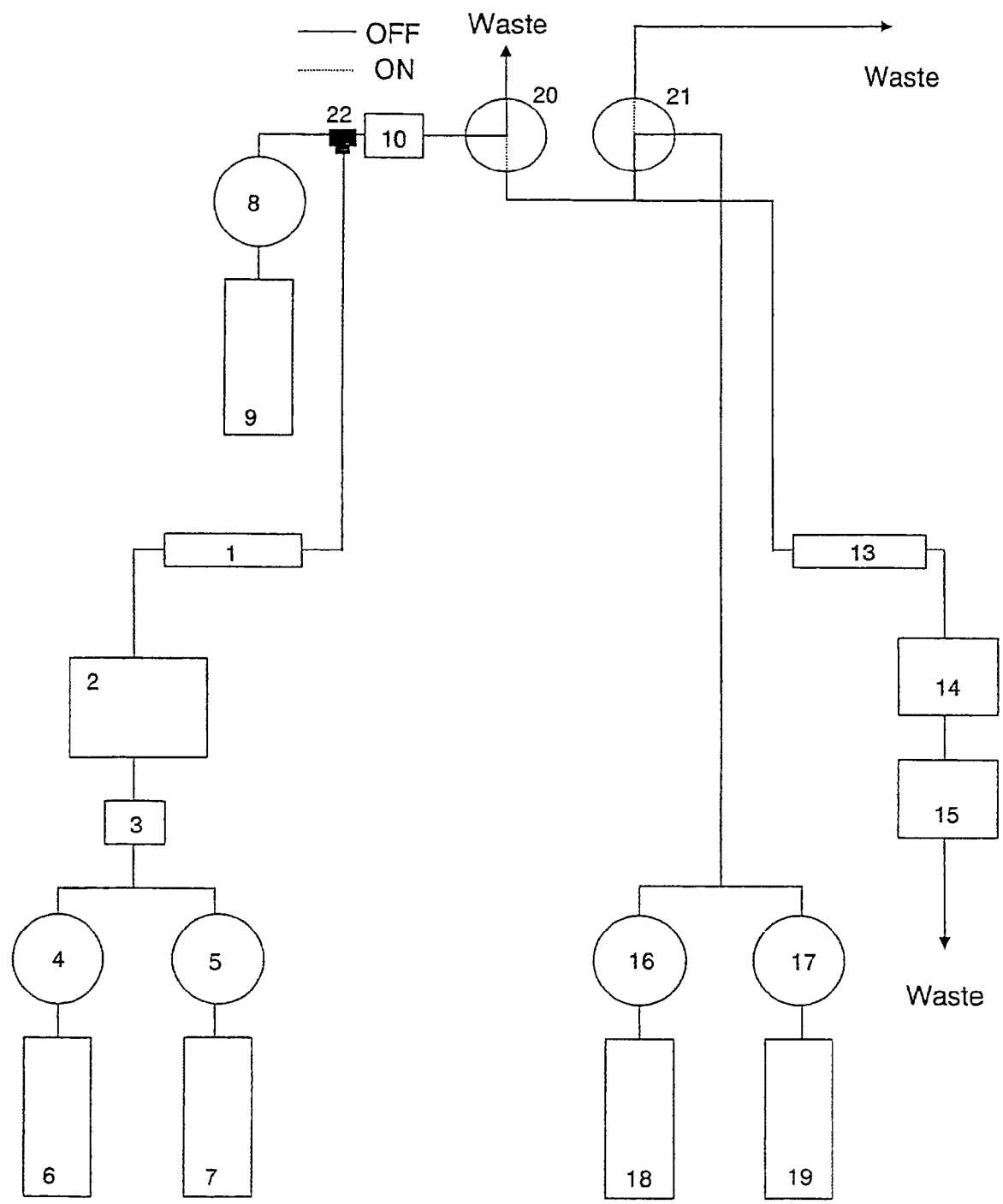
FIG. 2 shows a second example of the analytical apparatus of the present invention.
Figure 3:
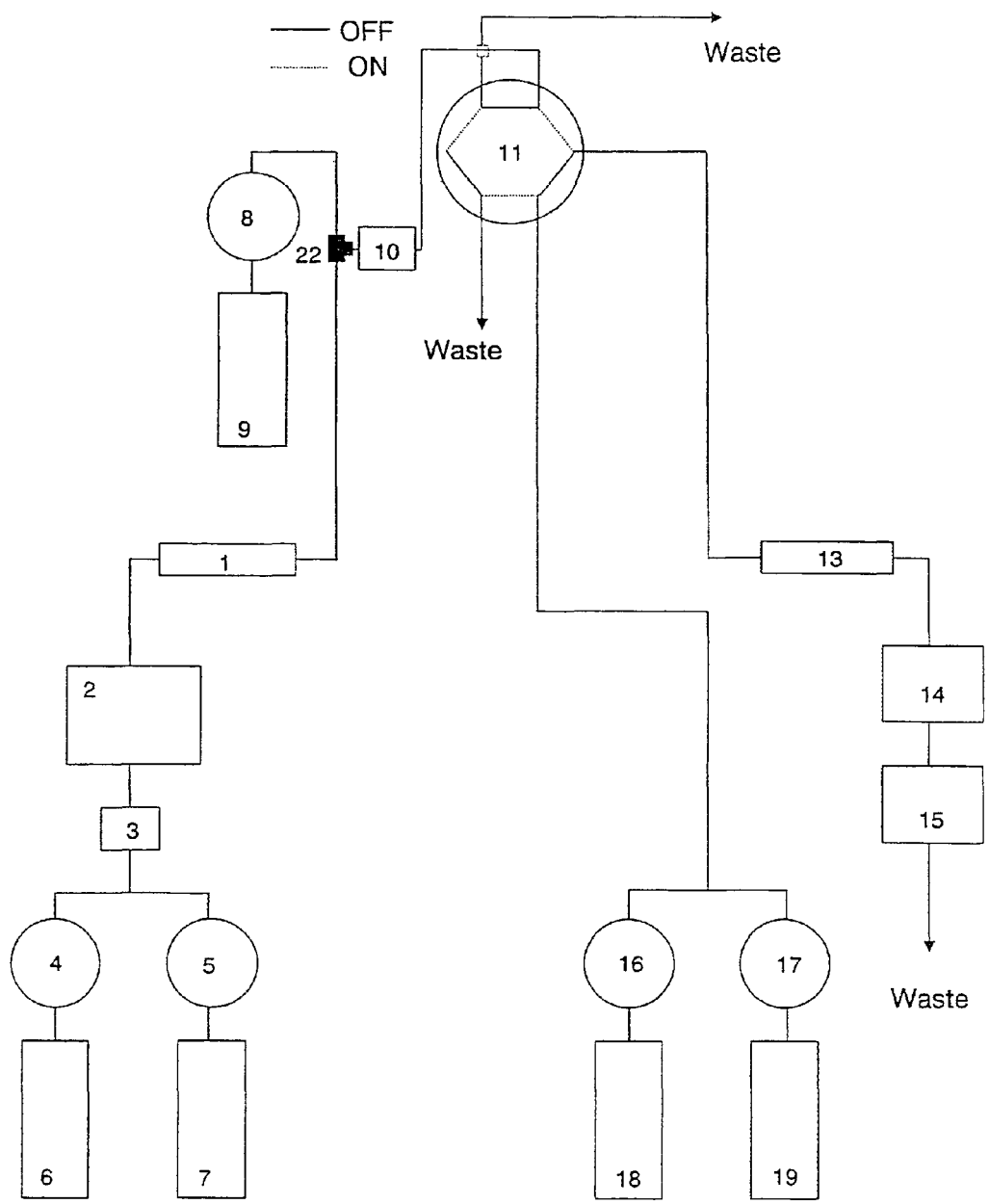
FIG. 3 shows a third example of the analytical apparatus of the present invention.

Next, the analytical apparatus of the present invention will be explained with reference to FIG. 1 to FIG. 3. In the apparatus shown in FIG. 1, the sample feeding part is composed of an autosampler 2 and a pipeline; the ion exchange chromatography part is composed of an ion exchange column 1 and a pipeline; the reagent mixing part that mixes the eluted solution from the ion exchange chromatography part and the reagent is composed of a mixer 10 and a branched pipeline 22 connected immediately there before (upstream side); the reverse phase chromatography part is composed of a reverse phase column 13 and a pipeline; the detecting part that performs detection on the eluted solution from the reverse phase chromatography is composed of a fluorescence detector 14, an amperometric detector 15 and a pipeline; the liquid delivery part that delivers the sample and the eluant for the ion exchange chromatography is composed of a mixing apparatus 3 for the eluant, liquid delivery pumps 4 and 5 and a pipeline; the liquid delivery part for delivering the reagent is composed of a liquid delivery pump 8; and the liquid delivery part for delivering the eluant for the reverse phase chromatography is composed of pumps 16 and 17. In this example, by using a six-way switch valve 11, the delivery of a mixture solution of the eluted solution from the ion exchange chromatography part and the reagent is performed, instead of using a dedicated liquid delivery pump, by a liquid delivery pump 16 and/or 17 for delivering the eluant for the reverse phase chromatography (In the example shown in FIG. 2, by using two three-way switch valves 20 and 21, the liquid delivery pump 8 for delivering the reagent is also used as the liquid delivery pump 16 and/or 17 for delivering the eluant for the reverse phase chromatography, and in the example shown in FIG. 3, by using a six-way switch valve 11, the liquid delivery pump 8 for delivering the reagent is also used as the liquid delivery pump 16 and/or 17 for delivering the eluant for the reverse phase chromatography).

The sample, as it is separately retained in a sample vessel, is carried to the sample feeding part. On the other hand, the eluant for the ion exchange chromatography is connected, as it is separately retained in the eluant vessels 6 and 7, via a pipeline to a pump 4 or 5, the reagent to be mixed with the eluted solution from the ion exchange chromatography part is connected, as it is retained in a reagent vessel 9, to a pump 8, and the eluant for the reverse phase chromatography is connected, as it is separately retained in the eluants 18 and 19, via a pipeline to a pump 16 or 17. Among the eluted solutions from the ion exchange chromatography part, the eluted solutions which have not been subjected to the reverse phase chromatography part and for which detection at the detection part is complete are discarded as a waste to a suitable waste container.

The sample feeding part is not specifically limited as long as it can automatically collect a given amount of the sample from the sample vessel etc. carried to a predetermined site of the sample feeding part, and for example a commonly used autosampler such as AS-8020 (trade name, manufactured by TOSOH Corp.) may be used. The sample feeding part may also be equipped with an apparatus that automatically carries the sample vessel to the above predetermined site.

An ion exchange column 1 that is mounted to the ion exchange chromatography part is not specifically limited as long as it can separate each lipoprotein, and for example DEAE-NPR, DEAE-5PW and SP-NPR (all are trade names, manufactured by TOSOH Corp.) may be used. As described above, specifically an anion exchange column (for example DEAE-NPR (trade name, manufactured by TOSOH Corp.)) may preferably be used. On the other hand, a reverse phase column 13 mounted to the reverse phase chromatography part is not specifically limited as long as it can separate vitamin E, and for example ODS-80Ts (trade name, manufactured by TOSOH Corp.)) may be used.

One round of analysis by a reverse phase chromatography takes a given period of time. When one round takes about 40 minutes, as described in The Examples described below, it is possible that another lipoprotein is eluted from the ion exchange chromatography before the completion of the analysis of any lipoprotein fraction already eluted from the ion exchange chromatography. Thus, it is preferred that the reverse phase column used may be a column that can curtail the analysis time such as a microcolumn so that each lipoprotein fraction eluted from the ion exchange chromatography may be sequentially subjected to the reverse phase chromatography. It is possible, however, to repeat the sequence that, as described in The Examples, after the completion of analysis of a lipoprotein eluted fraction by the reverse phase column, the same sample is fed again to the ion exchange chromatography to collect another lipoprotein eluted fraction, which is then subjected to the reverse phase column so that vitamin E components in each lipoprotein may be analyzed.

The reagent mixing part may be constructed so that part or all of the eluted solution from the ion exchange chromatography part may be mixed with the reagent. In this example, the entire eluted solution from the ion exchange chromatography part is mixed with the reagent, and part of it may be collected by a switch valve 11 and delivered to the reverse phase chromatography part. However, in order to minimize the consumption of the reagent, it is so constructed that the reagent may be mixed with part of the solution. Thus, the elution time of each lipoprotein from the ion exchange column can be predicted if the chromatography condition is constant, and thus the reagent is delivered by pump 8 in tune with the predicted timing and in other times the delivery is stopped. The mixing of the reagent may be effected by, for example, merely joining the pipeline along which the reagent is delivered with the pipeline along which the eluted solution from the ion exchange chromatography part is delivered, but as shown in the example, after joining, mixing may be performed using a mixing apparatus such as the Static mixer B (trade name, manufactured by TOSOH Corp.), or, for example, after joining, the mixture may be passed through a pipeline having a large inner diameter in which the flow rate is lowered to facilitate the mixing of the two, or, for example, pipelines having a rugged surface on the inner wall or pipelines having varying inner diameters may, be used, and the like.

The detection part is not specifically limited as long as it is a detector capable of detecting vitamin E, and for example a UV-absorption detector, a mass detector, a fluorescence detector, an amperometric electrochemical detector, or a coulombic electrochemical detector etc. may be used, but because of sufficient detection sensitivity and ease of maintenance works, a fluorescence detector, an amperometric electrochemical detector, or a coulombic electrochemical detector that were used in the above example are preferred.

If the liquid delivery part that delivers the eluant for the ion exchange chromatography uses the eluants 6 and 7 having a different salt concentration, and the running of the liquid delivery pumps 4 and 5 are controlled by a computer etc. to control the amount of the liquid delivered, eluants having different compositions (salt concentration) can be delivered to the ion exchange column 1 in either of a step or gradient mode. The mixing apparatus 3 is to mix the eluants 6 and 7. As the liquid delivery pumps 4 and 5, for example DP-8020 (trade name, manufactured by TOSOH Corp.) may be used, and as the mixing apparatus 3 a Static mixer C (trade name, manufactured by TOSOH Corp.) may be used.

For the liquid delivery part for delivering the reagent or the liquid delivery part for delivering the eluant for the reverse phase chromatography, a pump such as DP-8020 (trade name, manufactured by TOSOH Corp.) can be used. In this example, by using a six-way switch valve 11, the liquid delivery part for delivering a mixture solution of the eluted solution from the ion exchange chromatography part and the reagent and the liquid delivery part for delivering the eluant for the reverse phase chromatography were simplified. However, as shown in FIG. 2, there can be illustrated the use of three-way switch valves 20 and 21.

In the analysis of vitamin E by the apparatus of FIG. 1, a given amount of the sample collected by an autosampler 2 is delivered together with the eluant for the ion exchange chromatography with a pump 4 and/or 5 to the ion exchange column 1 so that the lipoprotein in the sample may be retained on the column. Subsequently, after delivering an amount of the same eluant, the amount delivered are regulated by pumps 4 and 5 to increase the salt concentration of the eluant to be subjected to the column, and thus each lipoprotein retained on the column may be eluted. For the fraction of each lipoprotein eluted, the reagent (pretreating solution) 9 is delivered by pump 8 to deliver and mix the liquid. With respect to the delivering amount of the pretreating solution 9, when the lipoprotein fraction eluted from the ion exchange column is excessively diluted the detection sensitivity in the subsequent reverse phase chromatography may be lowered, and depending on the concentration of a surfactant contained in the pretreating solution, delivering in an excessive amount may induce foaming, and thus the delivering amount of the eluant relative to the ion exchange column may preferably be ⅕ to 5 times, more preferably ½ to twice the ion exchange column.

Vitamin E components liberated from lipoprotein by mixing with the pretreating solution are then subjected to the reverse phase column 13. By changing the flow path using a six-way switch valve 11, the lipoprotein fraction mixed with the pretreating solution by the liquid delivery pump 8 is introduced to the sample loop 12, and furthermore by changing the flow path using the six-way switch valve 11, the mixed solution is presented to the reverse phase column by the liquid delivery pump 16 and/or 17. The sample loop 12 should be of the volume of the mixed solution to be introduced to the reverse phase column. With regard to the presentation of vitamin E components to the reverse phase column 13, when two three-way switch valves 20 and 21 are used in combination as shown in FIG. 2, the three-way switch valve 20 may be operated to change the flow path to introduce the mixed solution to the reverse phase column 13 during the period from the start to the completion of elution of the lipoprotein fraction from the ion exchange column, and the three-way switch valve 21 may be operated to change the flow path to discard the eluant 18 and/or 19. When a six-way switch valve not equipped with a sample loop is used as shown in FIG. 3, the six-way switch valve 11 may be switched to introduce the mixed solution to the reverse phase column 13 during the period from the start to the completion of elution of the lipoprotein fraction from the ion exchange column. Vitamin E components eluted from the reverse phase column may each be detected by a fluorescence detector 14 and an amperometric detector 15.

As described above, the analytical apparatus in FIGS. 1 to 3 constructed as a analytical apparatus for vitamin E, when an apparatus for automatically carrying the sample vessel to the predetermined place of the sample feeding part and an computer for controlling various parts are added thereto, can automatically analyze vitamin E components in the lipoprotein by merely putting the sample in a vessel and placing it to the carrying apparatus and the like.

Thus, as a result of utilizing the above analytical method and the above analytical apparatus as shown in the Examples below, it became possible to judge various pathological conditions such as the pathological conditions of diabetic conditions, the risks of coronary artery diseases, and the pathological conditions of myocardial infarction using α-tocopherol/cholesterol as an index.

EXAMPLES

The present invention will now be explained in more detail with reference to Examples, but the examples are only embodiments of the present invention and do not limit the present invention in any way.

Example 1

Figure 4:
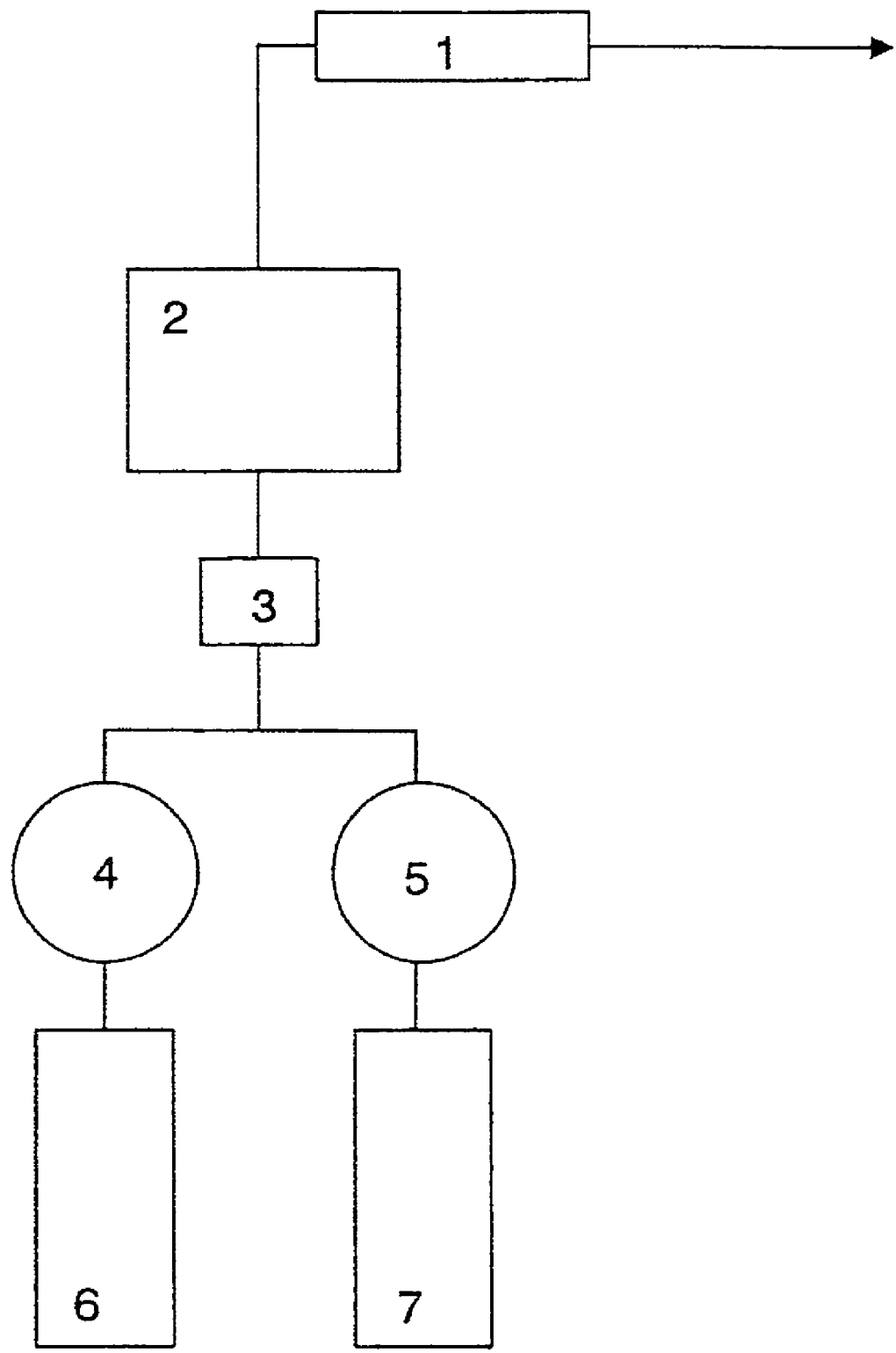
FIG. 4 is a drawing that shows the constitution of the ion exchange chromatography analytical apparatus of Example 1.

A analytical apparatus (FIG. 4) of the following constitution was constructed.

Column 1 for the ion exchange chromatography: Two DEAE-NPR columns (trade name, manufactured by TOSOH Corp.), 4.6 mm ID×35 mm, were connected in series.

Sample feeding part 2: AS-8020 (trade name, manufactured by TOSOH Corp.)

Mixing apparatus 3: Static mixer C (trade name, manufactured by TOSOH Corp.)

Liquid delivery pumps 4 and 5: DP-8020 (trade name, manufactured by TOSOH Corp.)

Eluant A6: 50 mmol/L Tris+1 mmol/L EDTA 2Na, pH 7.5

Eluant B7: 50 mmol/L Tris+1 mmol/L EDTA 2Na+sodium perchlorate 300 mmol/L, pH 7.5

Flow rate of the ion exchange chromatography: 0.5 ml/min

Elution condition of the ion exchange chromatography:

0 minute to 0.05 minute

Eluant B 10%, eluant A 90%

0.05 minute to 5 minutes

Eluant B 38%, eluant A 62%

5 minutes to 11 minutes

Eluant B 44%, eluant A 56%

11 minutes to 16 minutes

Eluant B 49%, eluant A 51%

16 minutes to 21 minutes

Eluant B 56%, eluant A 44%

21 minutes to 29 minutes

Eluant B 100%, eluant A 0%

29 minutes to 40 minutes

Eluant B 10%, eluant A 90%

Time required for separation: 45 minutes/sample

The separation of the lipoprotein by the above apparatus was tested. The fractions separated by an ion exchange chromatography from a serum (total cholesterol 159 mg/dL, triglyceride 492 mg/dL) collected after obtaining the informed consent from an individual who developed a hyperlipidemia and, separately, lipoprotein fractions separated to HDL, LDL, IDL, VLDL, and CM by the ultra centrifugation of the same serum were mixed with a labelling reagent in which parinaric acid (a reagent that adsorbs hydrophobic substances and emits fluorescence) was added to a buffer of 90 mmol/L Tris+80 mmol/L boric acid+3 mmol/L EDTA 2Na, pH9.6, to a concentration of 1.4 ng/mL at a flow rate of 0.15 mL/min, and then detected with the FS-8020 (trade name, a fluorescence detector manufactured by TOSOH Corp., 324 nm, emission wavelength 413 nm).

Figure 5:
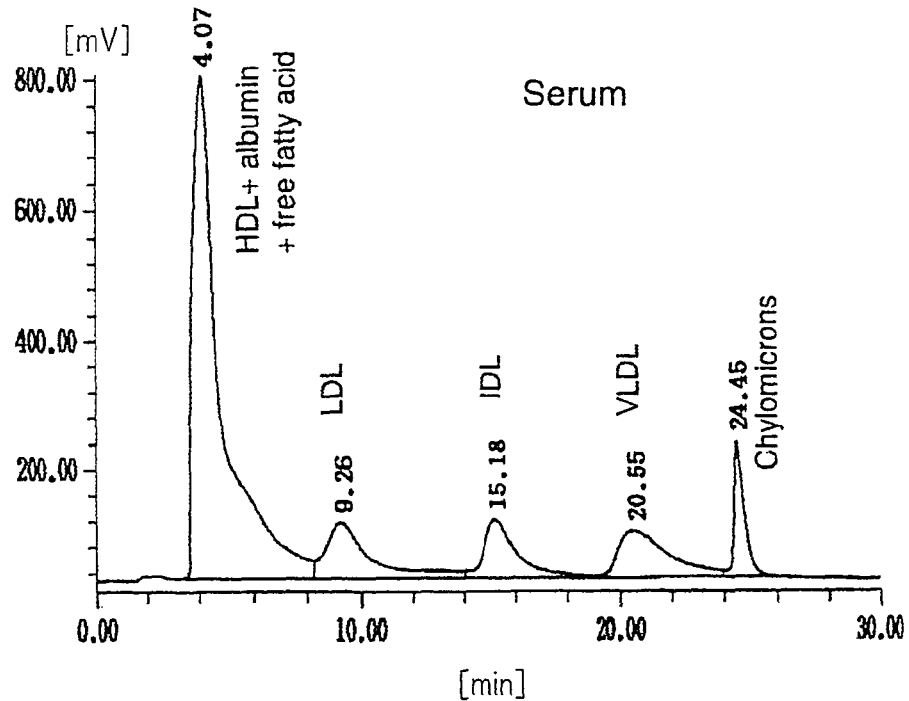
FIG. 5 shows the result of analysis of a serum sample by an ion exchange chromatography.
Figure 6:
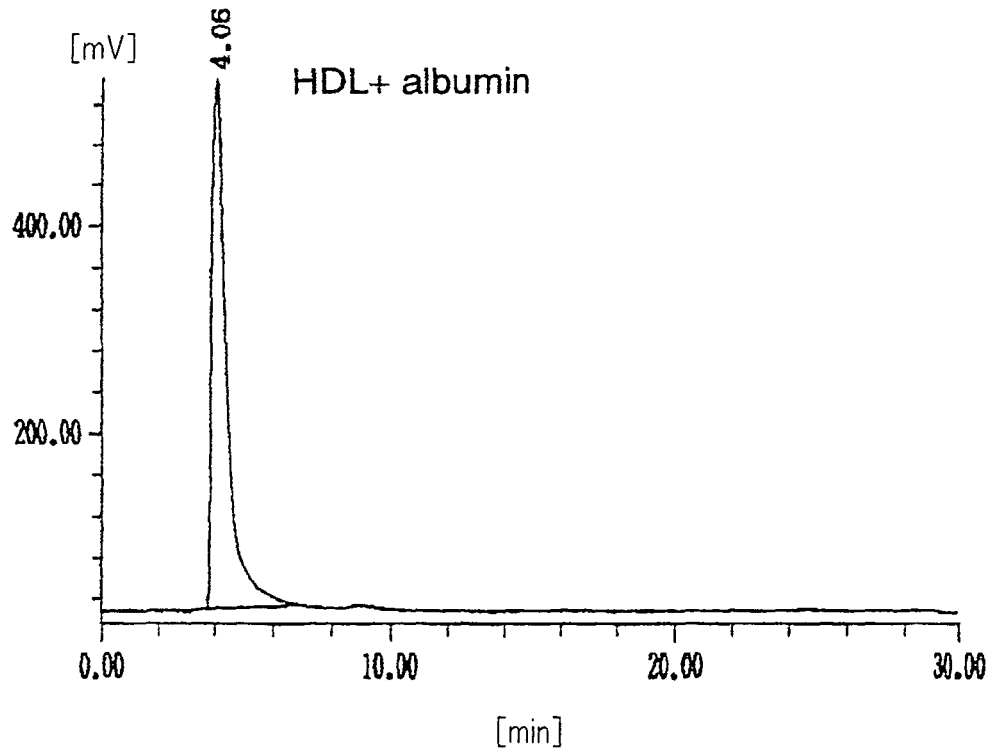
FIG. 6 shows the result of analysis of a HDL sample by an ion exchange chromatography.
Figure 7:
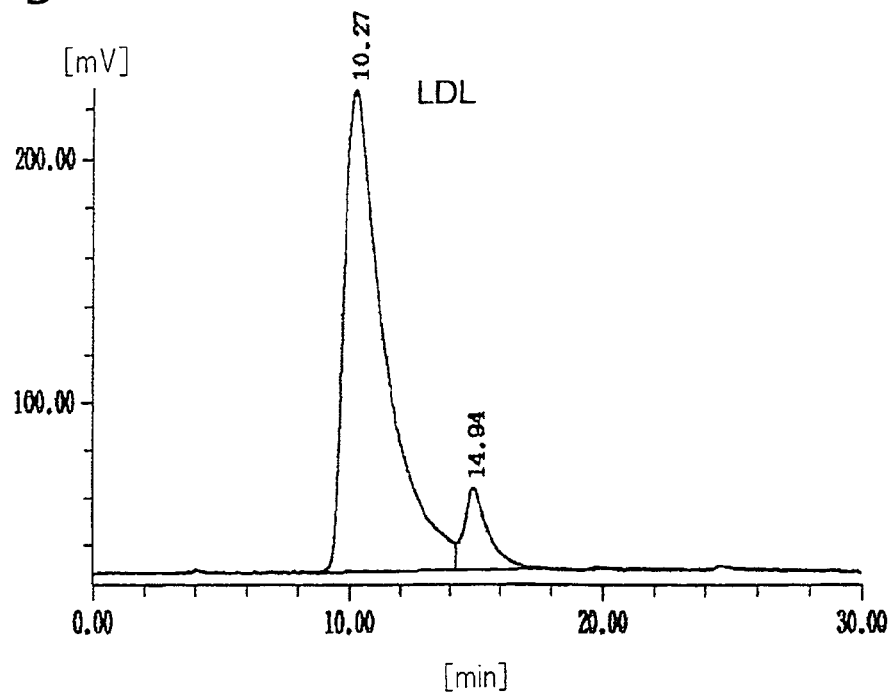
FIG. 7 shows the result of analysis of a LDL sample by an ion exchange chromatography.
Figure 8:
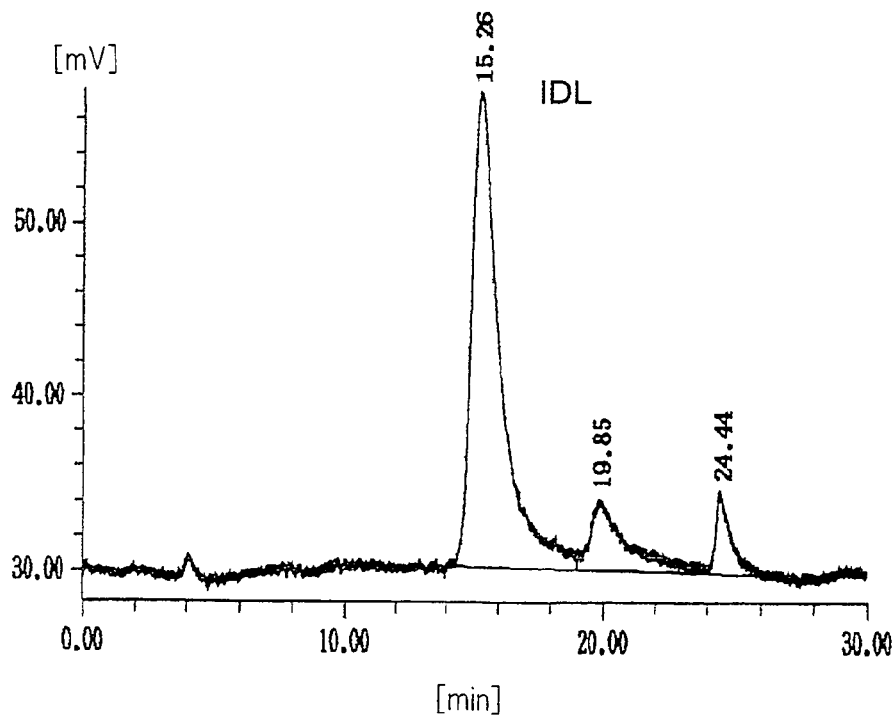
FIG. 8 shows the result of analysis of a IDL sample by an ion exchange chromatography.
Figure 9:
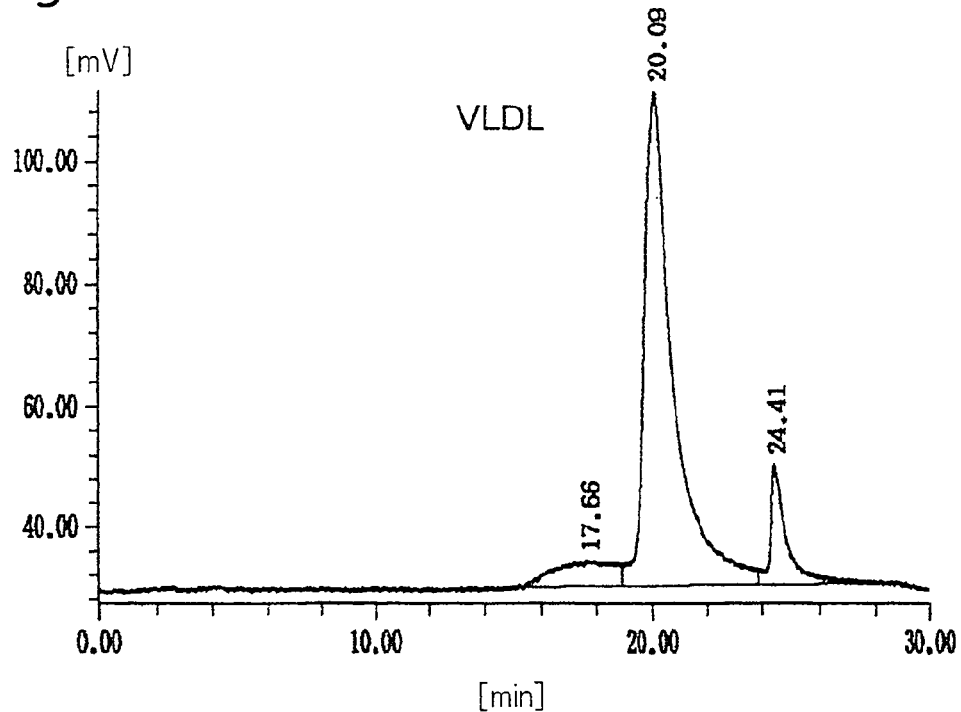
FIG. 9 shows the result of analysis of a VLDL sample by an ion exchange chromatography.
Figure 10:
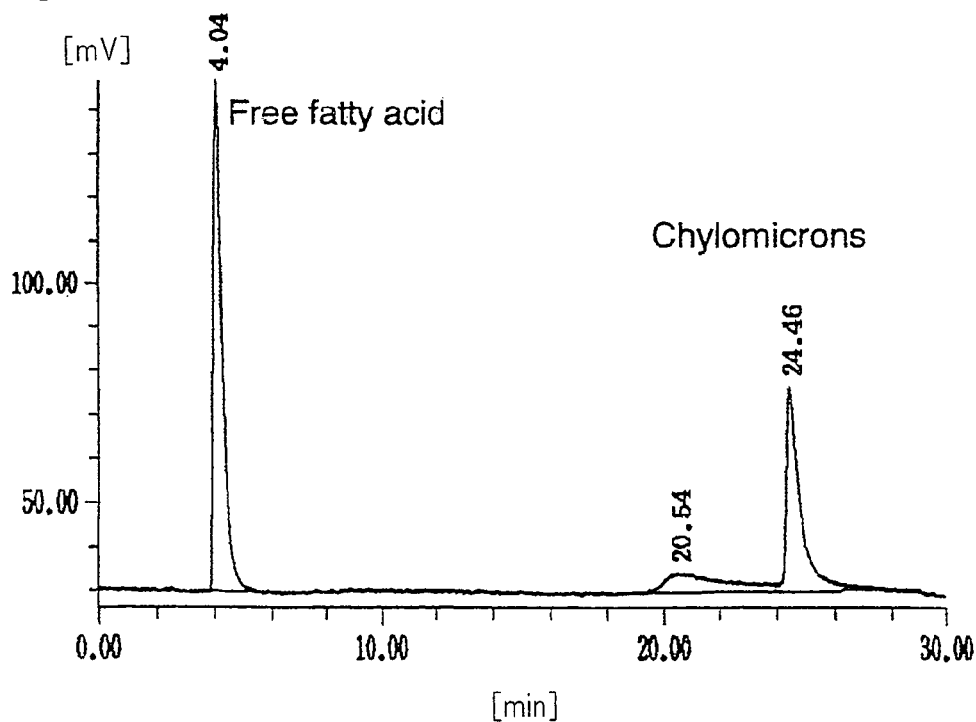
FIG. 10 shows the result of analysis of a CM sample by an ion exchange chromatography.

The results of the serum sample separated by the above apparatus are shown in FIG. 5, and that of preparations by ultracentrifugation of the serum sample are shown in FIGS. 6 to 10. It was confirmed that HDL, LDL, IDL, VLDL, and CM were successfully separated and that albumin and free fatty acids are eluted at the same position as HDL from the comparison with the analytical results of pure products (data not shown).

Example 2

Figure 11:
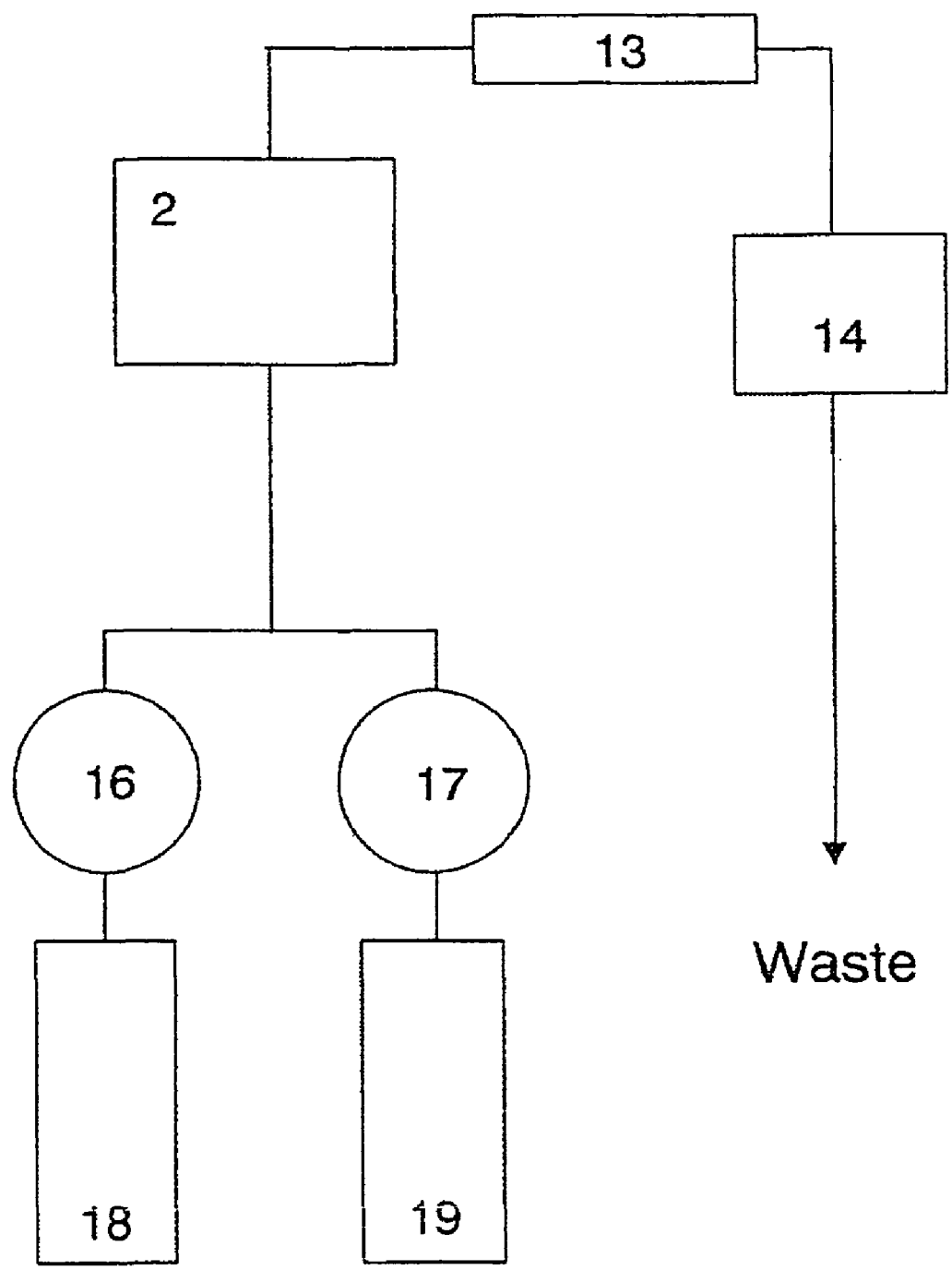
FIG. 11 shows the constitution of the reverse phase chromatography analytical apparatus of Example 2.

A analytical apparatus (FIG. 11) of the following constitution was constructed, and the organic solvent, the surfactant and the caotropic ion of the pretreating solution were tested.

Column 13 for the reverse phase chromatography: ODS-80Ts (trade name, manufactured by TOSOH Corp.), 4.6 mm ID×150 mm Sample feeding part 2: AS-8020 (trade name, manufactured by TOSOH Corp.)

Detector 14: FS-8020 (trade name, a fluorescence detector manufactured by TOSOH Corp.), excitation wavelength 298 nm, emission wavelength 325 nm Liquid delivery pumps 16 and 17: DP-8020 (trade name, manufactured by TOSOH Corp.)

Eluant C18: 30% ethanol+25 mmol/L ammonium nitrate

Eluant D19: 85% ethanol+25 mmol/L ammonium nitrate

Flow rate: 1.0 ml/min

Elution condition:

0 minute to 5 minute

Eluant C 0%, eluant D 100%

5 minutes to 10 minutes

Linear gradient from Eluant C 0%, eluant D 100% to Eluant C 100%, eluant D 0%

10 minutes to 33 minutes

Eluant C 100%, eluant D 0%

33 minutes to 35 minutes

Linear gradient from Eluant C 100%, eluant D 0% to Eluant C 0%, eluant D 100%

35 minutes to 45 minutes

Eluant C 0%, eluant D 100%

Time required for separation: 45 minutes/sample

20 µl of a serum (total cholesterol 215 mg/dL, triglyceride 97 mg/dL) collected after obtaining the informed consent from a healthy individual was subjected to the apparatus of Example 1, and fractions from 0 minute to 8 minutes were collected as the HDL fraction and fractions from 8 minute to 13 minutes were collected as the LDL fraction. The eluted fractions were tested using SDS, Triton X-100 and Tween 20 as the surfactant, and ethanol, acetonitrile and methanol as the organic solvent.

First, the HDL fraction sample was examined (Tables 1 to 3). To 500 µl of the eluted fraction collected, 500 µl of the pretreating solution was added, and after mixing at room temperature for 3 seconds, 500 µl of it was subjected to the above apparatus. The pretreating solution to which were added SDS to a post-mixing concentration (final concentration) of 12.5-100 mmol/L and furthermore 10 mmol/L of ascorbic acid and 1% phosphoric acid for the purpose of stabilizing lipoproteins was added to the HDL fraction, and was subjected to the apparatus and analyzed, with a result that, as shown in Table 1, when SDS was 25 mmol/L, both γ-tocopherol and α-tocopherol gave the highest peak. This reveals that with this condition, vitamin E components were efficiently recovered on the surface of the reverse phase chromatography column.

At the condition of SDS at a final concentration of 25 mmol/L, the pretreating solution to which were added ethanol at a final concentration of 12.5-35%, acetonitrile 25%, and methanol 25%, and, for the purpose of stabilizing lipoproteins, 10 mmol/L of ascorbic acid and 1% phosphoric acid was added to the HDL fraction and was subjected to the apparatus and analyzed, with a result that, as shown in Table 2, the highest peak was obtained at 25% acetonitrile for γ-tocopherol and at 25% methanol for α-tocopherol. This reveals that when SDS is to be used, acetonitrile 25% as the organic solvent is optimum for γ-tocopherol and methanol 25% is optimum for α-tocopherol.

TABLE 1

| No. | Organic solvent name | | Surfactant name | | Peak height (mV) | | Peak height (%) | |
|---|---|---|---|---|---|---|---|---|
| | Name | Conc. (%) | Name | Conc. (mmol/l) | $\gamma$-tocopherol | $\alpha$-tocopherol | $\gamma$-tocopherol | $\alpha$-tocopherol |
| 1 | — | 0 | SDS | 0 | 1.41 | 3.20 | 65 | 62 |
| 2 | — | 0 | SDS | 12.5 | 1.74 | 4.25 | 80 | 82 |
| 3 | — | 0 | SDS | 25 | 2.17 | 5.17 | 100 | 100 |
| 4 | — | 0 | SDS | 50 | 1.84 | 3.36 | 85 | 65 |
| 5 | — | 0 | SDS | 100 | 0.97 | 2.91 | 45 | 56 |

TABLE 2

| No. | Organic solvent name | | Surfactant name | | Peak height (mV) | | Peak height (%) | |
|---|---|---|---|---|---|---|---|---|
| | Name | Conc. (%) | Name | Conc. (mmol/l) | $\gamma$-tocopherol | $\alpha$-tocopherol | $\gamma$-tocopherol | $\alpha$-tocopherol |
| 1 | — | 0 | SDS | 25 | 2.17 | 5.17 | 89 | 65 |
| 2 | Ethanol | 12.5 | SDS | 25 | 1.98 | 5.20 | 81 | 65 |
| 3 | Ethanol | 25 | SDS | 25 | 1.62 | 5.45 | 66 | 68 |
| 4 | Ethanol | 35 | SDS | 25 | 1.87 | 5.00 | 77 | 63 |
| 5 | Acetonitrile | 25 | SDS | 25 | 2.44 | 6.57 | 100 | 82 |
| 6 | Methanol | 25 | SDS | 25 | 2.34 | 8.00 | 96 | 100 |
| 7 | — | 0 | Triton X-100 | 0.5% | 2.17 | 3.02 | — | — |
| 8 | Ethanol | 25 | Triton X-100 | 0.5% | 2.04 | 5.00 | — | — |
| 9 | — | 0 | Tween 20 | 0.5% | 1.95 | 4.09 | — | — |
| 10 | Ethanol | 25 | Tween 20 | 0.5% | 1.76 | 4.39 | — | — |

When SDS as the surfactant was replaced with Triton X-100 or Tween 20 at a final concentration of 0.5%, and ethanol was prepared at a final concentration of 0% or 25%, as shown in Table 2, the effect of ethanol was not noted for $\gamma$-tocopherol, but for $\alpha$-tocopherol, the addition of ethanol at both concentrations gave a strong peak height. This revealed that when SDS is used, acetonitrile or methanol is effective as the organic solvent for the analysis of $\alpha$-tocopherol, and when Triton X-100 or Tween 20 is used, ethanol is effective.

When the pretreating solution to which were added ethanol at a final concentration of 25%, SDS at a final concentration of 0 to 50 mmol/L, and furthermore, for the purpose of stabilizing lipoproteins, and 10 mmol/L of ascorbic acid and 1% phosphoric acid were added to the HDL fraction, and subjected to the apparatus and analyzed, with a result that, as shown in Table 3, the highest peak was obtained at a condition of 50 mmol/L of SDS for both of $\gamma$-tocopherol and $\alpha$-tocopherol. When ethanol 0% and 25% are compared at SDS 50 mmol/L, both $\gamma$-tocopherol and $\alpha$-tocopherol gave a strong peak height in the presence of ethanol, indicating the effect of ethanol addition at 50 mmol/L SDS.

Then using a serum, the effect of sodium perchlorate contained in the pretreating solution was examined (Table 4). Since the HDL fraction contained 114 mmol/L of sodium perchlorate derived from the eluant used for the ion exchange chromatography, the effect of sodium perchlorate was examined. The above serum from a healthy individual was diluted with eluant A or B used in the ion exchange chromatography in the apparatus of Example 1, and the pretreating solution was added so that at a final ethanol concentration of 25% or 0%, the final concentration of SDS is 125 mmol/L, and the final concentrations of ethanol and SDS may be 25% and SDS 25 mmol/L, respectively, and subjected to the apparatus and analyzed, with a result that, as shown in Table 4, in all conditions a stronger peak height was obtained when sodium perchlorate was contained compared to when there was no sodium perchlorate, and furthermore when all of ethanol, SDS and sodium perchlorate were contained, the highest peak height was obtained.

TABLE 3

| No. | Organic solvent name | | Surfactant name | | Peak height (mV) | | Peak height (%) | |
|---|---|---|---|---|---|---|---|---|
| | Name | Conc. (%) | Name | Conc. (mmol/l) | $\gamma$-tocopherol | $\alpha$-tocopherol | $\gamma$-tocopherol | $\alpha$-tocopherol |
| 1 | Ethanol | 25 | SDS | 0 | 1.01 | 2.92 | 54 | 50 |
| 2 | Ethanol | 25 | SDS | 12.5 | 1.27 | 4.05 | 68 | 69 |
| 3 | Ethanol | 25 | SDS | 25 | 1.73 | 5.51 | 93 | 94 |
| 4 | Ethanol | 25 | SDS | 50 | 1.86 | 5.86 | 100 | 100 |
| 5 | Ethanol | 0 | SDS | 50 | 1.84 | 3.36 | 99 | 57 |

TABLE 4

| No. | Organic solvent name | | Surfactant name | | Sodium perchlorate (mmol/l) | Peak height (%) | |
|---|---|---|---|---|---|---|---|
| | Name | Conc. (%) | Name | Conc. (mmol/l) | | γ-tocopherol | α-tocopherol |
| 1 | Ethanol | 25 | SDS | 0 | 0 | 4.3 | 11.4 |
| 2 | Ethanol | 25 | SDS | 0 | 150 | 6.2 | 15.5 |
| 3 | Ethanol | 0 | SDS | 125 | 0 | 5.9 | 8.3 |
| 4 | Ethanol | 0 | SDS | 125 | 150 | 6.3 | 9.4 |
| 5 | Ethanol | 25 | SDS | 25 | 0 | 9.5 | 25.7 |
| 6 | Ethanol | 25 | SDS | 25 | 150 | 9.9 | 30.0 |

Next, the LDL fraction sample was examined (Table 5). The pretreating solution in which at a final ethanol concentration of 25%, SDS was made final concentrations of 0-50 mmol/L, and at a final SDS concentration of 25 mmol/L, the final concentration of acetonitrile or methanol be 25%, and furthermore, for the purpose of stabilizing lipoproteins, 10 mmol/L of ascorbic acid and 1% phosphoric acid were added was added to the LDL fraction and was subjected to the apparatus and analyzed (the LDL sample contains 132 mmol/L of sodium perchlorate derived from the eluant used in the ion exchange chromatography). As a result, similarly to the result when the HDL fraction was used, as shown in Table 5, the peak height of both of γ-tocopherol and α-tocopherol became higher as the SDS concentration became higher, and the highest peak was obtained at the condition of acetonitrile at a final concentration of 25% and SDS at 25 mmol/L.

TABLE 5

| No. | Organic solvent name | | Surfactant name | | Peak height (mV) | | Peak height (%) | |
|---|---|---|---|---|---|---|---|---|
| | Name | Conc. (%) | Name | Conc. (mmol/l) | γ-tocopherol | α-tocopherol | γ-tocopherol | α-tocopherol |
| 1 | Ethanol | 25 | SDS | 0 | 0.97 | 3.69 | 57 | 62 |
| 2 | Ethanol | 25 | SDS | 12.5 | 1.33 | 4.28 | 79 | 71 |
| 3 | Ethanol | 25 | SDS | 25 | 1.36 | 5.34 | 80 | 89 |
| 4 | Ethanol | 25 | SDS | 50 | 1.66 | 5.45 | 98 | 91 |
| 5 | Acetonitrile | 25 | SDS | 25 | 1.69 | 6.00 | 100 | 100 |
| 6 | Methanol | 25 | SDS | 25 | 1.55 | 5.58 | 92 | 93 |

As described above, by mixing the lipoprotein fraction to be subjected to the reverse phase chromatography with the pretreating solution containing an organic solvent, a surfactant and a caotropic ion, vitamin E components in each fraction can be analyzed in a precise and stable manner, and it can be seen that even if the pretreating solution should be subjected to the reverse phase chromatography together with the lipoprotein fraction, the analysis of vitamin E components is not affected.

Example 3

Figure 12:
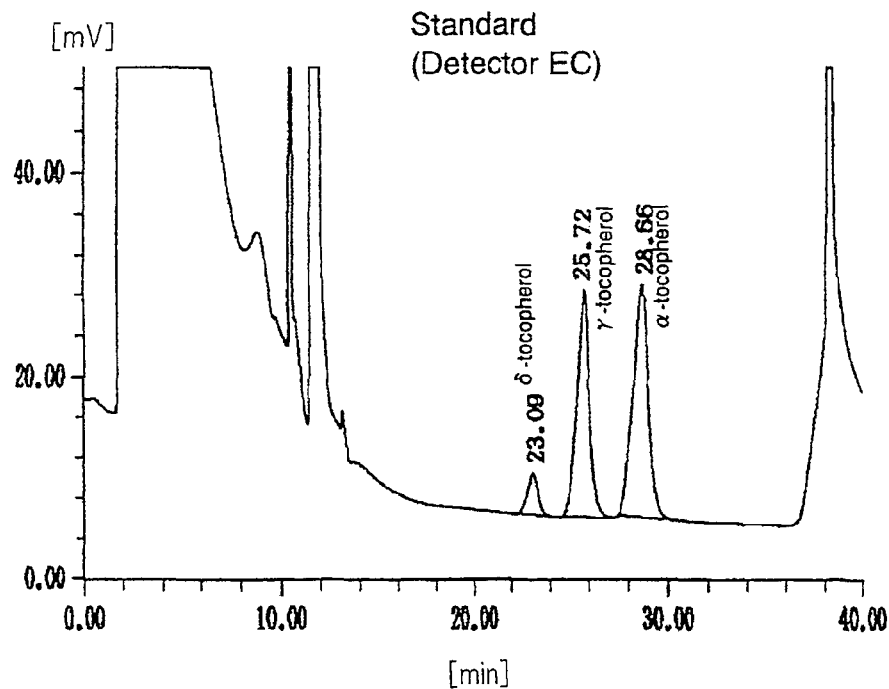
FIG. 12 shows the result of analysis of a vitamin E standard sample by a reverse phase chromatography and an electrochemical detection.
Figure 13:
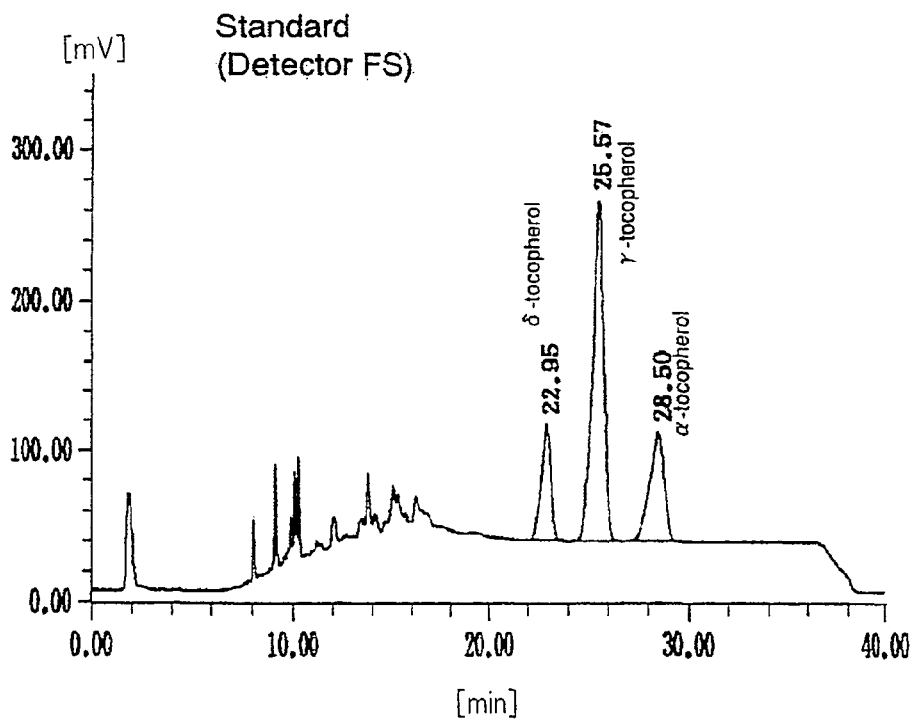
FIG. 13 shows the result of analysis of a vitamin E standard sample by a reverse phase chromatography and a fluorescent detection.
Figure 14:
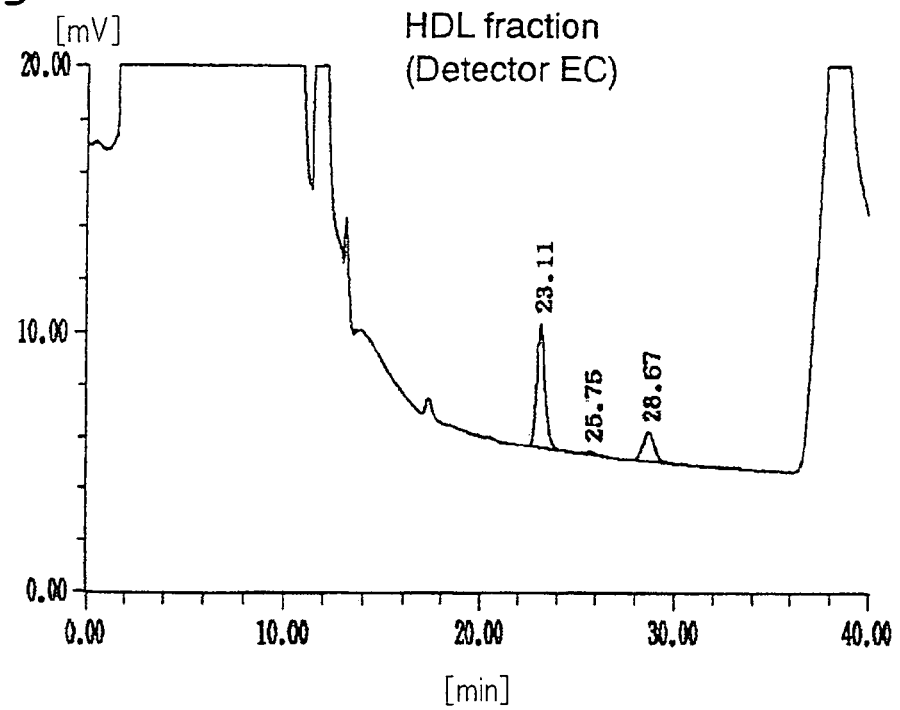
FIG. 14 shows the result of analysis of a HDL sample by a reverse phase chromatography and an electrochemical detection.
Figure 15:
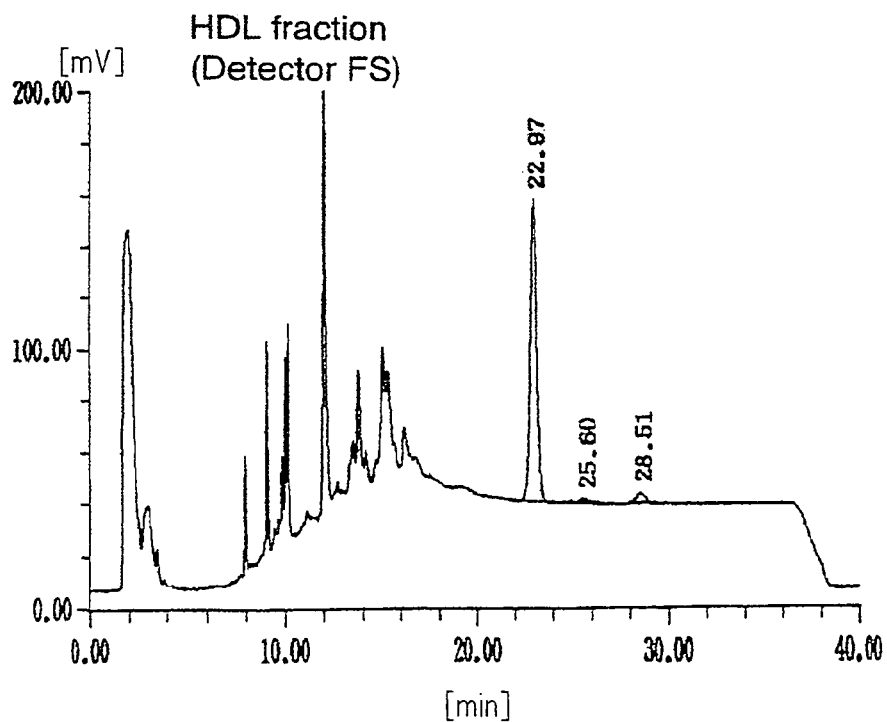
FIG. 15 shows the result of analysis of a HDL sample by a reverse phase chromatography and a fluorescent detection.
Figure 16:
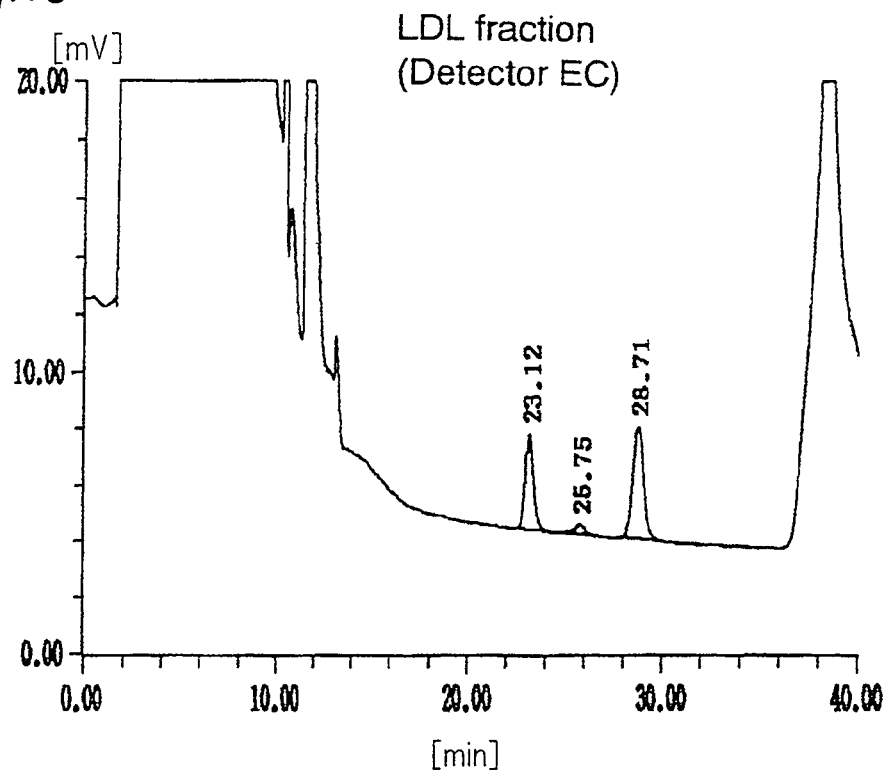
FIG. 16 shows the result of analysis of a LDL sample by a reverse phase chromatography and an electrochemical detection.
Figure 17:
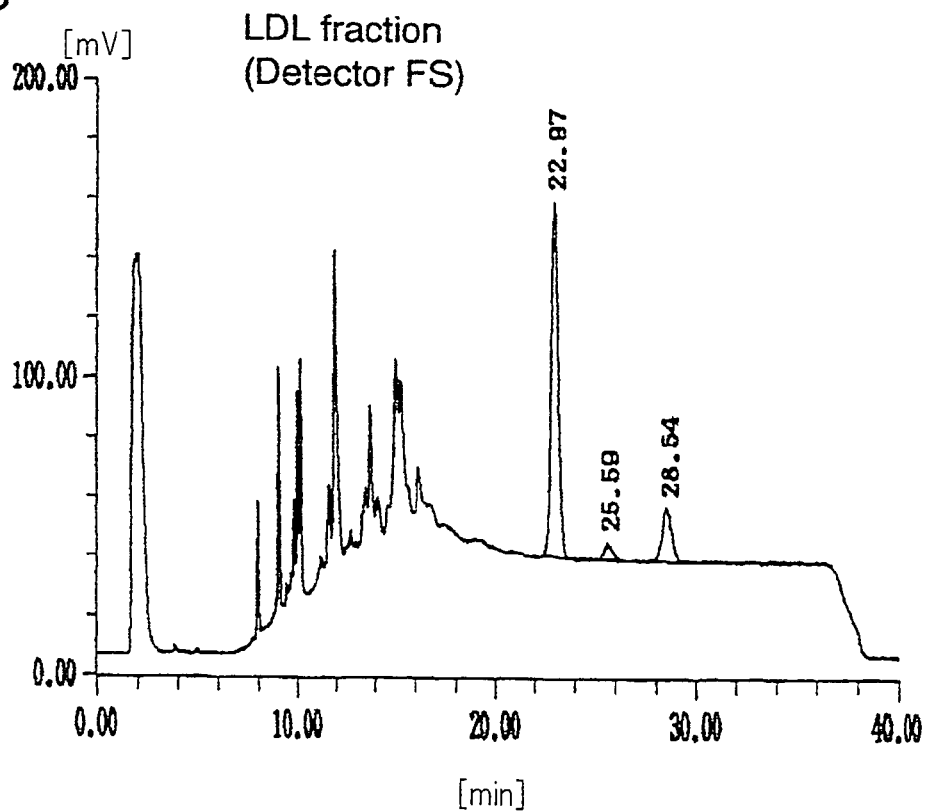
FIG. 17 shows the result of analysis of a LDL sample by a reverse phase chromatography and a fluorescent detection.
Figure 20:
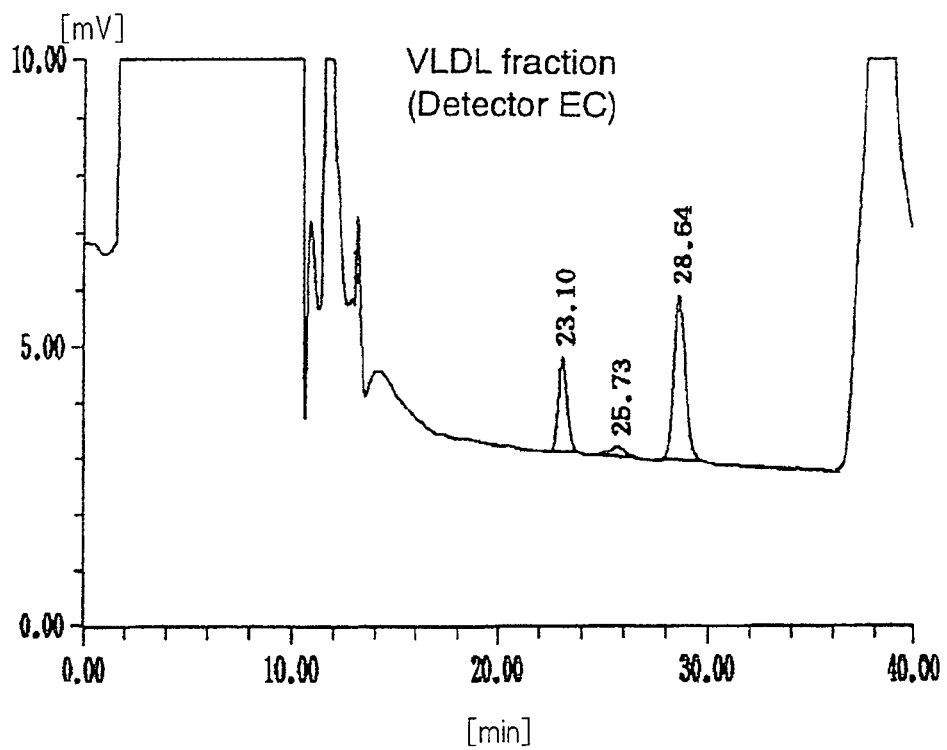
FIG. 20 shows the result of analysis of a VLDL sample by a reverse phase chromatography and an electrochemical detection.
Figure 21:
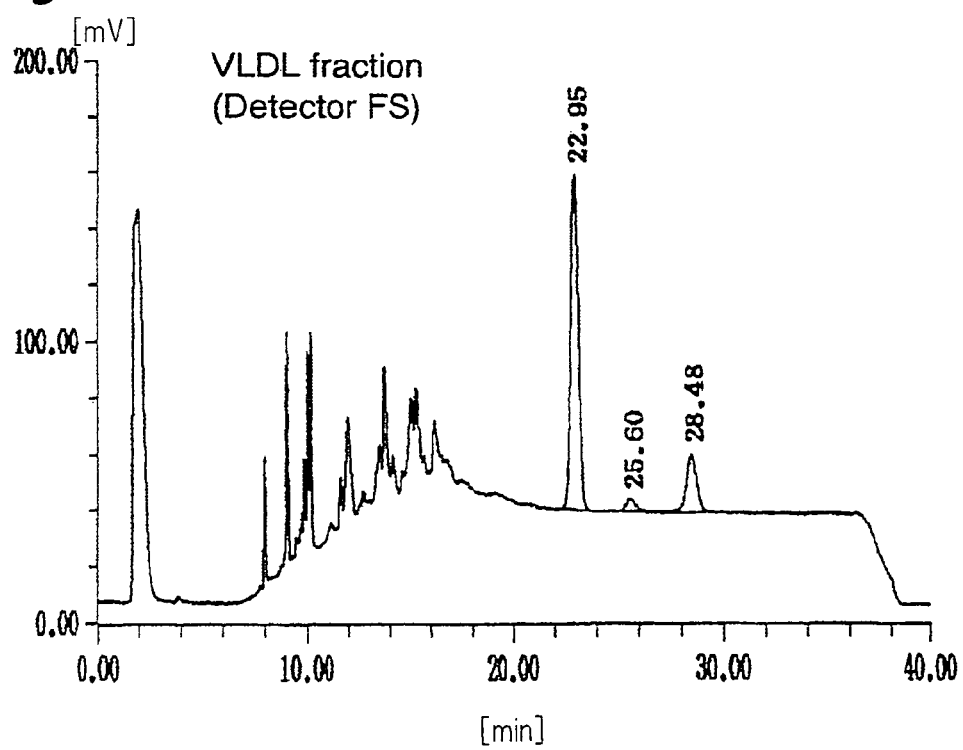
FIG. 21 shows the result of analysis of a VLDL sample by a reverse phase chromatography and a fluorescent detection.
Figure 22:
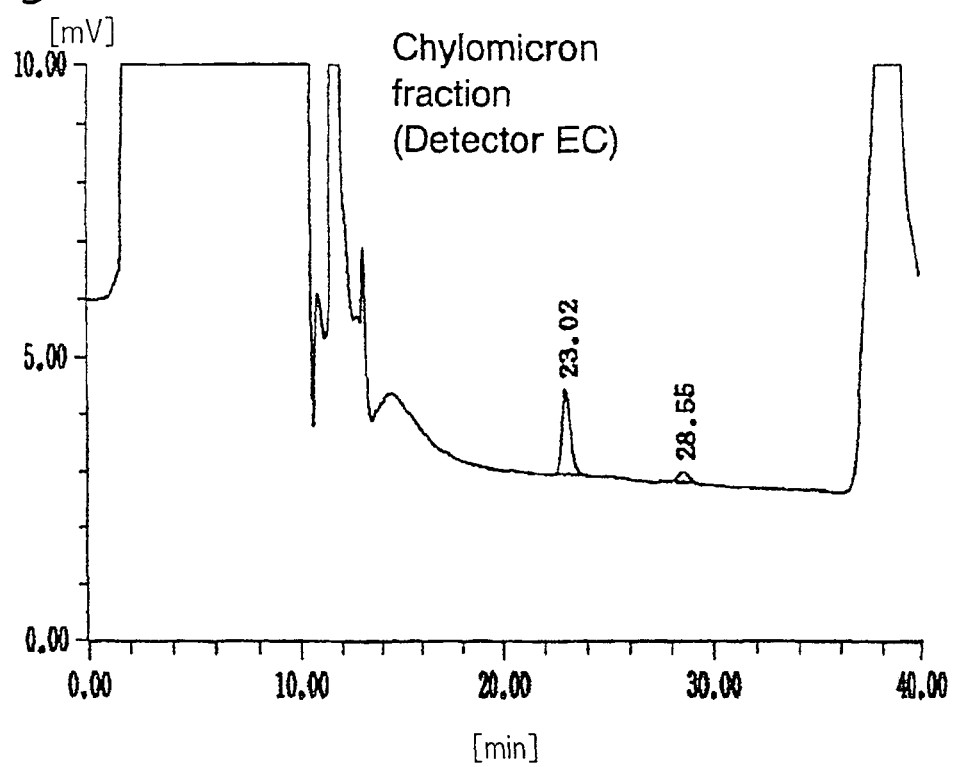
FIG. 22 shows the result of analysis of a CM sample by a reverse phase chromatography and an electrochemical detection.
Figure 23:
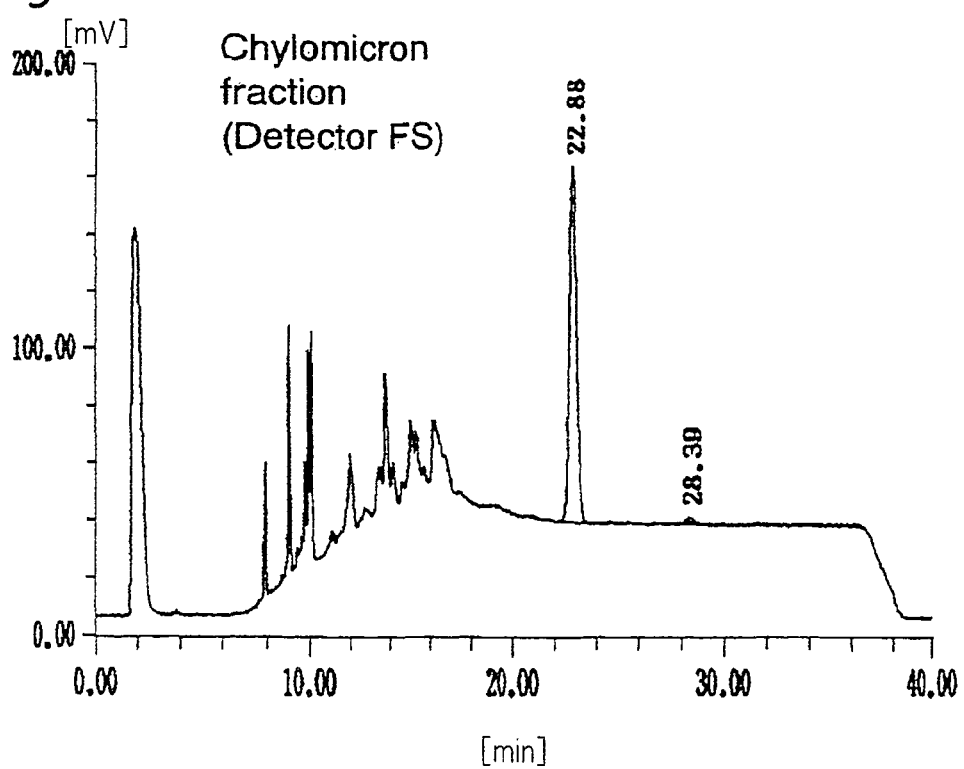
FIG. 23 shows the result of analysis of a CM sample by a reverse phase chromatography and a fluorescent detection.

20 μl of a serum (total cholesterol 242 mg/dL, triglyceride 421 mg/dL) collected after obtaining the informed consent from an individual who developed hyperlipidemia was subjected to the apparatus of Example 1, and each lipoprotein fraction eluted was collected as described below and the separation of the lipoprotein was tested.
HDL fraction: fractions from 0-8 minutes
LDL fraction: fractions from 8-13 minutes
IDL fraction: fractions from 13-19 minutes
VLDL fraction: fractions from 19-24 minutes
Chyromicron (hereinafter referred to as CM) fraction: fractions from 24-30 minutes To 500 μl of each lipoprotein fraction eluted, 500 μl of the pretreating solution (ethanol 50%, SDS 250 mmol/L, ascorbic acid 10 mmol/L, phosphoric acid 1%, δ-tocopherol 0.04 μg/mL) was added and mixed, which was subjected to the apparatus of Example 2 for the analysis of γ-tocopherol and α-tocopherol. However, behind the apparatus of Example 2, an amperometric electrochemical detector (voltage applied: 600 mV) was connected, and chromatograms were obtained with the two detectors. The results are shown in FIGS. 12 to 23 (odd numbers indicate the chromatograms by fluorescence detection, and even numbers indicate the chromatograms by electrochemical detection). FIGS. 12 and 13 are chromatograms for the standard sample (δ-tocopherol 0.02 μg/mL, γ-tocopherol 0.1 μg/mL, α-tocopherol 0.1 μg/mL) prepared using the pretreating solution diluted two-fold with pure water, from which it can be seen that δ-tocopherol, γ-tocopherol and α-tocopherol eluted in this order giving a favorable analytical result. FIGS. 14 and 15 indicate the chromatograms of the HDL fraction, FIGS. 16 and 17 indicate the chromatograms of the LDL fraction, FIGS. 18 and 19 indicate the chromatograms of the IDL fraction, FIGS. 20 and 21 indicate the chromatograms of the VLDL fraction, and FIGS. 22 and 23 indicate the chromatograms of the CM fraction. In the CM fraction, two peaks of δ-tocopherol and α-tocopherol, (δ-tocopherol is internal control), were detected but γ-tocopherol was not, and in the other fractions, all peaks of δ-tocopherol, δ-tocopherol and α-tocopherol were detected. From the peak height of the fluorescence detector, the concentrations of γ-tocopherol and α-tocopherol in each lipoprotein in the serum were calculated and shown in Table 6. In calculation, δ-tocopherol added to the pretreating solution was used as the internal control to calculate the recovery in each analysis to correct for the results of analysis, and dilution due to fraction separation and the pretreating solution have been taken into consideration. The concentrations of γ-tocopherol and α-tocopherol in the serum are the sum of concentrations in each lipoprotein fraction.

TABLE 6

|  | γ-tocopherol (μg/mL) | α-tocopherol (μg/mL) |
| --- | --- | --- |
| HDL | 0.21 | 1.57 |
| LDL | 0.39 | 3.96 |
| IDL | 0.25 | 3.00 |
| VLDL | 0.33 | 4.66 |
| Chylomicrons | 0.00 | 0.57 |
| Serum | 1.18 | 13.75 |

Example 4

20 μl of a serum (total cholesterol 203 mg/dL, triglyceride 215 mg/dL) collected after obtaining the informed consent from an individual who developed hyperlipidemia was subjected to the apparatus below (the apparatus construction is the same as that shown in FIG. 4, and the eluant composition and the elution condition were modified), and at an interval of 2 minutes from the introduction of the sample to 34 minutes, 17 samples were collected, and γ-tocopherol and α-tocopherol in each lipoprotein were analyzed by the apparatus and the method in Example 3. The cholesterol concentration for each fraction was determined using an enzyme solution containing cholesterol esterase and cholesterol oxidase (Cholesterol E test, trade name, manufactured by Wako Pure Chemical Industries, Ltd.).

Column 1 for the ion exchange chromatography: Two DEAE-NPRs (trade name, manufactured by TOSOH Corp.), 4.6 mm ID×35 mm, were connected in series.

Sample feeding part 2: AS-8020 (trade name, manufactured by TOSOH Corp.)

Mixing apparatus 3: Static mixer C (trade name, manufactured by TOSOH Corp.)

Liquid delivery pumps 4 and 5: DP-8020 (trade name, manufactured by TOSOH Corp.)

Eluant A: 50 mmol/L Tris+1 mmol/L EDTA 2Na+100 mmol/L sodium thiocyanate, pH 7.5

Eluant B: 50 mmol/L Tris+1 mmol/L EDTA 2Na+100 mmol/L sodium thiocyanate+500 mmol/L sodium nitrate, pH 7.5

Flow rate of the ion exchange chromatography: 0.5 ml/min

Elution condition of the ion exchange chromatography:

0 minute to 24 minutes

Linear gradient from Eluant B 10%, eluant A 90% to Eluant B 50%, eluant A 50%

20 minutes to 25 minutes

Eluant B 50%, eluant A 50%

25 minutes to 30 minutes

Eluant B 100%, eluant A 0%

30 minutes to 40 minutes

Eluant B 10%, eluant A 90%

The concentrations of γ-tocopherol, α-tocopherol and cholesterol in each eluted fraction are shown in Table 7. Fractions 6 and 7 correspond to HDL, fractions 8 and 9 correspond to LDL, fractions 10 and 11 correspond to IDL, fractions 12 and 13 correspond to VLDL, and fractions 13 and 14 correspond to CM. Thus, even when lipoprotein was eluted in a liner gradient manner in the ion exchange chromatography, the favorable analysis of vitamin E components in the lipoprotein was attained.

TABLE 7

| Fraction No. | Tocopherol (ng/ml) | | Cholesterol (mg/dl) |
| --- | --- | --- | --- |
|  | γ | α |  |
| 1 | 0.00 | 0.00 | 1.6 |
| 2 | 0.00 | 0.42 | 0.8 |
| 3 | 0.00 | 0.00 | 0.8 |
| 4 | 0.00 | 0.10 | 0.0 |
| 5 | 0.00 | 0.53 | 0.8 |
| 6 | 0.00 | 2.45 | 4.0 |
| 7 | 0.59 | 8.54 | 16.0 |
| 8 | 2.84 | 29.90 | 71.2 |
| 9 | 1.83 | 21.69 | 44.8 |
| 10 | 0.71 | 10.68 | 16.0 |
| 11 | 0.69 | 13.33 | 16.0 |
| 12 | 1.37 | 20.58 | 21.6 |
| 13 | 0.79 | 14.14 | 12.8 |
| 14 | 0.00 | 7.41 | 5.6 |
| 15 | 0.00 | 8.30 | 7.2 |
| 16 | 0.00 | 1.48 | 0.0 |
| 17 | 0.00 | 0.77 | 0.0 |

Example 5

As the analytical apparatus of the present invention shown in FIG. 1, specifically the following apparatus was constructed. 20 μl of a serum (total cholesterol 203 mg/dL, triglyceride 215 mg/dL) collected after obtaining the informed consent from an individual who developed hyperlipidemia was subjected to this apparatus to analyze vitamin Es. In this example, instead of determining vitamin E components in each lipoprotein by the one time introduction of the sample, but by introducing the sample for a total of five times, vitamin E components in each lipoprotein was analyzed.

Column 1 for the ion exchange chromatography: Two DEAE-NPR columns (trade name, manufactured by TOSOH Corp.), 4.6 mm ID×35 mm, were connected in series.

Sample feeding part 2: AS-8020 (trade name, manufactured by TOSOH Corp.)

Mixing apparatus 3: Static mixer C (trade name, manufactured by TOSOH Corp.)

Liquid delivery pumps 4 and 5: DP-8020 (trade name, manufactured by TOSOH Corp.)

Eluant A6: 50 mmol/L Tris+1 mmol/L EDTA 2Na, pH 7.5

Eluant B7: 50 mmol/L Tris+1 mmol/L EDTA 2Na+sodium perchlorate 300 mmol/L, pH 7.5

Flow rate of the ion exchange chromatography: 0.5 ml/min

Elution condition of the ion exchange chromatography:

0 minute to 0.05 minute

Eluant B 10%, eluant A 90%

0.05 minute to 5 minutes

Eluant B 38%, eluant A 62%

5 minutes to 11 minutes

Eluant B 44%, eluant A 56%

11 minutes to 16 minutes

Eluant B 49%, eluant A 51%

16 minutes to 21 minutes

Eluant B 56%, eluant A 44%

21 minutes to 29 minutes

Eluant B 100%, eluant A 0%

29 minutes to 40 minutes

Eluant B 10%, eluant A 90%

Liquid delivery pump 8: DP-8020 (trade name, manufactured by TOSOH Corp.)

Pretreating solution 9: 100 mmol/L SDS+50% ethanol

Mixing apparatus 10: Static mixer B (trade name, manufactured by TOSOH Corp.)

Figure 24:
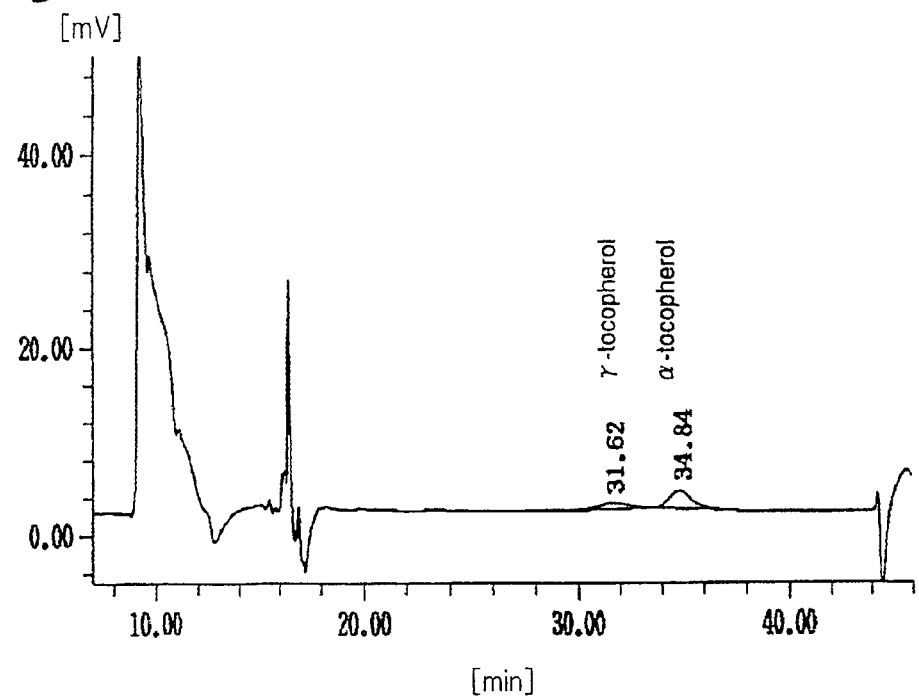
FIG. 24 shows the result of analysis of vitamin E in HDL by an electrochemical detection.
Figure 25:
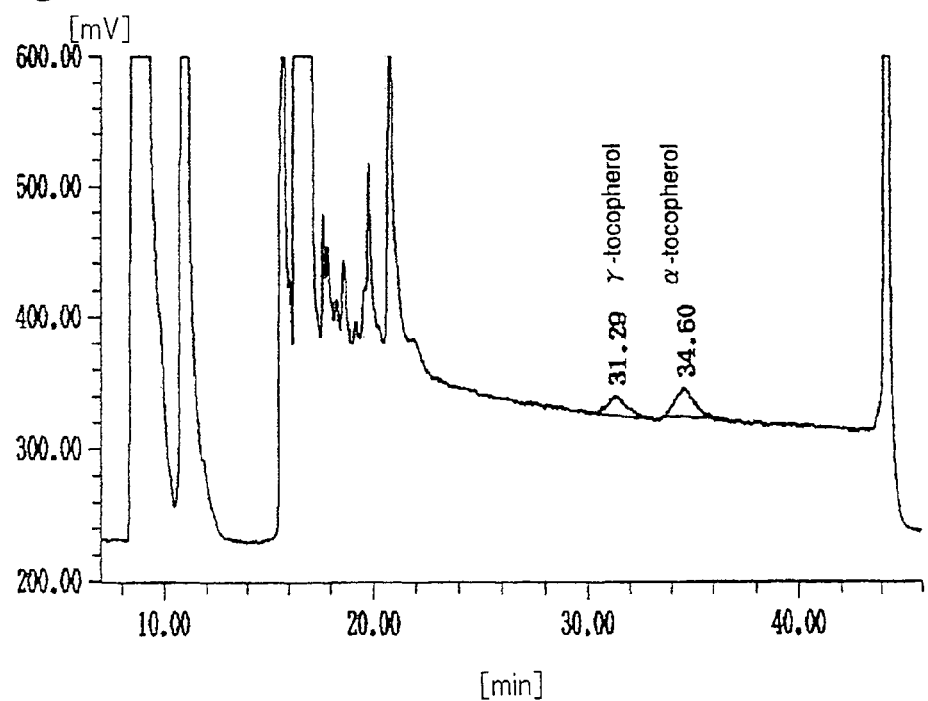
FIG. 25 shows the result of analysis of vitamin E in HDL by a fluorescent detection.
Figure 26:
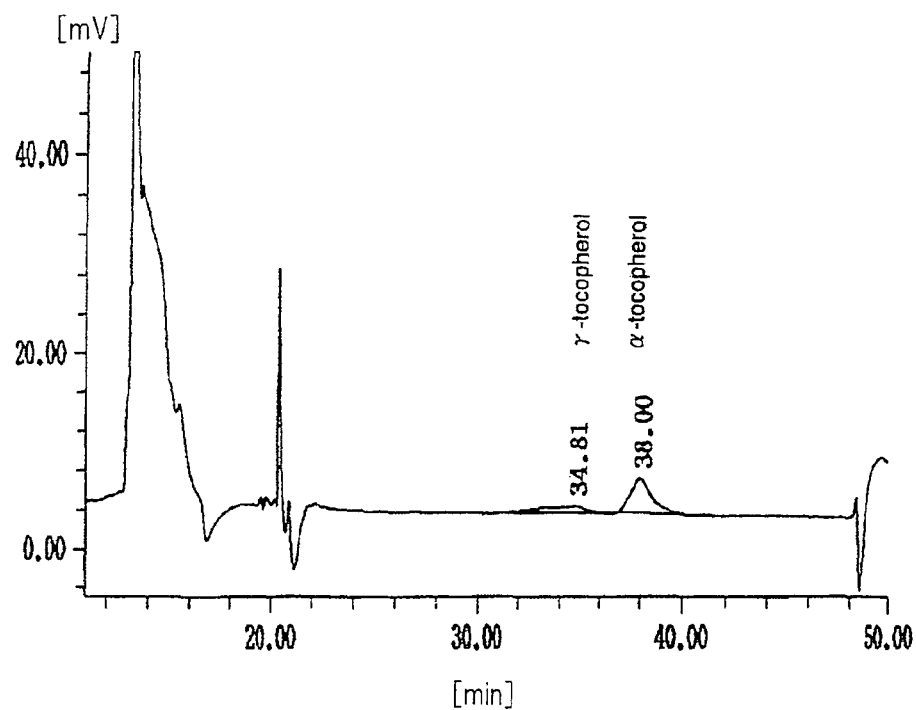
FIG. 26 shows the result of analysis of vitamin E in LDL by an electrochemical detection.
Figure 27:
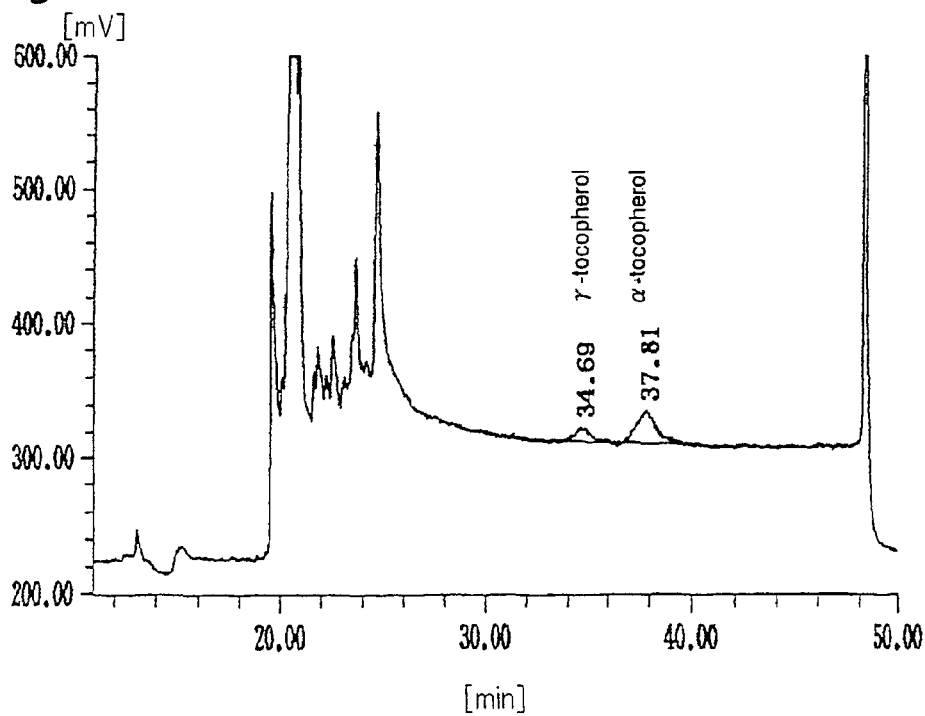
FIG. 27 shows the result of analysis of vitamin E in LDL by a fluorescent detection.
Figure 28:
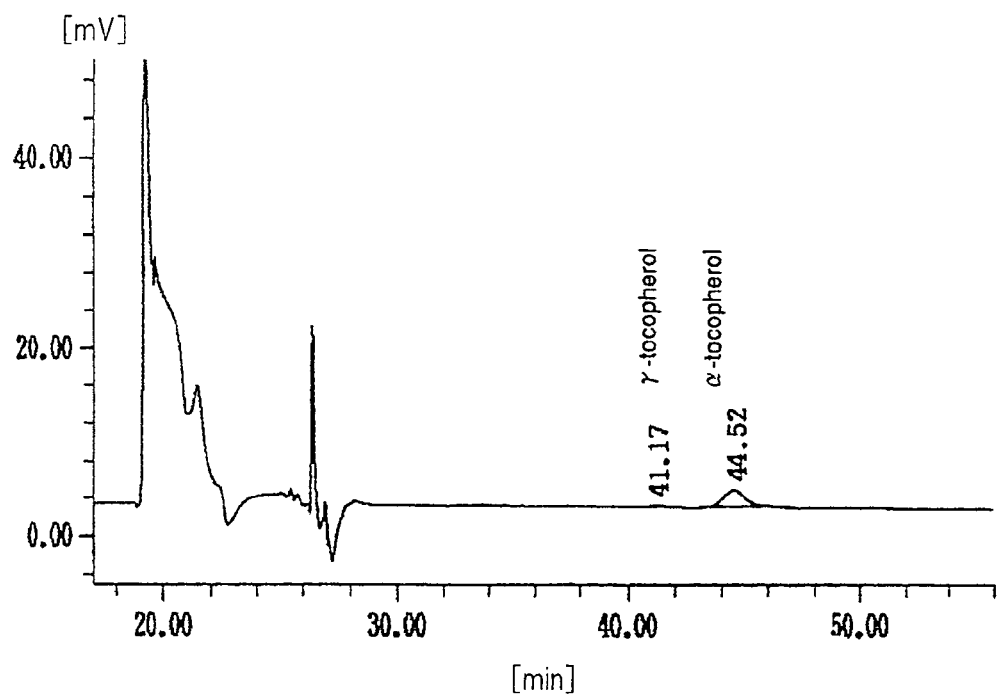
FIG. 28 shows the result of analysis of vitamin E in IDL by an electrochemical detection.
Figure 29:
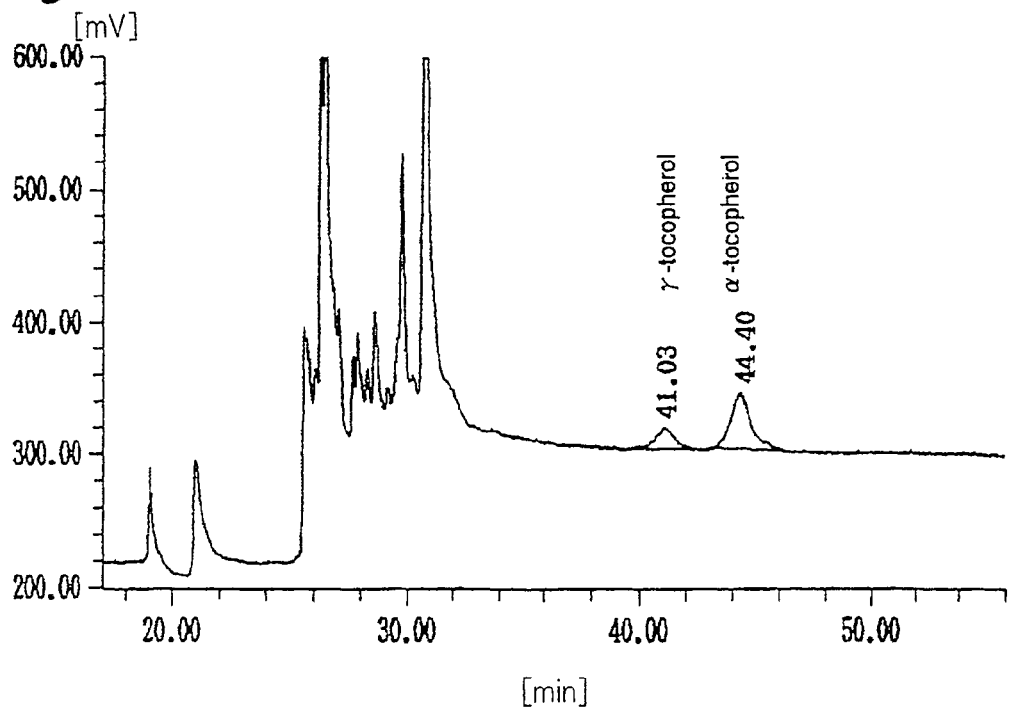
FIG. 29 shows the result of analysis of vitamin E in IDL by a fluorescent detection.
Figure 30:
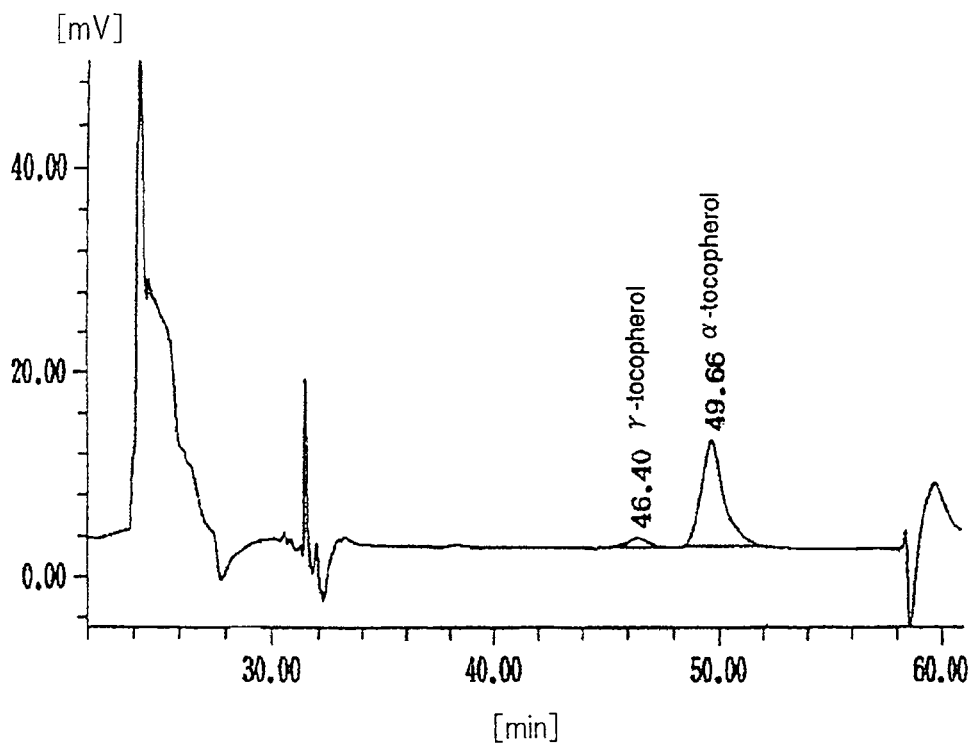
FIG. 30 shows the result of analysis of vitamin E in VLDL by an electrochemical detection.
Figure 31:
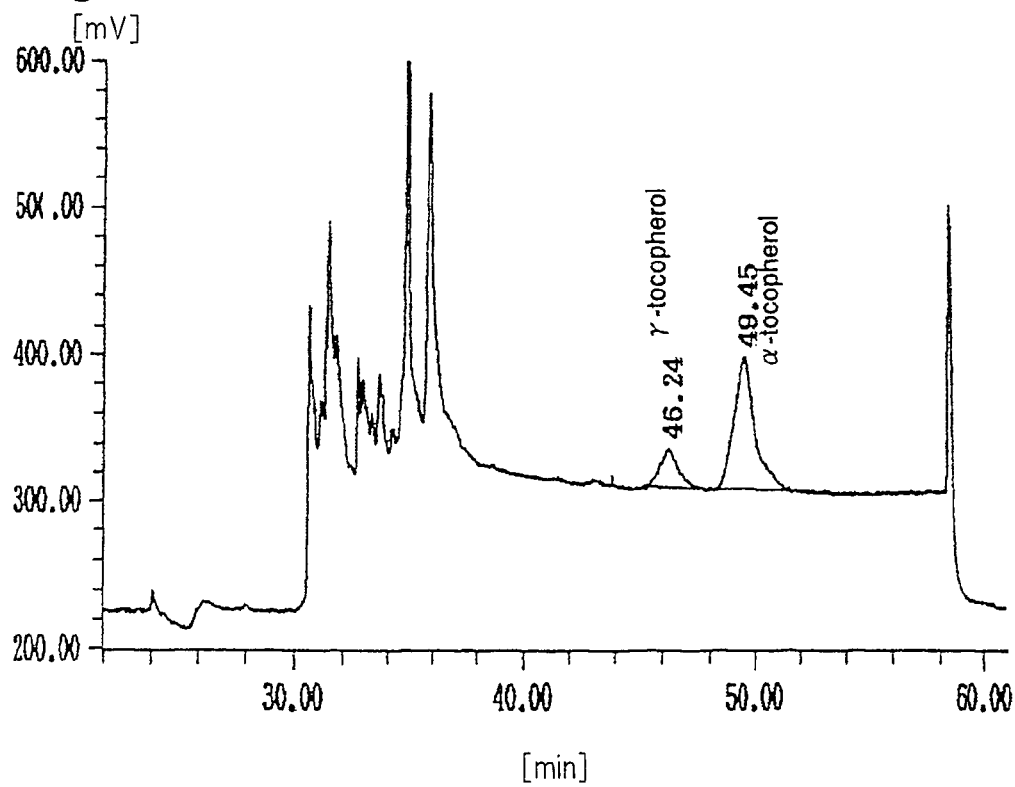
FIG. 31 shows the result of analysis of vitamin E in VLDL by a fluorescent detection.
Figure 32:
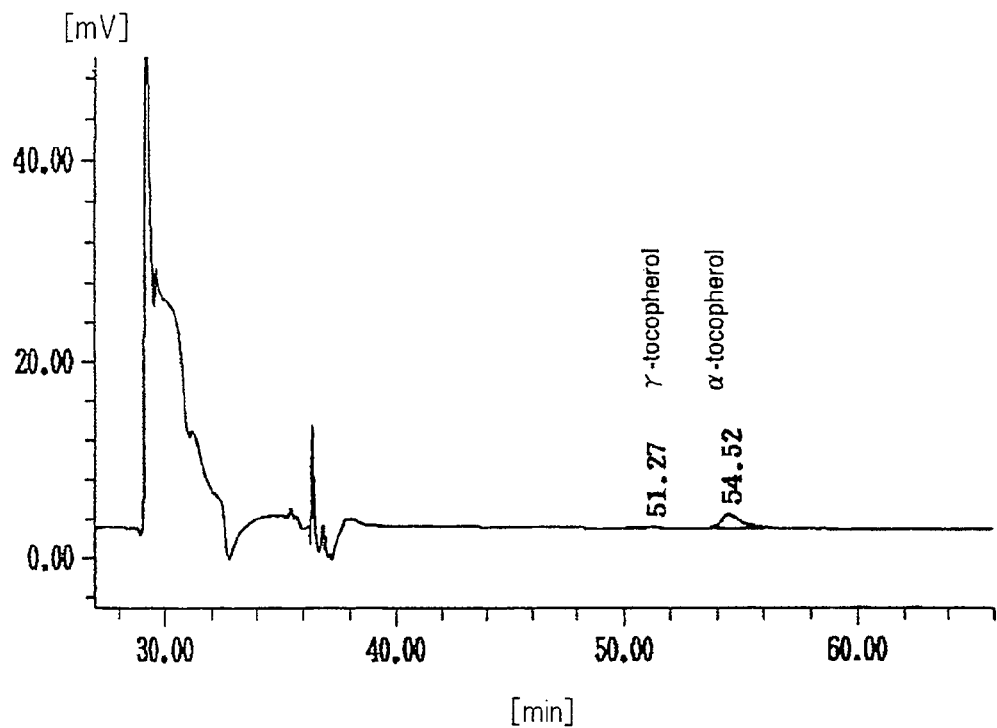
FIG. 32 shows the result of analysis of vitamin E in CM by an electrochemical detection.
Figure 33:
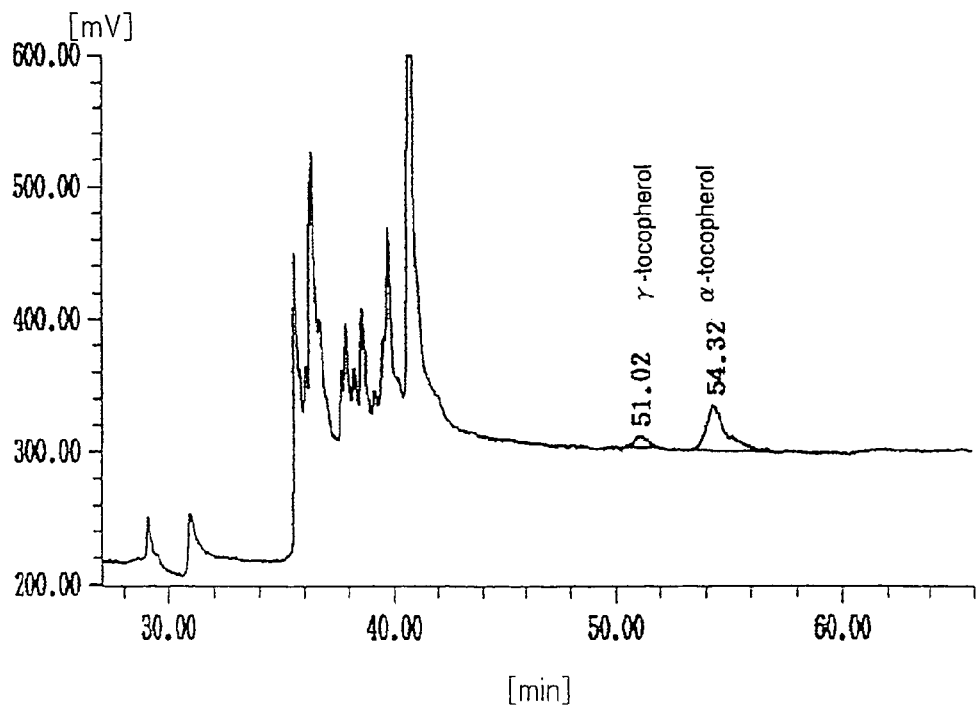
FIG. 33 shows the result of analysis of vitamin E in CM by a fluorescent detection.

Flow rate of the pretreating solution: 0.25 ml/min
Six-way switch valve 11: Six-way electromagnetic valve
Timing of switching (switching of the flow path from OFF to ON)
For HDL elution fraction, for 2 minutes from 7 minutes
For LDL elution fraction, for 2 minutes from 11 minutes
For IDL elution fraction, for 2 minutes from 17 minutes
For VLDL elution fraction, for 2 minutes from 22 minutes
For CM elution fraction, for 2 minutes from 27 minutes
Volume of the sample loop 12: 1.5 ml volume
Column 13 for the reverse phase chromatography: ODS-80Ts (trade name, manufactured by TOSOH Corp.), 4.6 mm ID×150 mm
Detector 14: FS-8020 (trade name, a fluorescence detector manufactured by TOSOH Corp., excitation wavelength 298 nm, emission wavelength 325 nm).
Detector 15: EC-8020 (trade name, a amperometric electrochemical detector manufactured by TOSOH Corp., applied voltage 600 mV).
Liquid delivery pumps 16 and 17: DP-8020 (trade name, manufactured by TOSOH Corp.)
Eluant C18: 30% ethanol+25 mmol/L ammonium nitrate
Eluant C19: 85% ethanol+25 mmol/L ammonium nitrate
Flow rate of the reverse phase chromatography: 1.0 ml/min
Elution condition of the reverse phase chromatography:
Initially, eluant C 100%, D 0%
Five minutes after the switch valve 11 turned ON, change to eluant C 100%, D 0%
34 minutes after the switch valve 11 turned ON, change to eluant C 0%, D 100%
Time required for analysis: 46 minutes/sample The results of analysis of the HDL elution fraction are shown in FIGS. 24 and 25, those of the LDL elution fraction are shown in FIGS. 26 and 27, those of the IDL elution fraction are shown in FIGS. 28 and 29, those of the VLDL elution fraction are shown in FIGS. 30 and 31, and those of the CM elution fraction are shown in FIGS. 32 and 33. In each figure, even numbers indicate the chromatograms by electrochemical detection and odd numbers indicate the chromatograms by fluorescence detection. As can be seen from each figure, γ-tocopherol and α-tocopherol were successfully detected for each lipoprotein fraction.

Example 6

Figure 34:
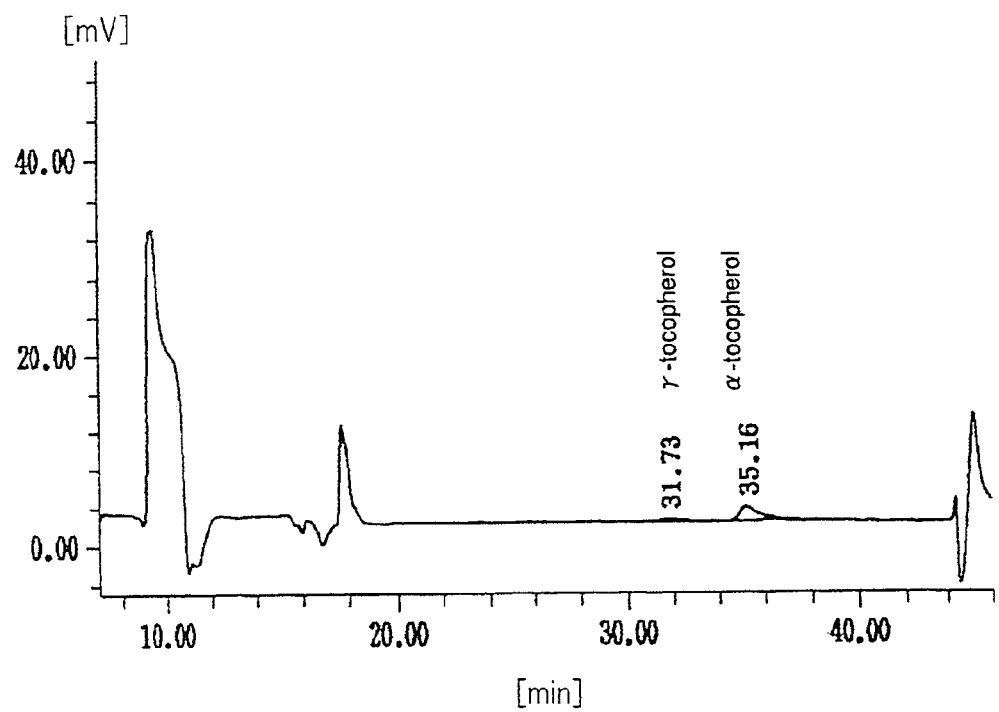
FIG. 34 shows the result of analysis of vitamin E in HDL by an electrochemical detection.
Figure 35:
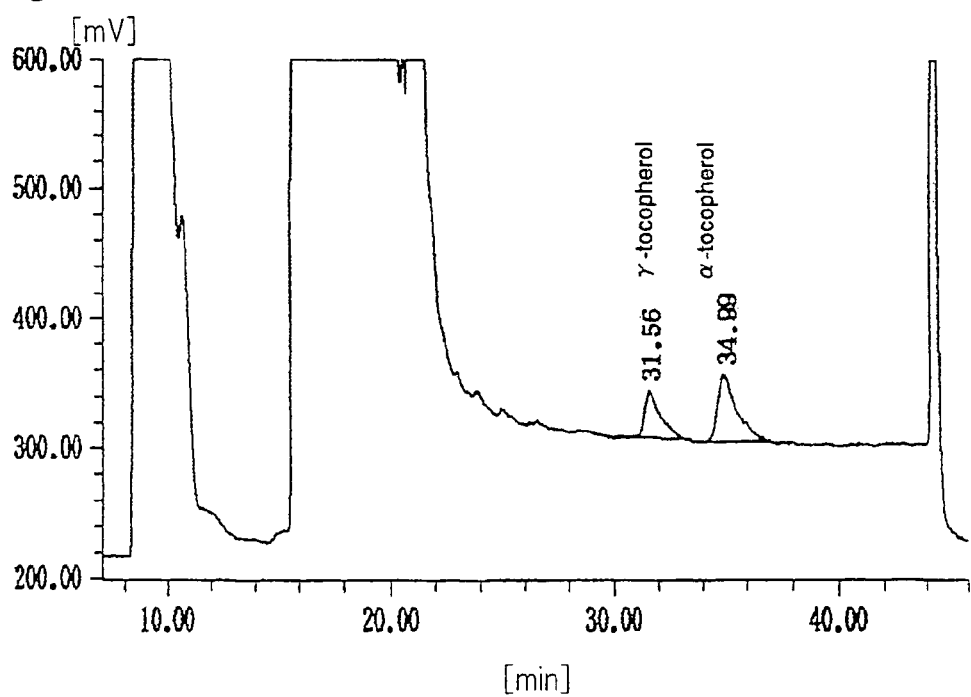
FIG. 35 shows the result of analysis of vitamin E in HDL by a fluorescent detection.
Figure 36:
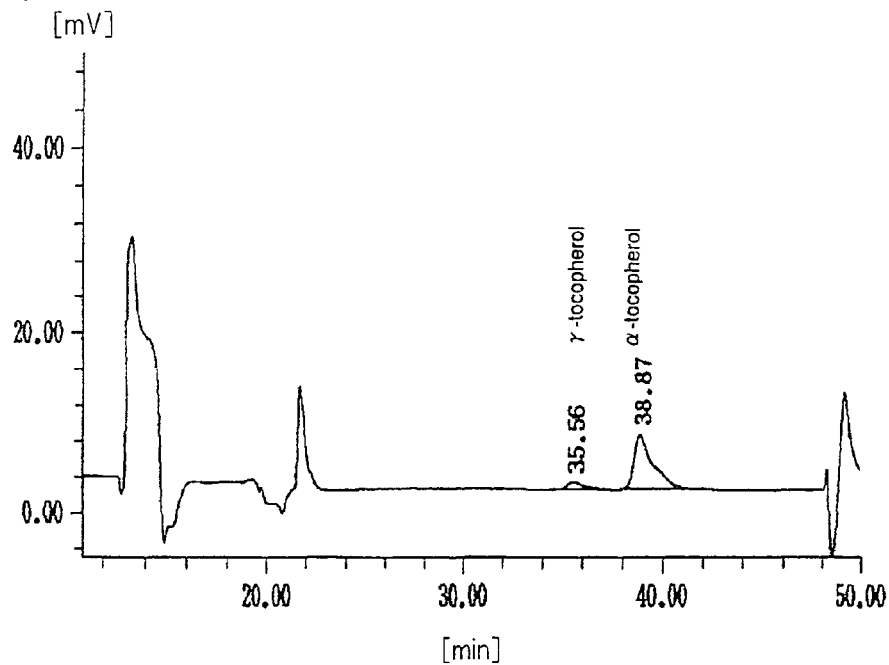
FIG. 36 shows the result of analysis of vitamin E in LDL by an electrochemical detection.
Figure 37:
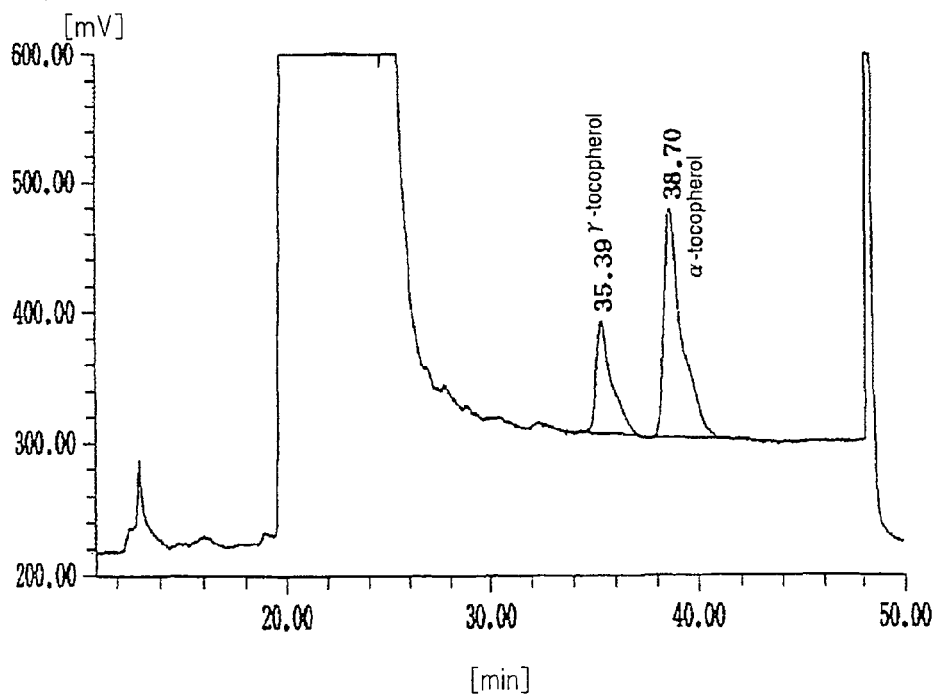
FIG. 37 shows the result of analysis of vitamin E in LDL by a fluorescent detection.
Figure 38:
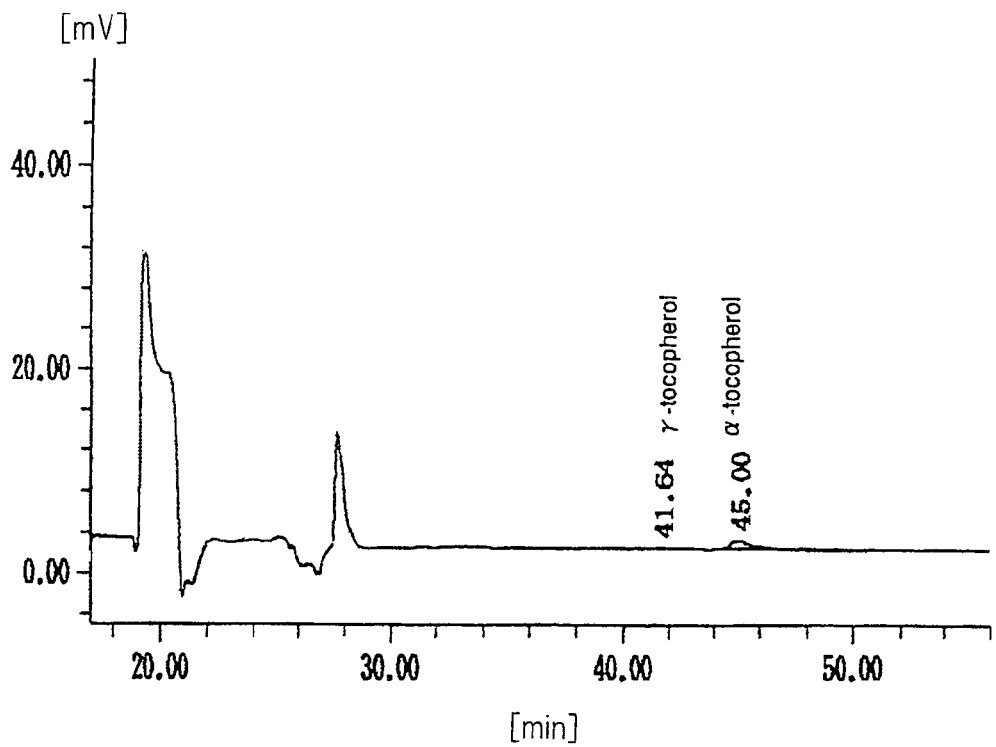
FIG. 38 shows the result of analysis of vitamin E in IDL by an electrochemical detection.
Figure 39:
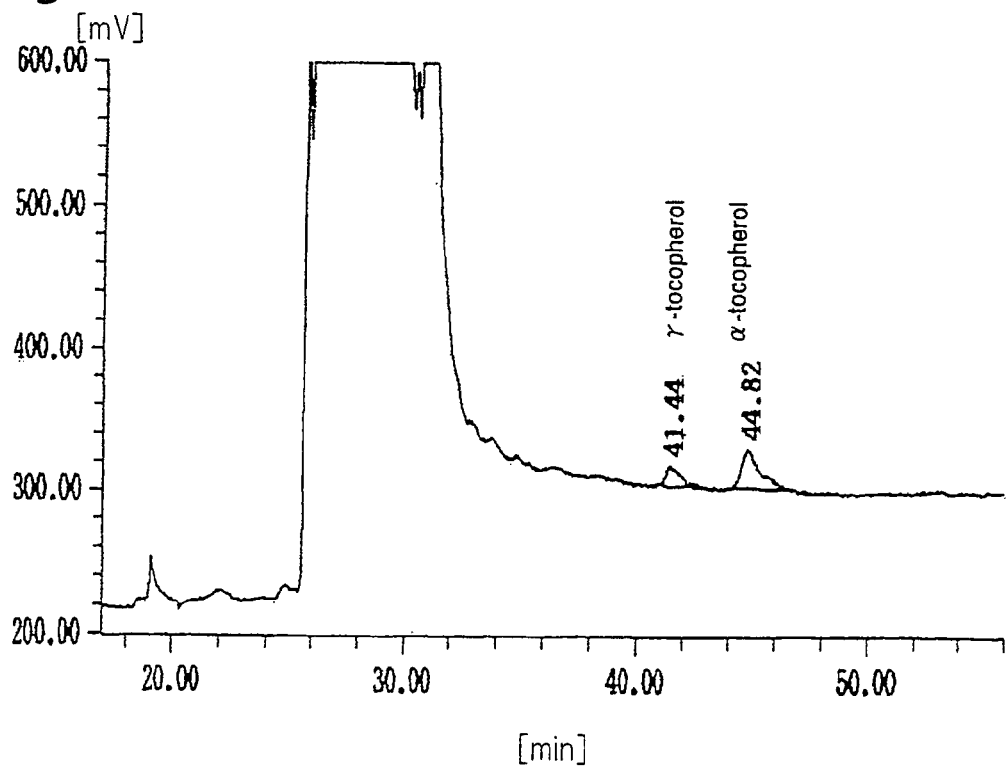
FIG. 39 shows the result of analysis of vitamin E in IDL by a fluorescent detection.
Figure 40:
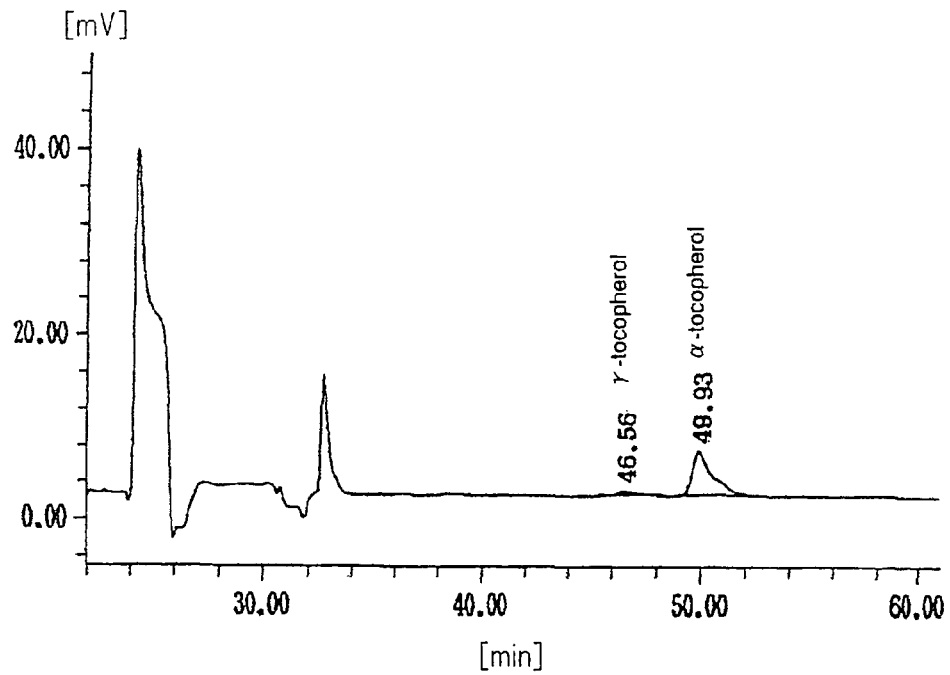
FIG. 40 shows the result of analysis of vitamin E in VLDL by an electrochemical detection.
Figure 41:
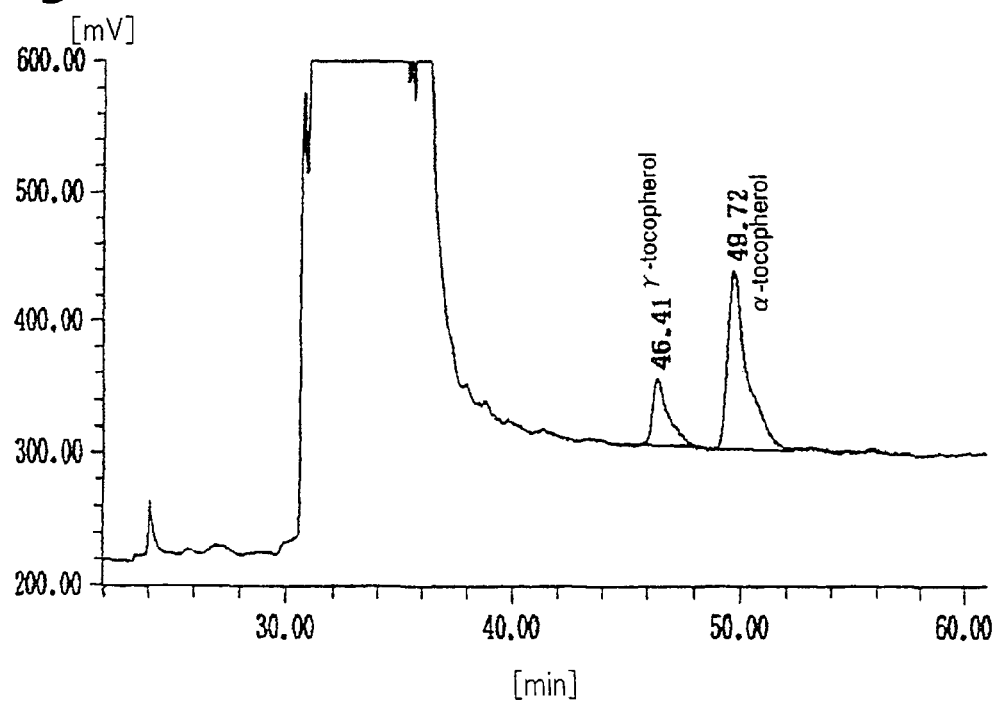
FIG. 41 shows the result of analysis of vitamin E in VLDL by a fluorescent detection.
Figure 42:
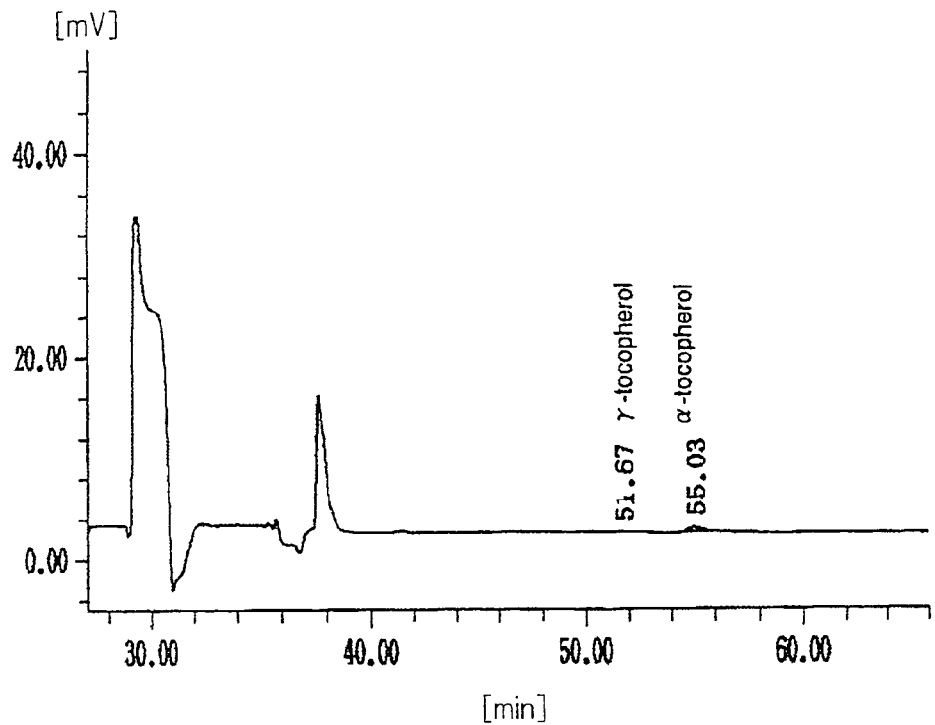
FIG. 42 shows the result of analysis of vitamin E in CM by an electrochemical detection.
Figure 43:
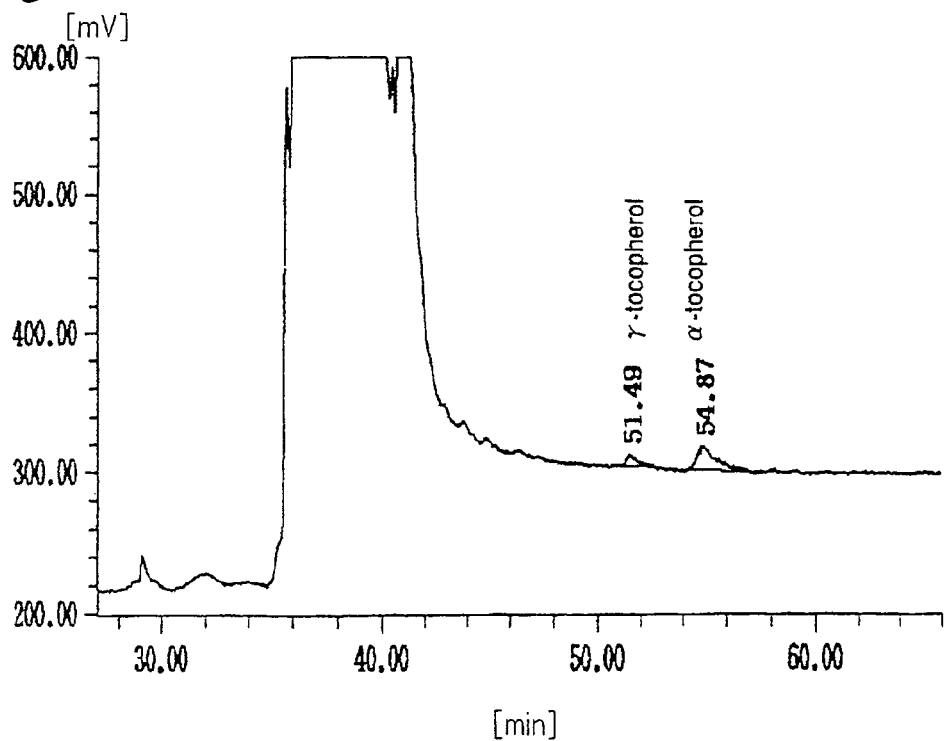
FIG. 43 shows the result of analysis of vitamin E in CM by a fluorescent detection.

Except that the composition of the pretreating solution was 50 mmol/L sodium perchlorate+1% Triton X100+75% ethanol, the same apparatus and the method as that of Example 5 were used to carry out the analysis. The results of analysis of the HDL elution fraction are shown in FIGS. 34 and 35, those of the LDL elution fraction are shown in FIGS. 36 and 37, those of the IDL elution fraction are shown in FIGS. 38 and 39, those of the VLDL elution fraction are shown in FIGS. 40 and 41, and those of the CM elution fraction are shown in FIGS. 42 and 43. In each figure, even numbers indicate the chromatograms by electrochemical detection and odd numbers indicate the chromatograms by fluorescence detection. As can be seen from each figure, γ-tocopherol and α-tocopherol were successfully detected for each lipoprotein fraction.

As a risk factor for arteriosclerosis, oxidized lipoprotein is attracting much attention. A major antioxidant contained in the lipoprotein is vitamin E (mainly α-tocopherol and γ-tocopherol), and the analytical method of the present invention for vitamin E in the lipoprotein can analyze the amount of vitamin E in each lipoprotein in the blood, and thus will be able to obtain important finding in understanding the mechanism of arteriosclerosis. If the relationship between arteriosclerosis and vitamin E in the lipoprotein were elucidated, the analytical method of the present invention would be preferred for the diagnosis of arteriosclerosis and monitoring of therapeutic effect.

The analytical apparatus of the present invention can analyze vitamin E etc. automatically and thus in a short period of time, and besides being an automatic analysis, there is very little chance of generating errors.

Compared to the constitution in the prior art that after separating each lipoprotein, vitamin E components are extracted, concentrated to dryness, redissolved, and subjected to a reverse phase chromatography, the constitution that after separating each lipoprotein using an ion exchange chromatography, the separated lipoprotein is reacted with a pretreating solution containing an organic solvent and a surfactant thereby to liberate vitamin E components, and the liberated vitamin E components are subjected to a reverse phase chromatography is a simple constitution per se and is characterized by a little chance of generating errors. Specifically, the prior art comprised complicated and error-prone manual works that for each lipoprotein fraction vitamin E components were manually extracted, concentrated to dryness, and redissolved, but in the present invention, these steps have been replaced with a simple step of adding and mixing and reacting the previously prepared pretreating solution.

The prior art comprised the complicated steps, which require manual works of extraction of vitamin E components, concentration to dryness and redissolution, and thus the automatization of the procedure was difficult. In the analysis of the present invention, however, the separating agent used in the ion exchange chromatography and the reverse phase chromatography can be loaded in columns for performing the analysis, and thus the step of mixing the pretreating solution to the eluted solution from the ion exchange chromatography replacing the steps of extraction of vitamin E components, concentration to dryness and redissolution can be automated in a process in which the eluted solution of the ion exchange chromatography is subjected to the reverse phase chromatography. As a result, the analytical method of the present invention can be easily automated by an analytical apparatus comprising a sample feeding part for collecting a given amount of a sample, an ion exchange chromatography part equipped with an ion exchange column, a reagent mixing part for mixing part or all of the eluted solution from the ion exchange chromatography part with the reagent, a reverse phase chromatography part equipped with a reverse phase column, a detection part for carrying out detection on the eluted solution from the reverse phase chromatography part, and a liquid delivery part for delivering the sample collected at the sample feeding part and the eluant for the ion exchange chromatography, a liquid delivery part for delivering the reagent, and a liquid delivery part for delivering the mixture of the eluted solution from the ion exchange chromatography part and the reagent, and a liquid delivery part for delivering the eluant for the reverse phase chromatography, and thus the analysis time and efforts can be curtailed.

Example 7

α-tocopherol and γ-tocopherol in the HDL, LDL, IDL, VLDL, chylomicron in the sera of 17 healthy individuals (Healthy), 20 patients with diabetes (Diabetes) and 17 patients with myocardial infarction (AMI) were determined by the method described in Example 3. Also, using the ion exchange chromatography method (Hirowatari Y. et al., J. Lipid Res. 44: 1404 (2003)), cholesterol in each lipoprotein was separately determined, and α-tocopherol and γ-tocopherol per cholesterol were calculated.

By summing up α-tocopherol or γ-tocopherol in all lipoproteins, the total vitamin E concentration (a-tocopherol or γ-tocopherol concentrations) in all lipoproteins in the blood was calculated. And separately, cholesterol in each lipoprotein was determined, and summed up to calculate cholesterol in the blood, and α-tocopherol and γ-tocopherol per cholesterol were calculated. The results are shown in figures and tables. In the figures, the bar and the square indicate the center value (50 percentile) and 25-75 percentile (IQR) in a non-parametric statistics.

Figure 44:
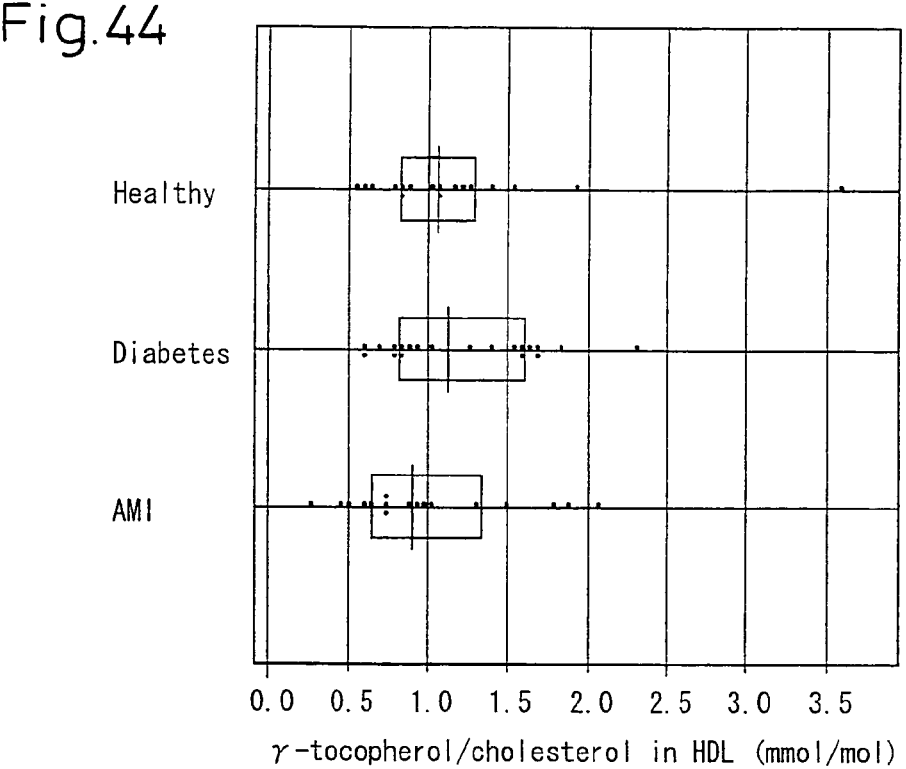
FIG. 44 shows the γ-tocopherol/cholesterol value in HDL.

The γ-tocopherol/cholesterol values (γ-tocopherol value per cholesterol) in the HDL are shown in FIG. 44 and Table 8.

TABLE 8

| | | γ-tocopherol/cholesterol | | | | | |
|---|---|---|---|---|---|---|---|
| | | HDL mmol/mol | LDL mmol/mol | IDL mmol/mol | VLDL mmol/mol | CM mmol/mol | Serum mmol/mol |
| Diabetes | Mean | 1.23 | 0.40 | 3.17 | 2.39 | 11.04 | 0.90 |
| | SD | 0.49 | 0.20 | 1.64 | 2.43 | 5.31 | 0.28 |
| AMI | Mean | 1.00 | 0.37 | 4.82 | 6.91 | 15.71 | 0.97 |
| | SD | 0.53 | 0.15 | 2.49 | 6.16 | 9.39 | 0.31 |
| Healthy | Mean | 1.20 | 0.34 | 6.25 | 5.05 | 17.42 | 1.03 |
| | SD | 0.72 | 0.15 | 3.96 | 3.76 | 11.49 | 0.30 |
| Significant test, Nonparametric | Healthy vs Diabetes | 0.897 | 0.269 | 0.007 | 0.018 | 0.047 | 0.199 |
| | Healthy vs AMI | 0.364 | 0.532 | 0.218 | 0.299 | 0.637 | 0.584 |

Diabetes (mean value: 1.23 mmol/mol), myocardial infarction (mean value: 1.00 mmol/mol) and the healthy individuals (mean value: 1.20 mmol/mol) exhibited similar values, but some patients with myocardial infarction exhibited values as low as 0.5 mmol/mol or less, which is obviously low compared to the healthy individuals. The presence of myocardial infarction patients with low values compared to the healthy individuals is thought to indicate that γ-tocopherol in the HDL was decomposed by oxidative stress.

Figure 45:
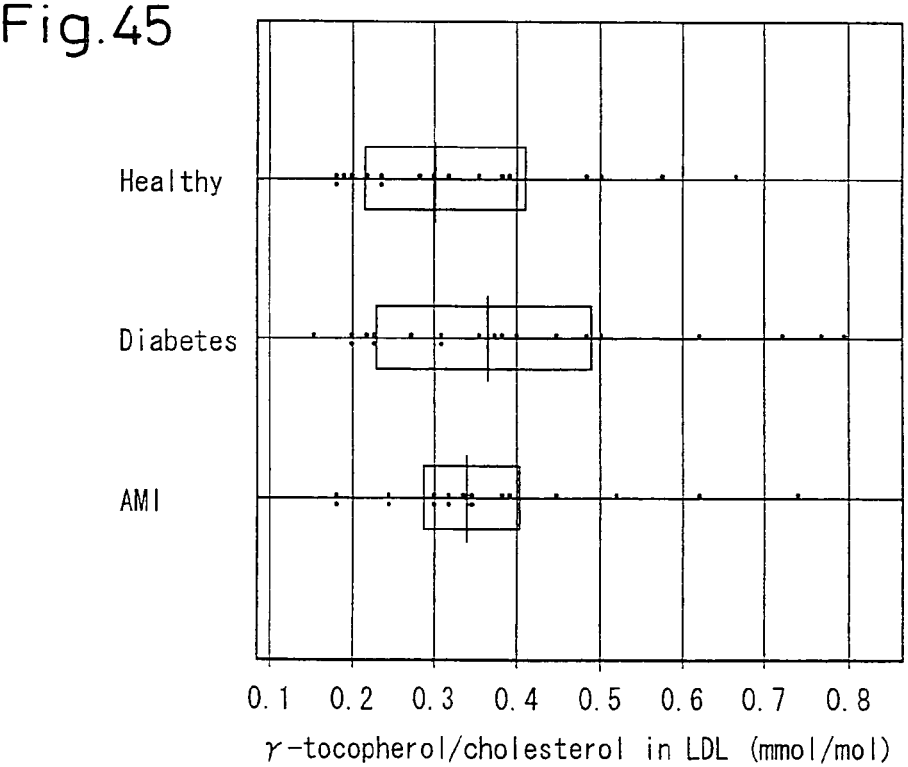
FIG. 45 shows the γ-tocopherol/cholesterol value in LDL.

The γ-tocopherol/cholesterol values in the LDL are shown in FIG. 45 and Table 8. Diabetes (mean value: 0.40 mmol/mol), myocardial infarction (mean value: 0.37 mmol/mol) and the healthy individuals (mean value: 0.34 mmol/mol) exhibited similar values.

Figure 46:
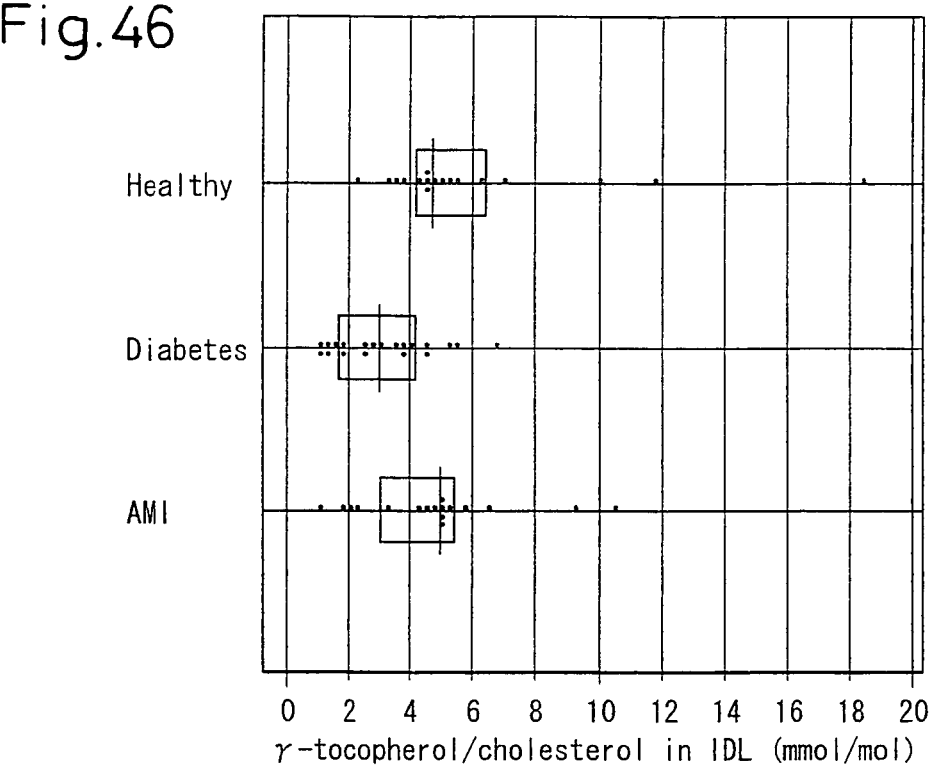
FIG. 46 shows the γ-tocopherol/cholesterol value in IDL.

The γ-tocopherol/cholesterol values in the IDL are shown in FIG. 46 and Table 8. Diabetes (mean value: 3.17 mmol/mol) was significantly (p=0.007) lower than the healthy individuals (mean value: 6.25 mmol/mol), indicating that γ-tocopherol in the IDL was decomposed by oxidative stress, a pathological condition carried by diabetes. In myocardial infarction as well, though there were no significant difference (p=0.218), the mean value of 4.82 mmol/mol was lower than the healthy individuals, which is also due to oxidative stress. Criteria for judgment of significant difference is that: between the values of the healthy individuals and those of patients, a Welch's t test (t test intended for two samples with unequal variance) is performed, and when the p-value is less than 0.05 it was judged to be significantly different, and otherwise judged to be no significant difference (the same hereinafter).

Figure 47:
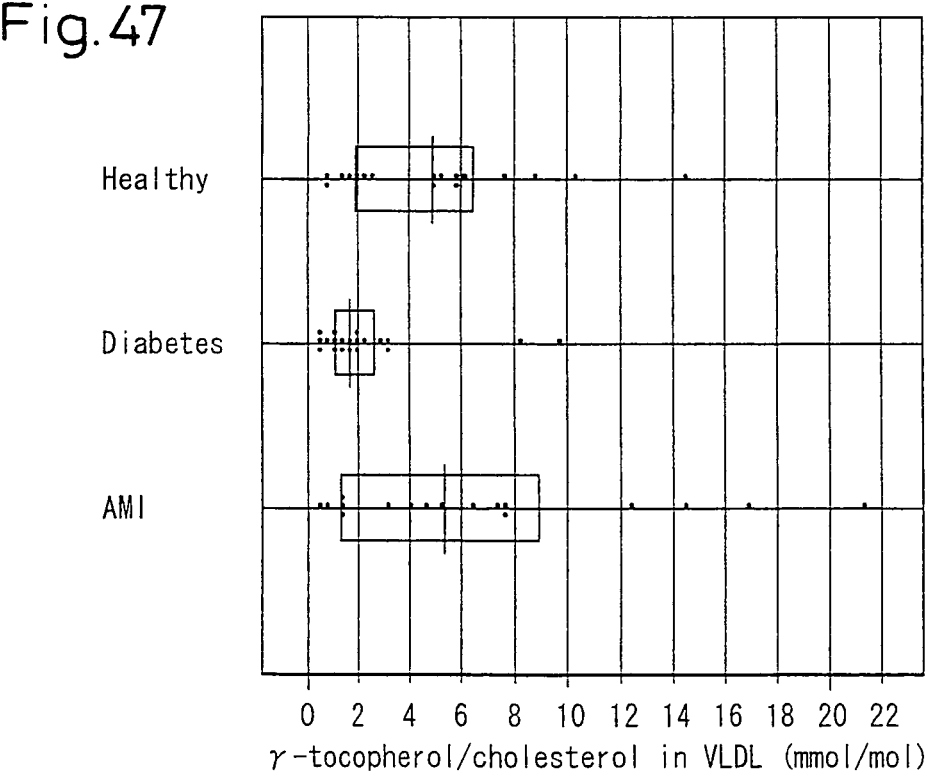
FIG. 47 shows the γ-tocopherol/cholesterol value in VLDL.

The γ-tocopherol/cholesterol values in the VLDL are shown in FIG. 47 and Table 8. Diabetes (mean value: 2.39 mmol/mol) was significantly (p=0.018) lower than the healthy individuals (mean value: 5.05 mmol/mol), indicating that γ-tocopherol in the VLDL was decomposed by oxidative stress, a pathological condition carried by diabetes. This demonstrates that by examining the γ-tocopherol/cholesterol value in the VLDL, a pathological condition related to oxidative stress of diabetes can be judged.

Figure 48:
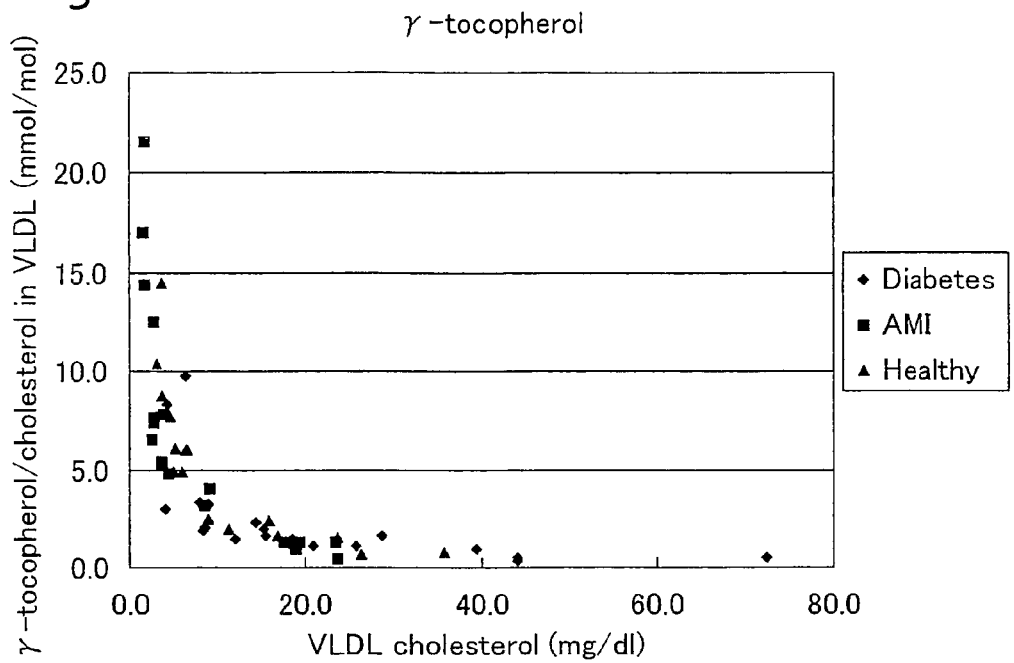
FIG. 48 shows a relationship between the γ-tocopherol/cholesterol value and VLDL cholesterol in VLDL.
Figure 49:
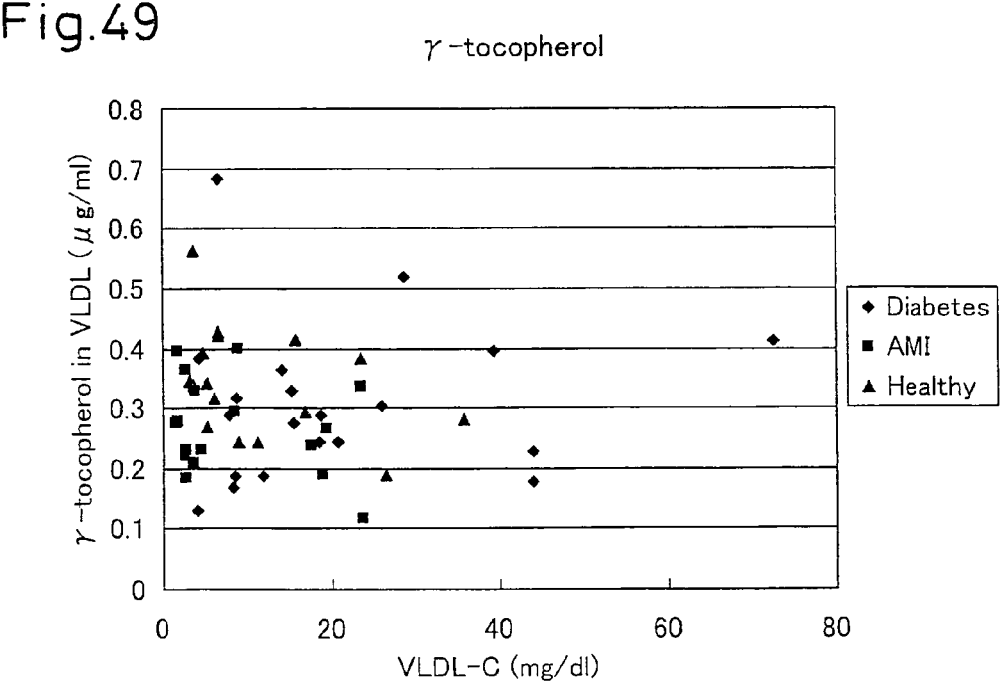
FIG. 49 shows that there is no relationship between VLDL cholesterol and the γ-tocopherol value in VLDL.

Also, the relationship with VLDL cholesterol is shown in FIG. 48. In patients with myocardial infarction which is a coronary artery disease, there is no overall decline compared to the healthy individuals, but the distribution was wider, the 25 percentile value (1.31 mmol/mol) of the patients with myocardial infarction was lower than that (1.91 mmol/mol) of the healthy individuals. VLDL cholesterol (Hubert H B et al., Am. J. Epidemiol. 125: 812 (1987)) has been demonstrated to be a risk factor for coronary artery diseases, and the relationship between this VLDL cholesterol and the γ-tocopherol/cholesterol value in the VLDL was investigated. It can be seen that as VLDL cholesterol tends to become high, not only in the patients with myocardial infarction but in the patients with diabetes and in the healthy individuals, the γ-tocopherol/cholesterol value in the VLDL sharply drops. There was no relationship between VLDL cholesterol and the γ-tocopherol/cholesterol value in the VLDL (FIG. 49). Among the healthy individuals, those having a γ-tocopherol/cholesterol value in the VLDL of 3 mmol/mol or less had the VLDL cholesterol value of 9 mg/dL or higher, or individuals having a high risk of myocardial infarction. Considering this result, it may be assumed that there are individuals having a high risk of myocardial infarction among the healthy individuals. Based on this, it can be said that the γ-tocopherol/cholesterol value in the VLDL can precisely judge the risk of a coronary artery disease when VLDL cholesterol is relatively low. Taken together that the value in diabetes which is a pathological condition known to become a high risk of arteriosclerotic diseases such as coronary artery disease was low, it can be said that the γ-tocopherol/cholesterol value in the VLDL can be used to judge the risk of a coronary artery disease.

Figure 50:
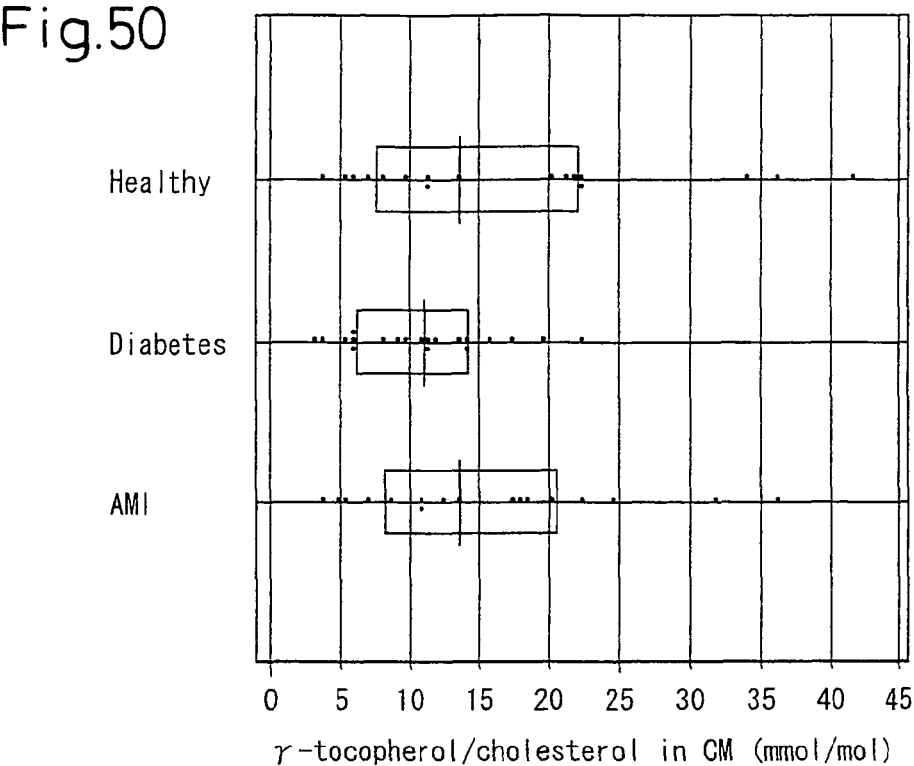
FIG. 50 shows the γ-tocopherol/cholesterol value in CM.

The γ-tocopherol/cholesterol values in the CM are shown in FIG. 50 and Table 8. Diabetes (mean value: 11.04 mmol/mol) was significantly (p=0.047) lower than the healthy individuals (mean value: 17.42 mmol/mol), indicating that γ-tocopherol in the CM was decomposed by oxidative stress, a pathological condition carried by diabetes. Though there was no significant difference (p=0.637) seen for myocardial infarction either, the mean value (mean value: 5.71 mmol/mol) was lower than the healthy individuals, which is also thought to be due to decomposition by oxidative stress.

Figure 51:
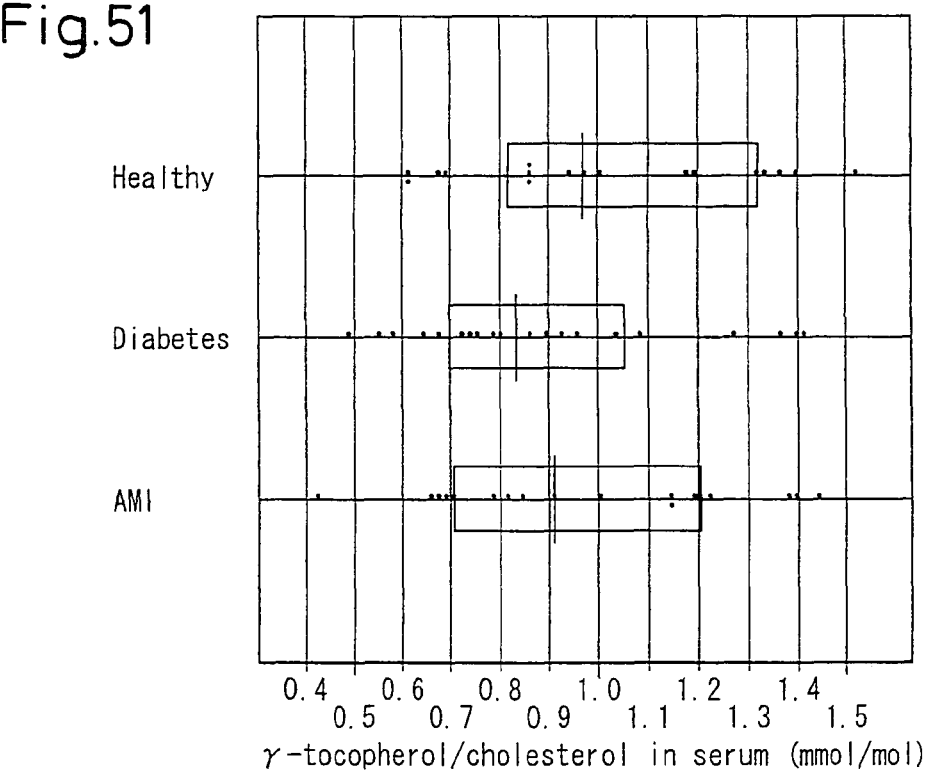
FIG. 51 shows the γ-tocopherol/cholesterol value in the blood.

The γ-tocopherol/cholesterol values in the blood are shown in FIG. 51 and Table 8. Diabetes (mean value: 0.90 mmol/mol) and myocardial infarction (mean value: 0.97 mmol/mol) were not significantly different (p=0.199 and p=0.584), but were lower than the healthy individuals (mean value: 1.03 mmol/mol). In FIG. 51, patients with diabetes and patients with myocardial infarction having values evidently lower than the healthy individuals can be recognized though the number of the patients is small. This indicates that the γ-tocopherol in the blood was decomposed by oxidative stress, a pathological condition carried by diabetes and myocardial infarction.

Figure 52:
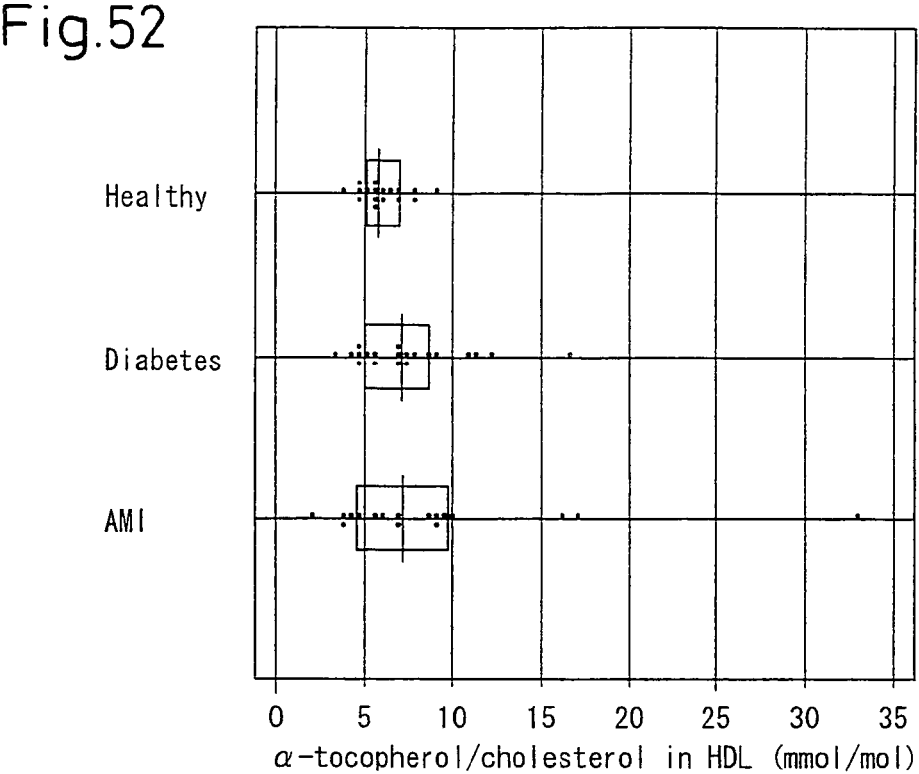
FIG. 52 shows the α-tocopherol/cholesterol value in HDL.

The α-tocopherol/cholesterol values (α-tocopherol value per cholesterol) in the HDL are shown in FIG. 52 and Table 9.

TABLE 9

| | | α tocopherol/cholesterol | | | | | |
|---|---|---|---|---|---|---|---|
| | | HDL mmol/mol | LDL mmol/mol | IDL mmol/mol | VLDL mmol/mol | CM mmol/mol | Serum mmol/mol |
| Diabetes | Mean | 7.58 | 3.33 | 15.33 | 13.46 | 45.37 | 5.51 |
| | SD | 3.26 | 2.20 | 9.89 | 15.05 | 28.19 | 1.98 |
| AMI | Mean | 9.30 | 3.94 | 24.39 | 26.47 | 55.39 | 6.83 |
| | SD | 7.36 | 1.58 | 14.84 | 21.26 | 35.18 | 2.54 |
| Healthy | Mean | 6.09 | 2.01 | 20.14 | 17.51 | 64.73 | 4.71 |
| | SD | 1.31 | 0.45 | 7.70 | 12.20 | 53.16 | 1.18 |
| Significant test, Nonparametric | Healthy vs Diabetes | 0.072 | 0.016 | 0.106 | 0.373 | 0.190 | 0.136 |
| | Healthy vs AMI | 0.095 | 0.0001 | 0.305 | 0.144 | 0.551 | 0.005 |

When diabetes (mean value: 7.58 mmol/mol) and myocardial infarction (mean value: 9.30 mmol/mol) were compared to healthy individuals (mean value: 6.09 mmol/mol), there were no significant differences ($p=0.072$ and $p=0.095$), but showed a tendency toward higher values. Since HDL is an important lipoprotein responsible for the central role in lipid metabolism, this is thought that the content of α-tocopherol in the HDL increased as a protection against damages due to oxidative stress, a pathological condition carried by diabetes and myocardial infarction.

Figure 53:
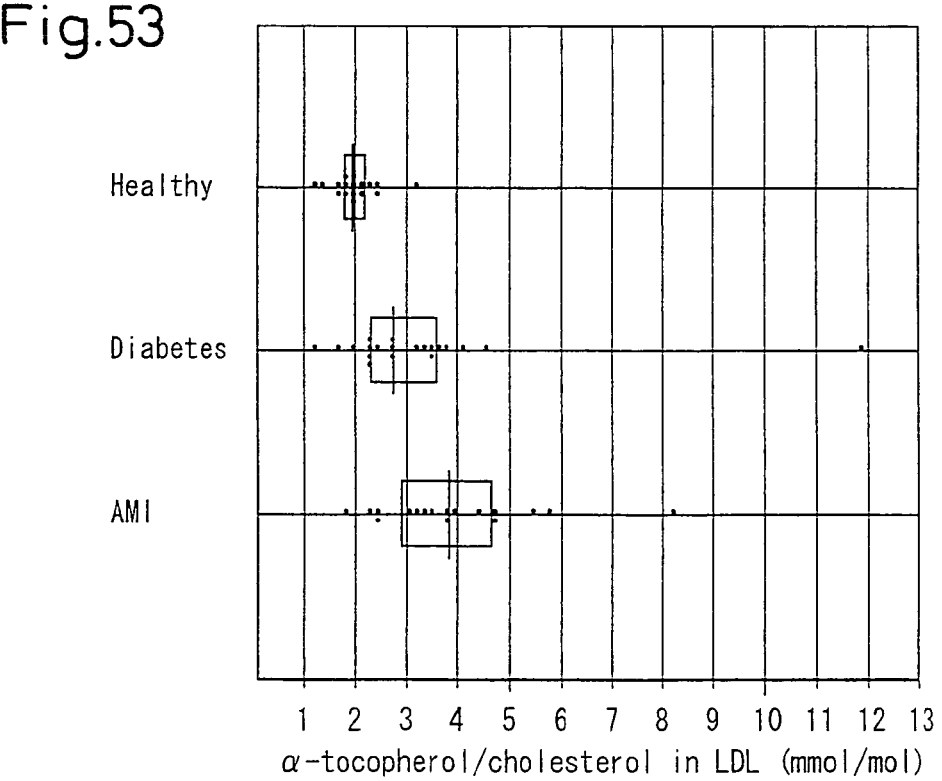
FIG. 53 shows the α-tocopherol/cholesterol value in LDL.

The α-tocopherol/cholesterol values in the LDL are shown in FIG. 53 and Table 9. Diabetes (mean value: 3.33 mmol/mol) was significantly ($p=0.016$) higher than the healthy individuals (mean value: 2.01 mmol/mol). Since LDL is an important lipoprotein responsible for the central role in lipid metabolism, this is thought that the content of α-tocopherol in the LDL increased as a protection against damages due to oxidative stress, a pathological condition carried by diabetes. Thus, it can be said that the α-tocopherol/cholesterol value in the LDL can be used to judge the pathological conditions related to oxidative stress of diabetes.

Myocardial infarction (mean value: 3.94 mmol/mol) was also significantly ($p=0.0001$) higher than the healthy individuals (mean value: 2.01 mmol/mol). Since LDL is an important lipoprotein responsible for the central role in lipid metabolism, this is thought that the content of α-tocopherol in the LDL increased as a protection against damages due to oxidative stress, a pathological condition carried by myocardial infarction. Thus, it can be said that the α-tocopherol/cholesterol value in the LDL can be used to judge the pathological conditions related to oxidative stress of myocardial infarction.

Figure 54:
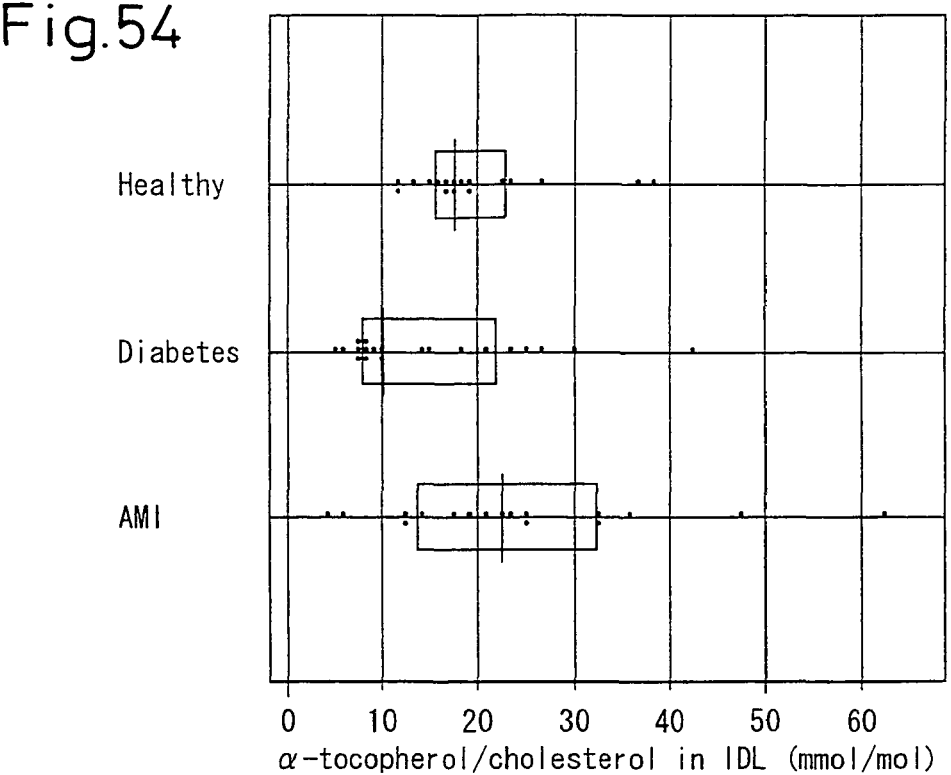
FIG. 54 shows the α-tocopherol/cholesterol value in IDL.

The α-tocopherol/cholesterol values in the IDL are shown in FIG. 54 and Table 9. It can be seen that though the significant difference ($p=0.106$) was small, diabetes (mean value: 15.33 mmol/mol) was obviously lower than the healthy individuals (mean value: 20.14 mmol/mol). This indicates that α-tocopherol in the IDL was decomposed by oxidative stress, a pathological condition carried by diabetes. Myocardial infarction (mean value: 24.39 mmol/mol) was higher than the healthy individuals (mean value: 20.14 mmol/mol), but in the values of patients with myocardial infarction, variation between higher patients and lower patients was great compared to the healthy individuals. In fact, the 25 percentile value of 13.7 mmol/mol of the patients with myocardial infarction was lower than the 25 percentile value of 15.7 mmol/mol of the healthy individuals. Considering the possibility that there may be some healthy individuals in whom α-tocopherol in the IDL has been decomposed by oxidative stress, the decomposition of α-tocopherol in the IDL due to oxidative stress should be more advanced in patients with myocardial infarction having a value lower than the percentile value of 15.7 mmol/mol of the healthy individuals.

Figure 55:
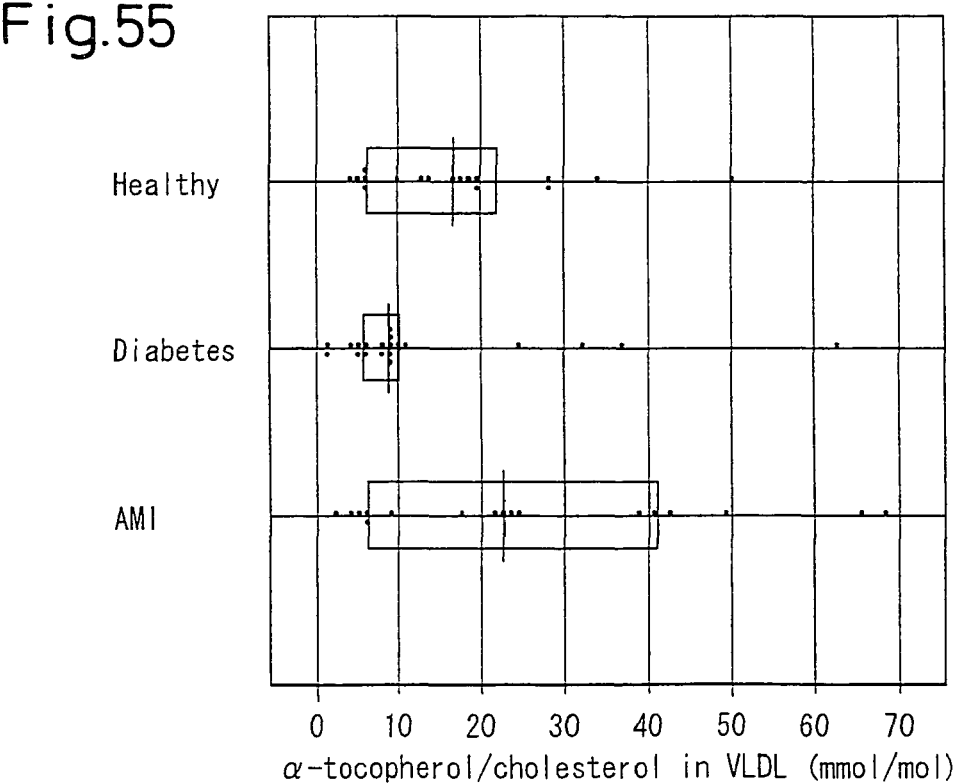
FIG. 55 shows the α-tocopherol/cholesterol value in VLDL.

The α-tocopherol/cholesterol values in the VLDL are shown in FIG. 55 and Table 9. Though there is no significant difference ($p=0.373$), diabetes (mean value: 13.46 mmol/mol) was obviously lower than the healthy individuals (mean value: 17.51 mmol/mol), indicating that α-tocopherol in the VLDL was decomposed by oxidative stress, a pathological condition carried by diabetes. Thus, it can be said that the α-tocopherol/cholesterol value in the VLDL can judge the pathological condition related to oxidative stress of diabetes.

Figure 56:
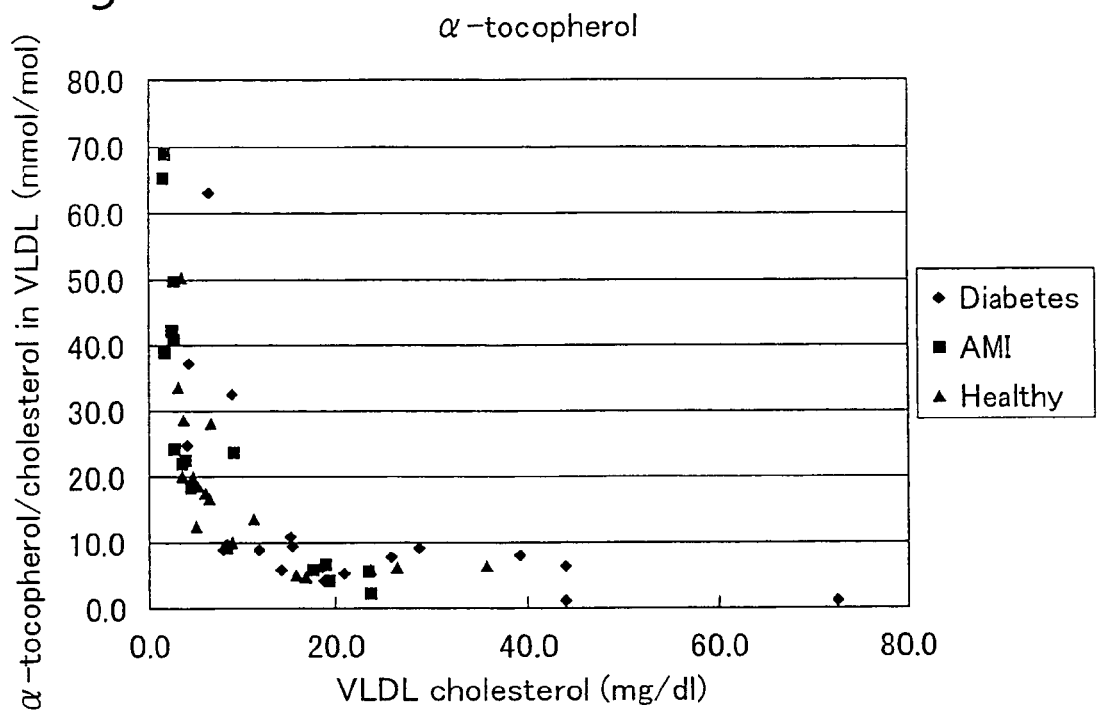
FIG. 56 shows a relationship between the α-tocopherol/ cholesterol value and VLDL cholesterol in VLDL.
Figure 57:
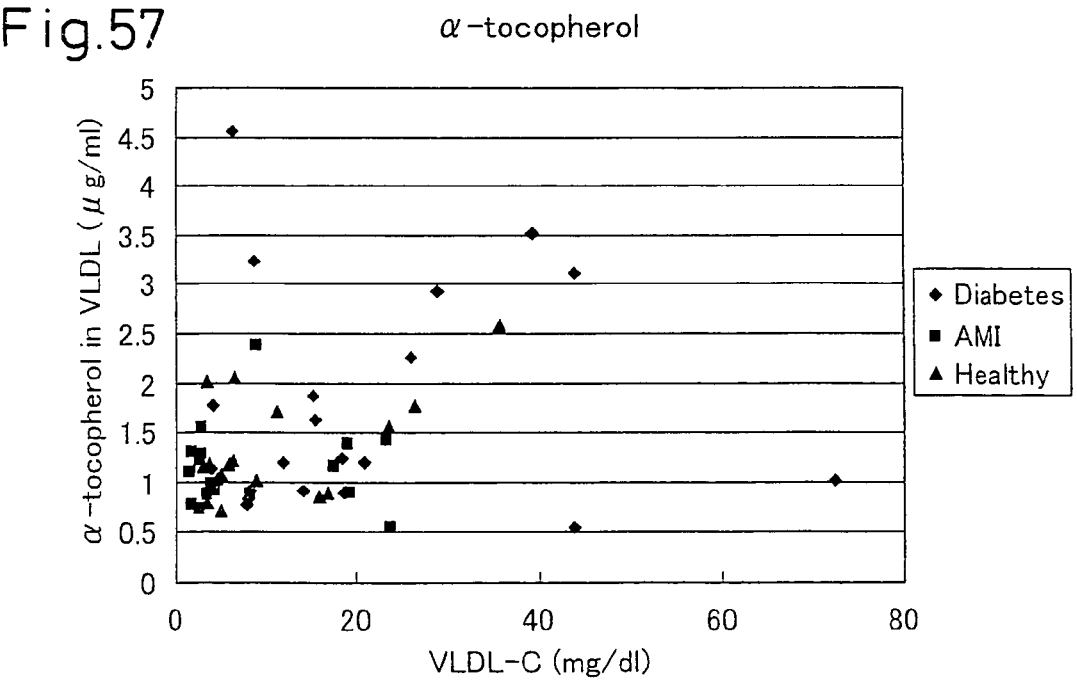
FIG. 57 shows that there is no relationship between VLDL cholesterol and the α-tocopherol value in VLDL.

Also, the relationship with VLDL cholesterol is shown in FIG. 56. In patients with myocardial infarction which is a coronary artery disease, there is no overall decline compared to the healthy individuals. But this result is possibly because some healthy individuals are expected to have a high risk of myocardial infarction. Then, VLDL cholesterol has been demonstrated to be a risk factor for coronary artery diseases (Hubert H B et al., (1987), supra), and the relationship between this VLDL cholesterol and the α-tocopherol/cholesterol value in the VLDL was investigated. It can be seen that as VLDL cholesterol tends to become high, not only in the patients with myocardial infarction but in patients with diabetes and the healthy individuals, the α-tocopherol/cholesterol value in the VLDL sharply drops. There was no relationship between the VLDL cholesterol and the α-tocopherol/cholesterol value in the VLDL (FIG. 57). Among the healthy individuals, those having a α-tocopherol/cholesterol value of 7 mmol/mol or less in the VLDL had high VLDL cholesterol values of 15 mg/dL or higher, indicating that they are individuals having a high risk of myocardial infarction. Based on this, it can be said that the α-tocopherol/cholesterol value in the VLDL can precisely judge the risk of a coronary artery disease when VLDL cholesterol is low. Taken together that the value in diabetes which is a pathological condition known to become a high risk of arteriosclerotic diseases such as coronary artery disease was low, it can be said that the α-tocopherol/cholesterol value in the VLDL can be used to judge the risk of a coronary artery disease.

Figure 58:
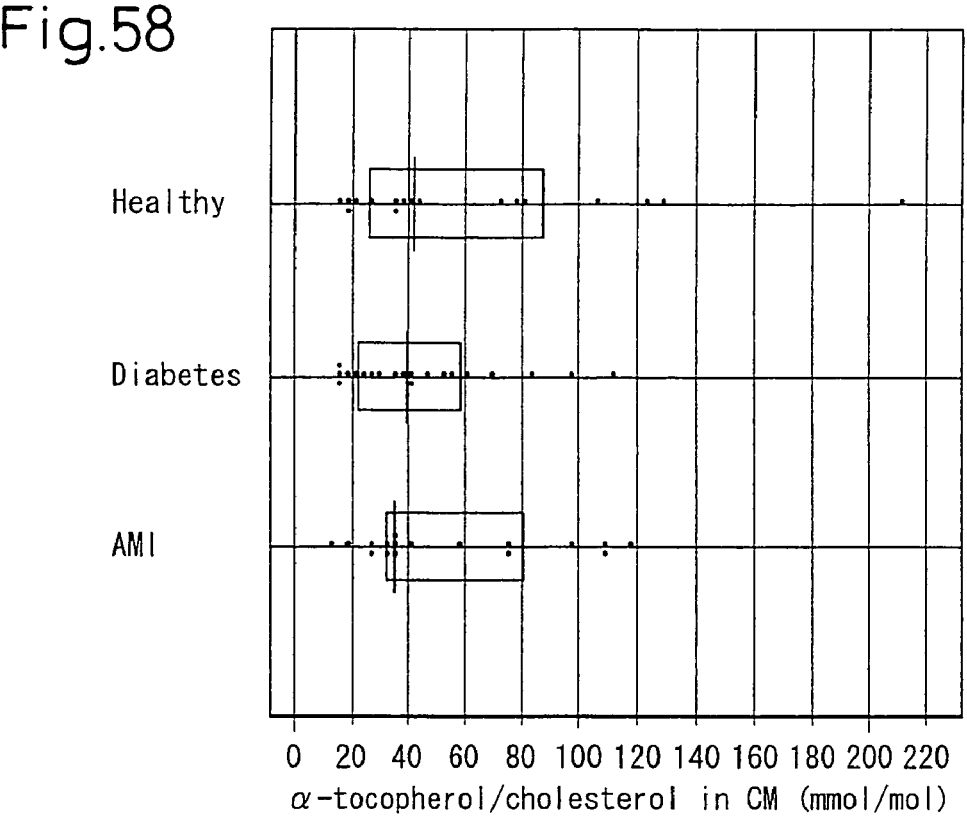
FIG. 58 shows the α-tocopherol/cholesterol value in CM.

The α-tocopherol/cholesterol values in the CM are shown in FIG. 58 and Table 9. Though there is no significant difference (P=0.190), diabetes (mean value: 45.37 mmol/mol) tended to be lower than the healthy individuals (mean value: 64.73 mmol/mol), indicating that α-tocopherol in the CM was decomposed by oxidative stress, a pathological condition carried by diabetes. For myocardial infarction, the significant difference p=0.551 was further lower than for diabetes, and the mean value of 55.39 mmol/mol was lower than the healthy individuals, which is also thought to be due to decomposition by oxidative stress.

Figure 59:
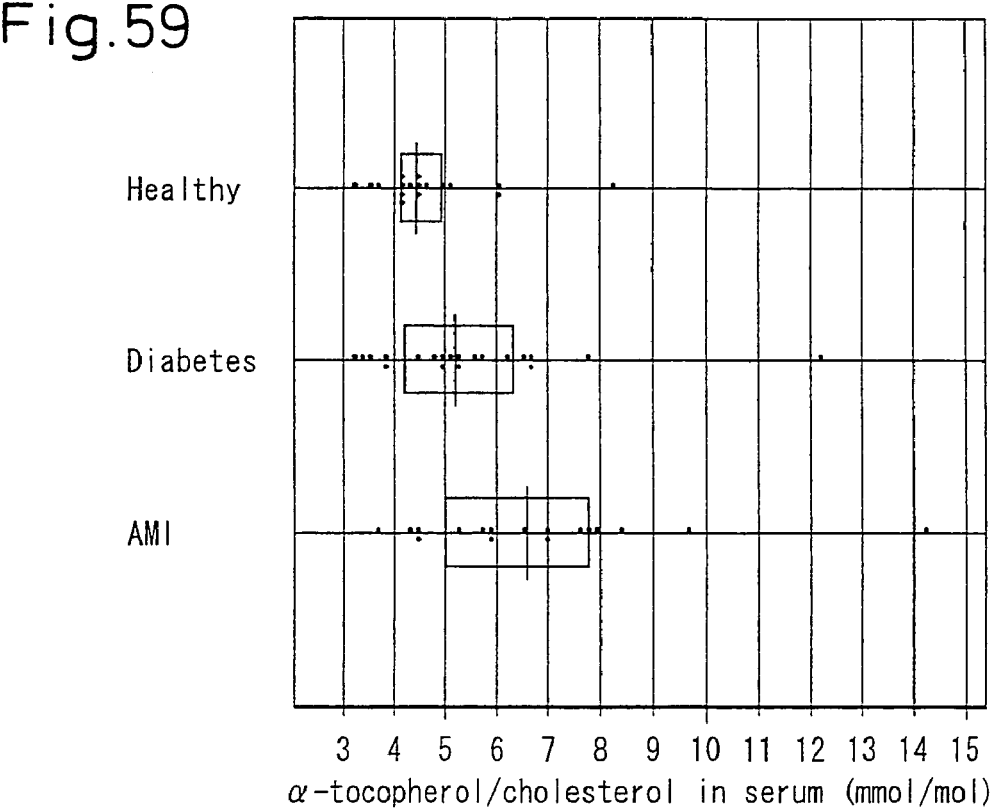
FIG. 59 shows the α-tocopherol/cholesterol value in the blood.

The α-tocopherol/cholesterol values in the blood are shown in FIG. 59 and Table 9. With the significant difference being p=0.005, myocardial infarction (mean value: 6.83 mmol/mol) was evidently higher than the healthy individuals (mean value: 4.71 mmol/mol), and this is thought that LDL and HDL which are major lipoproteins in the blood enhanced the content of α-tocopherol as a protection against damages due to oxidative stress, a pathological condition carried by diabetes. For diabetes, though there was no significant difference (P=0.136), the value was higher than the healthy individuals (mean value: 4.71 mmol/mol), and this is also thought that LDL and HDL which are major lipoproteins in the blood enhanced the content of α-tocopherol as a protection against damages due to oxidative stress, a pathological condition carried by diabetes.

Figure 60:
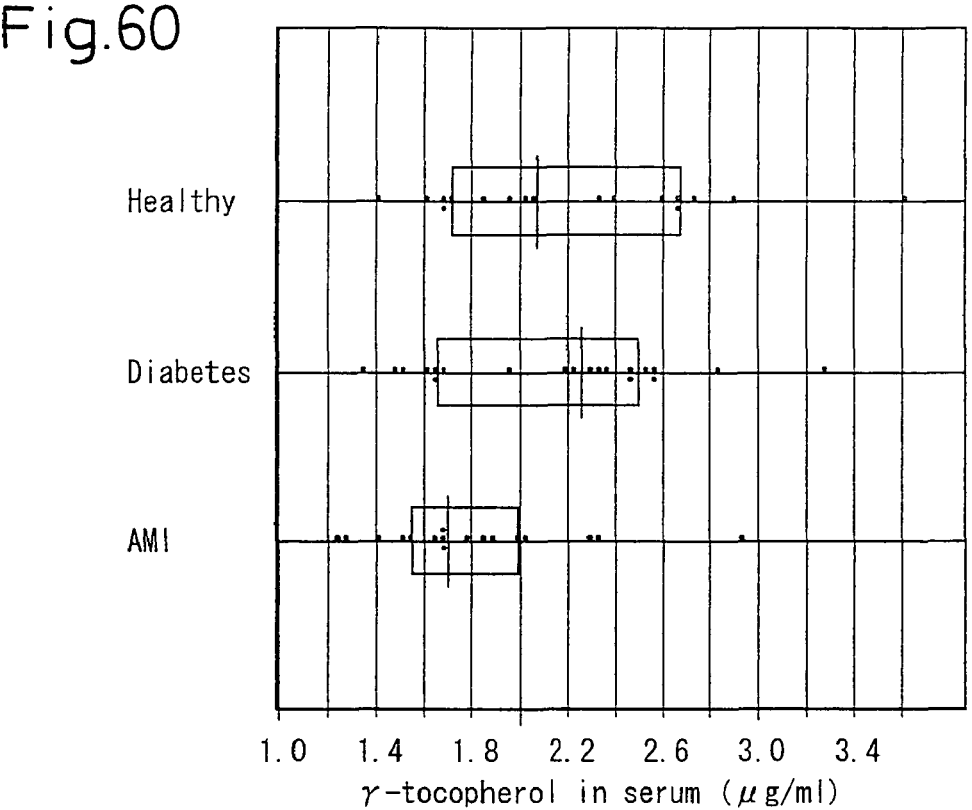
FIG. 60 shows the γ-tocopherol value in the blood.
Figure 61:
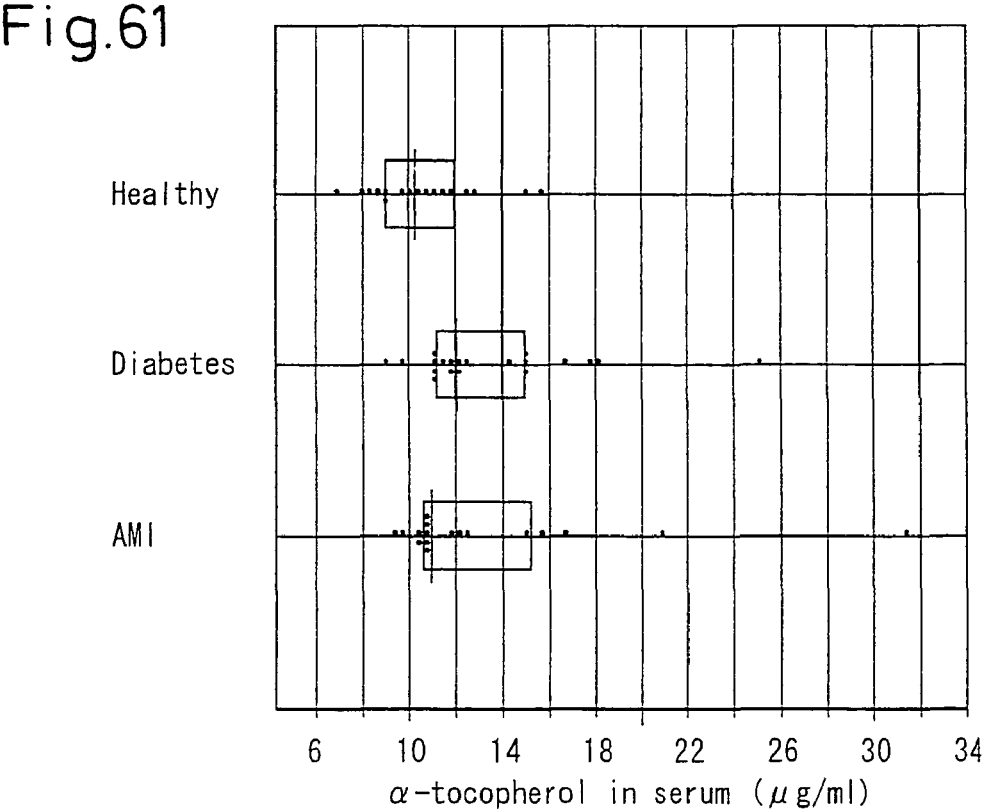
FIG. 61 shows the α-tocopherol value in the blood.

For the healthy individuals and diabetes, the α-tocopherol value and the γ-tocopherol value in the blood were compared (FIGS. 60, 61). The α-tocopherol value (mean value: 13.63 μg/ml) of the patients with diabetes was evidently higher than the healthy individuals (mean value: 10.70 μg/ml), and the mean value of γ-tocopherol was slightly lower in patients with diabetes (mean value: 2.15 μg/ml) compared to the healthy individuals (mean value 2.23 μg/ml), but in the overall distribution, some patients with diabetes had a high value compared to the healthy individuals, and the central value is slightly higher (healthy individuals: central value 2.07 μg/ml, patients with diabetes: central value 2.26 μg/ml). This phenomenon of high values of vitamin E (α-tocopherol and γ-tocopherol) is thought to be one of the protective mechanism against oxidative stress occurring in the body of patients with diabetes.

Also, there is a phenomenon that as compared to α-tocopherol, γ-tocopherol is more vulnerable to decomposition by radicals generated by oxidative stress. Also, it is known that α-tocopherol and γ-tocopherol are similarly absorbed by the intestine, transported via chylomicron to the liver or part thereof is to the peripheral cells, and in the liver by the vitamin E-transporting protein, a certain amount of α-tocopherol and γ-tocopherol are contained in the VLDL particles and liberated into the blood so as to be transported to the peripheral cells in the body. From a similar mechanism, the ratio of α-tocopherol and γ-tocopherol absorbed in the intestine and liberated from the liver in the blood is estimated to be almost constant. Based on these phenomena, it was predicted an investigated that the ratio of γ-tocopherol to α-tocopherol would be an excellent index that reflects the pathological conditions related to oxidative stress of diabetes. The results are shown in FIG. 62 and Table 10. The ratio of γ-tocopherol/α-tocopherol in the blood is, as predicted, significantly (p=0.013) lower in patients (mean value: 0.17) with diabetes than the healthy individuals (mean value: 0.22), indicating that it can be used to judge the pathological conditions related to oxidative stress of diabetes.

TABLE 10

| | | Serum | | |
|---|---|---|---|---|
| | | γ tocopherol (μg/ml) | α tocopherol (μg/ml) | γ tocopherol/ α tocopherol |
| Diabetes | Mean | 2.15 | 13.63 | 0.17 |
| | SD | 0.51 | 3.74 | 0.05 |
| AMI | Mean | 1.82 | 13.59 | 0.15 |
| | SD | 0.42 | 5.54 | 0.06 |
| Healthy | Mean | 2.23 | 10.70 | 0.22 |
| | SD | 0.58 | 2.41 | 0.06 |
| Significant test, Non-parametric | Healthy vs Diabetes | 0.661 | 0.007 | 0.013 |
| | Healthy vs AMI | 0.023 | 0.061 | 0.005 |

Also, the result that in coronary artery diseases, α-tocopherol is slightly higher than the healthy individuals although not significant (p=0.061), was agreed that γ-tocopherol/α-tocopherol ratio is significantly (P=0.005) low is largely consistent with the contents described in Ohrvall M. et al. (1996), supra.

The invention claimed is:

1. A method of analyzing vitamin E components in sample containing lipoproteins, which comprises
    subjecting the sample to an ion exchange chromatography to separate the lipoproteins from the sample,
    reacting the separated lipoproteins with a pretreating solution containing an organic solvent and a surfactant to liberate vitamin E components from the separated lipoproteins, and then
    subjecting the liberated vitamin E components to a reverse phase chromatography.

2. The analytical method according to claim 1 wherein the pretreating solution comprises an organic solvent which is 10-50% by volume and a surfactant which is 0.2-6.0% by weight at the step of reacting with the lipoprotein separated by the ion exchange chromatography.

3. The analytical method according to claim 1 wherein the pretreating solution further comprises a caotropic ion which is 50-150 mmol/L at the step of reacting with the lipoprotein separated by the ion exchange chromatography.

* * * * *